US007279166B2

(12) United States Patent
Meng et al.

(10) Patent No.: US 7,279,166 B2
(45) Date of Patent: Oct. 9, 2007

(54) CHIMERIC INFECTIOUS DNA CLONES, CHIMERIC PORCINE CIRCOVIRUSES AND USES THEREOF

(75) Inventors: Xiang-Jin Meng, Blacksburg, VA (US); Martijn Fenaux, Redwood City, CA (US); Patrick G. Halbur, Ames, IA (US)

(73) Assignees: Virginia Tech Intellectual Properties, Inc., Blacksburg, VA (US); Iowa State University Research Foundation, Inc., Ames, IA (US)

( * ) Notice: Subject to any disclaimer, the term of this patent is extended or adjusted under 35 U.S.C. 154(b) by 198 days.

(21) Appl. No.: 10/808,964

(22) Filed: Mar. 25, 2004

(65) Prior Publication Data

US 2004/0253270 A1    Dec. 16, 2004

Related U.S. Application Data

(63) Continuation-in-part of application No. 10/314,512, filed on Dec. 9, 2002.

(60) Provisional application No. 60/424,840, filed on Nov. 8, 2002, provisional application No. 60/340,775, filed on Dec. 12, 2001.

(51) Int. Cl.
*A61K 39/12*       (2006.01)
*C12N 15/09*       (2006.01)

(52) U.S. Cl. .............................. 424/199.1; 424/204.1; 536/23.1; 536/23.72; 435/69.1; 435/440; 435/455

(58) Field of Classification Search ............. 424/199.1, 424/130.1, 133.1, 208.1; 536/23.72
See application file for complete search history.

(56) References Cited

U.S. PATENT DOCUMENTS

| | | | |
|---|---|---|---|
| 6,217,883 B1 | 4/2001 | Allan et al. ............... | 424/202.1 |
| 6,287,856 B1 | 9/2001 | Poet et al. ................ | 435/320.1 |
| 6,368,601 B1 | 4/2002 | Allan et al. ............... | 424/204.1 |
| 6,391,314 B1 | 5/2002 | Allan et al. ............... | 424/204.1 |
| 6,497,883 B1 | 12/2002 | Bublot et al. ............. | 424/204.1 |
| 6,703,023 B1 | 3/2004 | Jestin et al. | |
| 6,943,152 B1 * | 9/2005 | Audonnet et al. ............ | 514/44 |
| 2002/0055189 A1 | 5/2002 | Bernhardt et al. .......... | 436/548 |
| 2002/0146431 A1 | 10/2002 | Allan et al. ............... | 424/202.1 |
| 2002/0177216 A1 | 11/2002 | Liu et al. ................. | 435/235.1 |
| 2003/0003112 A1 | 1/2003 | Audonnet et al. ....... | 424/232.1 |

FOREIGN PATENT DOCUMENTS

| | | |
|---|---|---|
| FR | 2 772 047 | 6/1999 |
| WO | 99/18214 | 4/1999 |
| WO | WO 99/29871 A2 | 6/1999 |
| WO | 99/45956 | 9/1999 |
| WO | 00/01409 | 1/2000 |
| WO | 00/77216 A2 | 12/2000 |
| WO | WO 00/77188 A2 | 12/2000 |
| WO | 01/16330 A2 | 3/2001 |
| WO | 01/83737 A2 | 11/2001 |
| WO | 01/96377 A2 | 12/2001 |
| WO | 02/077210 A2 | 10/2002 |
| WO | 02/102999 A2 | 12/2002 |

OTHER PUBLICATIONS

Sequence alignment of SEQ ID No. 2 against Genseq database accession No. AAL57177, submitted Oct. 27, 2003 by applicant in WO 2003049703-A2.*
Fenuax et al. Journal of Virology. 2004; 78 (12): 6297-6303.*
Krakowka et al. Viral Immunology. 2002; 15 (4): 567-582.*
M. Fenaux et al., Genetic Characterization of Type 2 Porcine Circovirus (PCV-2) from Pigs with Postweaning Multisystemic Wasting Syndrome in Different Geographic Regions of North America and Development of a Differential PCR-Restriction Fragment Length Polymorphism Assay To Detect and Differentiate between Infections with PCV-1 and PCV-2, J. Clin. Microbiol. 38 (7):2494-2503 (Jul. 2000).
P. Nawagitgul et al., "Open reading frame 2 of porcine circovirus type 2 encodes a major capsid protein," Journal of General Virology 81:2281-2287 (2000).
D. Mahé et al., "Differential recognition of ORF2 protein from type 1 and type 2 porcine circoviruses and identification of immunorelevant epitopes," Journal of General Virology 81:1815-1824 (2000).
S. Lustig et al., "Molecular Basis of Sindbis Virus Neurovirulence in Mice," Journal of Virology 62(7):2329-2336 (Jul. 1988).
M. Caggana et al., "Identification of a Single Amino Acid Residue in the Capsid Protein VP1 of Coxsackievirus B4 That Determines the Virulent Phenotype," Journal of Virology 67(8):4797-4803 (Aug. 1993).

(Continued)

*Primary Examiner*—Stacy B. Chen
(74) *Attorney, Agent, or Firm*—Adley F. Mandel; Anne M. Rosenblum

(57) ABSTRACT

The present invention relates to infectious DNA clones, infectious chimeric DNA clones of porcine circovirus (PCV), vaccines and means of protecting pigs against viral infection or postweaning multisystemic wasting syndrome (PMWS) caused by PCV2. The new chimeric infectious DNA clone and its derived, avirulent chimeric virus are constructed from the nonpathogenic PCV1 in which the immunogenic ORF gene of the pathogenic PCV2 replaces a gene of the nonpathogenic PCV1, preferably in the same position. The chimeric virus advantageously retains the nonpathogenic phenotype of PCV1 but elicits specific immune responses against the pathogenic PCV2. The invention further embraces the immunogenic polypeptide expression products. In addition, the invention encompasses two mutations in the PCV2 immunogenic capsid gene and protein, and the introduction of the ORF2 mutations in the chimeric clones.

26 Claims, 15 Drawing Sheets

OTHER PUBLICATIONS

Liu et al., "Bacterial Expression of an Immunologically Reactive PCV2 ORF2 Fusion Protein," Protein Expression and Purification, 2001, 21:115-120.

Pogranichnyy et al., "Characterization of Immune Response of Young Pigs to Porcine Circovirus Type 2 Infection," Viral Immunology, 2000, 13(2):143-153.

Meehan et al., "Characterization of novel circovirus DNAs associated with wasting syndromes in pigs," J. Gen. Virology, SGM, Sep. 1998, 79(9):2171-2179, XP002090386.

Fenaux et al., "Immunogenicity and Pathogenicity of Chimeric Infectious DNA Clones of Pathogenic Porcine Circovirus Type 2 (PCV2) and Nonpathogenic PCV1 in Weanling Pigs," J. Virology, Oct. 2003, 77(20):11232-11243.

Fenaux et al., "A Chimeric Procine Circovirus (PCV) with the Immunogenic Capsid Gene of the Pathogenic PCV Type 2 (PCV2) in Cloned into the Genomic Backbone of the Nonpathogenic PCV1 Induces Protective Immunity Against PCV2 Infection in Pigs," J. Virology, Jun. 2004, 78(12):6297-6303.

\* cited by examiner

R-PCVSAC2 ← Sac II → F-PCVSAC2

PCV2
1,766 bp

PCR
Sac II digestion
and DNA ligation

Sac II — PCV2 — Sac II — PCV2 — Sac II
Tandem dimer of PCV2 genome

Ligation into pSK plasmid

Sac II — PCV2 — Sac II — PCV2 — Sac II
PCV2 molecular DNA clone
6,490 bp
pSK+

FIG. 1

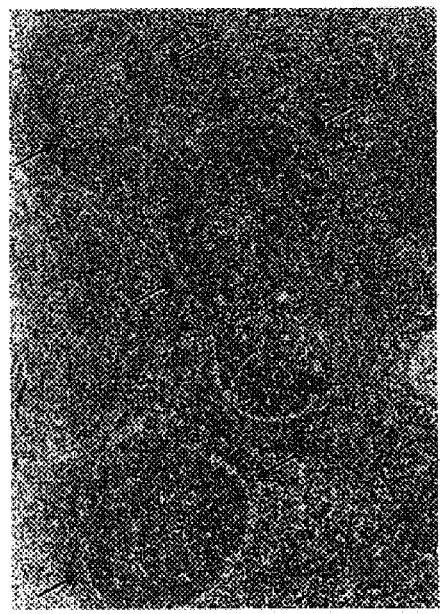
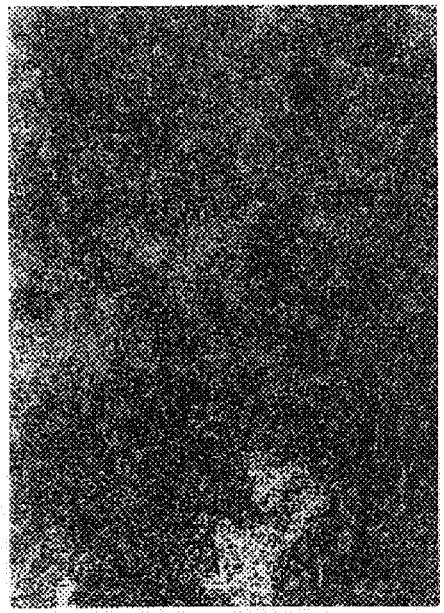
FIG.4A  FIG.4B
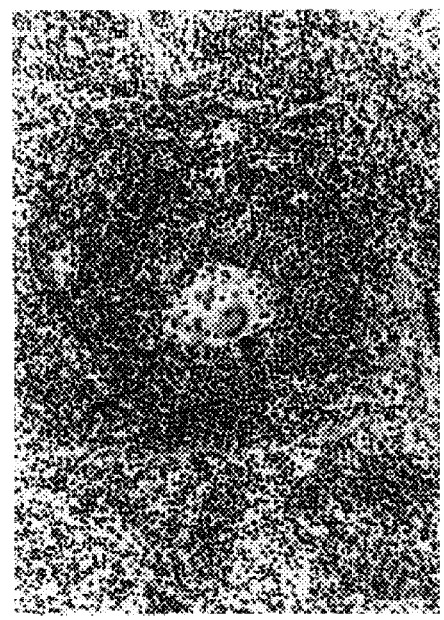
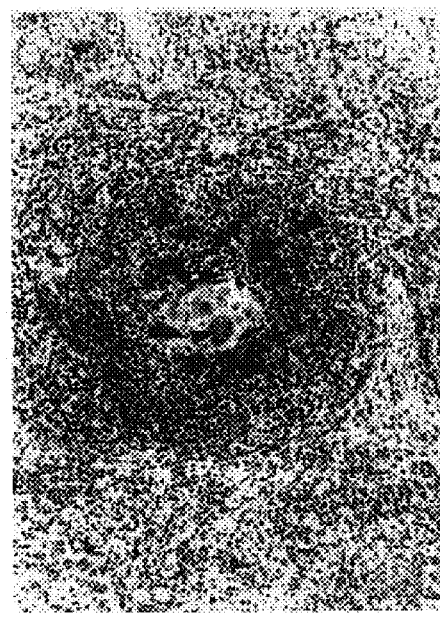
FIG.4C  FIG.4D

IFA WITH
ANTI-PCV1 ORF2

IFA WITH
ANTI-PCV2

IFA WITH
ANTI-PCV1 ORF2

IFA WITH
ANTI-PCV2

IFA WITH
ANTI-PCV1 ORF2

IFA WITH
ANTI-PCV2

IFA WITH
ANTI-PCV1 ORF2

IFA WITH
ANTI-PCV2

IFA WITH
ANTI-PCV1 ORF2

IFA WITH
ANTI-PCV2

```
AAATTTCTGACAAACGTTACAGGGTGCTGCTCTGCAACGGTCACCAGACTCCCGCTCTCC
AACAAGGTACTCACAGCAGTAGACAGGTCACTCCGTTGTCCTTGAGATCGAGGAGCTCCA
CATTCAATAAGTAAGTTGCCTTCTTTACTGCAATATTCTTTATTCTGCTGATCAGTTCCT
TTGGCTTTCTCGATATGGCAGCGGGCACCCAAATACCACTTCACTTTATTAAAAGTTTGC
TTCTTCACAAAATTAGCGAACCCCTGGAGGTGAGGTGTTCGTCCTTCCTCATTACCCTCC
TCGCCAACAATAAAATAATCAAATAGGGAGATTGGGAGCTCCCGTATTTTCTTGCGCTCG
TCTTCGGAAGGATTATTCAGCGTGAACACCCACCTTTTATGTGGTTGGGGTCCGCTTCTT
CCATTCTTCTTGCTGGGCATGTTGCTGCTGAGGTGCTGCCGAGGTGCTGCCGCTGCCGAA
GTGCGCTGGTAATACTTACAGCGCACTTCTTTCGTTTTCAGCTATGACGTATCCAAGGAG
GCGTTACCGCAGAAGAAGACACCGCCCCCGCAGCCATCTTGGCCAGATCCTCCGCCGCCG
CCCCTGGCTCGTCCACCCCCGCCACCGCTACCGTTGGAGAAGGAAAAATGGCATCTTCAA
CACCCGCCTCTCCCGCACCTTCGGATATACTGTCAAGGCTACCACAGTCAGAACGCCCTC
CTGGGCGGTGGACATGATGAGATTTAATATTGACGACTTTGTTCCCCCGGGAGGGGGGAC
CAACAAAATCTCTATACCCTTTGAATACTACAGAATAAGAAAGGTTAAGGTTGAATTCTG
GCCCTGCTCCCCCATCACCCAGGGTGATAGGGGAGTGGGCTCCACTGCTGTTATTCTAGA
TGATAACTTTGTAACAAAGGCCACAGCCCTAACCTATGACCCATATGTAAACTACTCCTC
CCGCCATACAATCCCCCAACCCTTCTCCTACCACTCCCGTTACTTCACACCCAAACCTGT
TCTTGACTCCACCATTGATTACTTCCAACCAAATAACAAAAGGAATCAGCTTTGGATGAG
GCTACAAACCTCTAGAAATGTGGACCACGTAGGCCTCGGCACTGCGTTCGAAAACAGTAT
ATACGACCAGGACTACAATATCCGTGTAACCATGTATGTACAATTCAGAGAATTTAATCT
TAAAGACCCCCCACTTAAACCCTAAATGAATAATAAAAACCATTACGAAGTGATAAAAAA
GACTCAGTAATTTATTTCATATGGAAATTCAGGGCATGGGGGGGAAAGGGTGACGAACTG
GCCCCCTTCCTCCGTGGATTGTTCTGTAGCATTCTTCCAAAATACCAAGAAAGTAATCCT
CCGATAGAGAGCTTCTACAGCTGGGACAGCAGTTGAGGAGTACCATTCCAACGGGGTCTG
ATTGCTGGTAATCAGAATACTGCGGGCCAAAAAAGGTACAGTTCGACCTTTAGTCTCTAC
AGTCAATGGATATCGATCACACAGTCTCAGTAGATCATCCCACGGCAGCCAGCCATAAAA
GTCATCAATAACAACCACTTCTTCACCATGGTAACCATCCCACCACTTGTTTCTAGGTGG
TTTCCAGTATGTGGTTTCCGGGTCTGCAAAATTAGCAGCCCATTTGCTTTTACCACACCC
AGGTGGCCCCACAATGACGTGTACATTGGTCTTCCAATCACGCTTCTGCATTTTCCCGCT
CACTTTCAAAAGTTCAGCCAGCCCGCGG
```

FIG.8

```
GGTACCTCCGTGGATTGTTCTCCAGCAGTCTTCCAAAATTGCAAAGTAGTAATCCTCCGA
TAGAGAGCTTCTACAGCTGGGACAGCAGTTGAGGAGTACCATTCCTGGGGGGCCTGATTG
CTGGTAATCAAAATACTGCGGGCCAAAAAAAGGAACAGTACCCCCTTTAGTCTCTACAGTC
AATGGATACCGGTCACACAGTCTCAGTAGATCATCCCAAGGTAACCAGCCATAAAAATCA
TCCAAAACAACAACTTCTTCTCCATGATATCCATCCCACCACTTATTTCTACTAGGCTTC
CAGTAGGTGTCCCTAGGCTCAGCAAAATTACGGGCCCACTGGCTCTTCCCACAACCGGGC
GGGCCCACTATGACGTGTACAGCTGTCTTCCAATCACGCTGCTGCATCTTCCCGCTCACT
TTCAAAAGTTCAGCCAGCCCGCGGAAATTTCTCACATACGTTACAGGAAACTGCTCGGCT
ACAGTCACCAAAGACCCCGTCTCCAAAAGGGTACTCACAGCAGTAGACAGGTCGCTGCGC
TTCCCCTGGTTCCGCGGAGCTCCACACTCGATAAGTATGTGGCCTTCTTTACTGCAGTAT
TCTTTATTCTGCTGGTCGGTTCCTTTCGCTTTCTCGATGTGGCAGCGGGCACCAAAATAC
CACTTCACCTTGTTAAAAGTCTGCTTCTTAGCAAAATTCGCAAACCCCTGGAGGTGAGGA
GTTCTACCCTCTTCCAAACCTTCCTCGCCACAAACAAAATAATCAAAAAGGGAGATTGGA
AGCTCCCGTATTTTGTTTTTCTCCTCCTCGGAAGGATTATTAAGGGTGAACACCCACCTC
TTATGGGGTTGCGGGCCGCTTTTCTTGCTTGGCATTTTCACTGACGCTGCCGAGGTGCTG
CCGCTGCCGAAGTGCGCTGGTAATACTACAGCAGCGCACTTCTTTCACTTTTATAGGATG
ACGTATCCAAGGAGGCGTTACCGCAGAAGAAGACACCGCCCCCGCAGCCATCTTGGCCAG
ATCCTCCGCCGCCGCCCTGGCTCGTCCACCCCGCCACCGCTACCGTTGGAGAAGGAAA
AATGGCATCTTCAACACCCGCCTCTCCCGCACCTTCGGATATACTGTCAAGGCTACCACA
GTCAGAACGCCCTCCTGGGCGGTGGACATGATGAGATTTAATATTGACGACTTTGTTCCC
CCGGGAGGGGGGACCAACAAAATCTCTATACCCTTTGAATACTACAGAATAAGAAAGGTT
AAGGTTGAATTCTGGCCCTGCTCCCCCATCACCCAGGGTGATAGGGGAGTGGGCTCCACT
GCTGTTATTCTAGATGATAACTTTGTAACAAAGGCCACAGCCCTAACCTATGACCCATAT
GTAAACTACTCCTCCCGCCATACAATCCCCCAACCCTTCTCCTACCACTCCCGTTACTTC
ACACCCAAACCTGTTCTTGACTCCACCATTGATTACTTCCAACCAAATAACAAAAGGAAT
CAGCTTTGGATGAGGCTACAAACCTCTAGAAATGTGGACCACGTAGGCCTCGGCACTGCG
TTCGAAAACAGTATATACGACCAGGACTACAATATCCGTGTAACCATGTATGTACAATTC
AGAGAATTTAATCTTAAAGACCCCCCACTTAAACCCTAAATGAATAAAAATAAAAACCAT
TACGATGTGATAACAAAAAAGACTCAGTAATTTATTTTATATGGGAAAAGGGCACAGGGT
GGGTCCACTGCTTCAAATCGGCCTTCGGGTACC
```

FIG.9

ATGACGTATCCAAGGAGGCGTTACCGCAGAAGAAGACACCGCCCCCGCAGCCATCTTGGC
CAGATCCTCCGCCGCCGCCCCTGGCTCGTCCACCCCCGCCACCGCTACCGTTGGAGAAGG
AAAAATGGCATCTTCAACACCCGCCTCTCCCGCACCTTCGGATATACTGTCAAGGCTACC
ACAGTCAGAACGCCCTCCTGGGCGGTGGACATGATGAGATTTAATATTGACGACTTTGTT
CCCCCGGGAGGGGGGACCAACAAAATCTCTATACCCTTTGAATACTACAGAATAAGAAAG
GTTAAGGTTGAATTCTGGCCCTGCTCCCCCATCACCCAGGGTGATAGGGGAGTGGGCTCC
ACTGCTGTTATTCTAGATGATAACTTTGTAACAAAGGCCACAGCCCTAACCTATGACCCA
TATGTAAACTACTCCTCCCGCCATACAATCCCCCAACCCTTCTCCTACCACTCCCGTTAC
TTCACACCCAAACCTGTTCTTGACTCCACCATTGATTACTTCCAACCAAATAACAAAAGG
AATCAGCTTTGGATGAGGCTACAAACCTCTAGAAATGTGGACCACGTAGGCCTCGGCACT
GCGTTCGAAAACAGTATATACGACCAGGACTACAATATCCGTGTAACCATGTATGTACAA
TTCAGAGAATTTAATCTTAAAGACCCCCCACTTAAACCCTAA

FIG.10

MTYPRRRYRRRRHRPRSHLGQILRRRPWLVHPRHRYRWRRKNGIFNTRLSRTFGYTVKAT
TVRTPSWAVDMMRFNIDDFVPPGGGTNKISIPFEYYRIRKVKVEFWPCSPITQGDRGVGS
TAVILDDNFVTKATALTYDPYVNYSSRHTIPQPFSYHSRYFTPKPVLDSTIDYFQPNNKR
NQLWMRLQTSRNVDHVGLGTAFENSIYDQDYNIRVTMYVQFREFNLKDPPLKP*

*translation termination codon

FIG.11

SEQUENCE LISTING

<160> NUMBER OF SEQ ID NOS: 26

<210> SEQ ID NO 1
<211> LENGTH: 1768
<212> TYPE: DNA
<213> ORGANISM: Porcine circovirus

<400> SEQUENCE: 1
aaatttctga caaacgttac agggtgctgc tctgcaacgg tcaccagact cccgctctcc      60
aacaaggtac tcacagcagt agacaggtca ctccgttgtc cttgagatcg aggagctcca     120
cattcaataa gtaagttgcc ttctttactg caatattctt tattctgctg atcagttcct     180

```
ttggctttct cgatatggca gcgggcaccc aaataccact tcactttatt aaaagtttgc    240
ttcttcacaa aattagcgaa ccctggagg tgaggtgttc gtccttcctc attaccctcc    300
tcgccaacaa taaaataatc aaataggag attgggagct cccgtatttt cttgcgctcg    360
tcttcggaag gattattcag cgtgaacacc cacctttat gtggttgggg tccgcttctt    420
ccattcttct tgctgggcat gttgctgctg aggtgctgcc gaggtgctgc cgctgccgaa    480
gtgcgctggt aatacttaca gcgcacttct ttcgttttca gctatgacgt atccaaggag    540
gcgttaccgc agaagaagac accgccccg cagccatctt ggccagatcc tccgccgccg    600
cccctggctc gtccaccccc gccaccgcta ccgttggaga aggaaaaatg gcatcttcaa    660
cacccgcctc tcccgcacct tcggatatac tgtcaaggct accacagtca gaacgccctc    720
ctgggcggtg gacatgatga gatttaatat tgacgacttt gttccccccgg gagggggggac    780 caacaaaatc tctatacccct ttgaatacta cagaataaga aaggttaagg ttgaattctg    840
gccctgctcc cccatcaccc agggtgatag gggagtgggc tccactgctg ttattctaga    900
tgataacttt gtaacaaagg ccacagccct aacctatgac ccatatgtaa actactcctc    960
ccgccataca atcccccaac ccttctccta ccactcccgt tacttcacac ccaaacctgt   1020
tcttgactcc accattgatt acttccaacc aaataacaaa aggaatcagc tttggatgag   1080
gctacaaacc tctagaaatg tggaccacgt aggcctcggc actgcgttcg aaaacagtat   1140
atacgaccag gactcaaata tccgtgtaac catgtatgta caattcagag aatttaatct   1200
taaagacccc ccacttaaac cctaaatgaa taataaaaac cattacgaag tgataaaaaa   1260
gactcagtaa tttatttcat atggaaattc agggcatggg gggaaaggg tgacgaactg   1320 gccccccttcc tccgtggatt gttctgtagc attcttccaa ataccaaga aagtaatcct   1380 ccgatagaga gcttctacag ctgggacagc agttgaggag taccattcca acggggtctg   1440
attgctggta atcagaatac tgcgggccaa aaaggtaca gttccaccctt tagtctctac   1500 agtcaatgga tatcgatcac acagtctcag tagatcatcc cacggcagcc agccataaaa   1560
gtcatcaata caaccactt cttccaccatg gtaaccatcc caccacttgt ttctaggtgg   1620
tttccagtat gtggtttccg ggtctgcaaa attagcagcc catttgctttt taccacaccc   1680 aggtggcccc acaatgacgt gtacattggt cttccaatca cgcttctgca ttttcccgct   1740
cactttcaaa agttcagcca gcccgcgg                                      1768

<210> SEQ ID NO 2
<211> LENGTH: 1773
<212> TYPE: DNA
<213> ORGANISM: Porcine circovirus

<400> SEQUENCE: 2
ggtacctccg tggattgttc tccagcagtc ttccaaaatt gcaaagtagt aatcctccga     60
tagagagctt ctacagctgg gacagcagtt gaggagtacc attcctgggg ggcctgattg    120
ctggtaatca aaatactgcg ggccaaaaaa ggaacagtac cccctttagt ctctacagtc    180
aatggatacc ggtcacacag tctcagtaga tcatcccaag gtaaccagcc ataaaaatca    240
tccaaaacaa caacttcttc tccatgatat ccatcccacc acttattcct actaggcttc    300
cagtaggtgt ccctaggctc agcaaaatta cgggcccact ggctcttccc acaaccgggc    360
gggcccacta tgacgtgtac agctgtcttc aatcacgct gctgcatctt cccgctcact    420
ttcaaaagtt cagccagccc gcggaaattt ctcacatacg ttacaggaaa ctgctcggct    480
```

-continued

| | |
|---|---|
| acagtcacca aagaccccgt ctccaaaagg gtactcacag cagtagacag gtcgctgcgc | 540 |
| ttcccctggt tccgcggagc tccacactcg ataagtatgt ggccttcttt actgcagtat | 600 |
| tctttattct gctggtcggt tcctttcgct ttctcgatgt ggcagcgggc accaaaatac | 660 |
| cacttcacct tgttaaaagt ctgcttctta gcaaaattcg caaaccctg gaggtgagga | 720 |
| gttctaccct cttccaaacc ttcctcgcca caaacaaaat aatcaaaaag ggagattgga | 780 |
| agctcccgta ttttgttttt ctcctcctcg aaggattat taagggtgaa cacccacctc | 840 |
| ttatggggtt gcgggccgct tttcttgctt ggcattttca ctgacgctgc cgaggtgctg | 900 |
| ccgctgccga agtgcgctgg taatactaca gcagcgcact tctttcactt ttataggatg | 960 |
| acgtatccaa ggaggcgtta ccgcagaaga agacaccgcc cccgcagcca tcttggccag | 1020 |
| atcctccgcc gccgccctg gctcgtccac ccccgccacc gctaccgttg gagaaggaaa | 1080 |
| aatggcatct tcaacacccg cctctcccgc accttcggat atactgtcaa ggctaccaca | 1140 |
| gtcagaacgc cctcctgggc ggtggacatg atgagattta atattgacga ctttgttccc | 1200 |
| ccggggagggg ggaccaacaa aatctctata ccctttgaat actacagaat aagaaaggtt | 1260 |
| aaggttgaat tctggccctg ctcccccatc acccagggtg ataggggagt gggctccact | 1320 |
| gctgttattc tagatgataa ctttgtaaca aaggccacag ccctaaccta tgacccatat | 1380 |
| gtaaactact cctcccgcca tacaatcccc aacccttct cctaccactc ccgttacttc | 1440 |
| acacccaaac ctgttcttga ctccaccatt gattacttcc aaccaaataa caaaaggaat | 1500 |
| cagctttgga tgaggctaca aacctctaga aatgtggacc acgtaggcct cggcactgcg | 1560 |
| ttcgaaaaca gtatatacga ccaggactac aatatccgtg taaccatgta tgtacaattc | 1620 |
| agagaattta atcttaaaga ccccccactt aaaccctaaa tgaataaaaa taaaaaccat | 1680 |
| tacgatgtga taacaaaaaa gactcagtaa tttattttat atgggaaaag ggcacagggt | 1740 |
| gggtccactg cttcaaatcg gccttcgggt acc | 1773 |

<210> SEQ ID NO 3
<211> LENGTH: 702
<212> TYPE: DNA
<213> ORGANISM: Porcine circovirus

<400> SEQUENCE: 3

| | |
|---|---|
| atgacgtatc caaggaggcg ttaccgcaga agaagacacc gccccgcag ccatcttggc | 60 |
| cagatcctcc gccgccgccc ctggctcgtc caccccgcc accgctaccg ttggagaagg | 120 |
| aaaaatggca tcttcaacac ccgcctctcc cgcaccttcg gatatactgt caaggctacc | 180 |
| acagtcagaa cgccctcctg ggcggtggac atgatgagat ttaatattga cgactttgtt | 240 |
| cccccggag gggggaccaa caaatctct ataccctttg aatactacag aataagaaag | 300 |
| gttaaggttg aattctggcc ctgctcccc atcacccagg gtgatagggg agtgggctcc | 360 |
| actgctgtta ttctagatga taactttgta acaaaggcca cagccctaac ctatgaccca | 420 |
| tatgtaaact actcctcccg ccatacaatc cccaaccct ctcctacca ctcccgttac | 480 |
| ttcacaccca aacctgttct tgactccacc attgattact ccaaccaaa taacaaaagg | 540 |
| aatcagcttt ggatgaggct acaaacctct agaaatgtgg accacgtagg cctcggcact | 600 |
| gcgttcgaaa acagtatata cgaccaggac tacaatatcc gtgtaaccat gtatgtacaa | 660 |
| ttcagagaat ttaatcttaa agacccccca cttaaaccct aa | 702 |

<210> SEQ ID NO 4
<211> LENGTH: 233

```
<212> TYPE: PRT
<213> ORGANISM: Porcine circovirus

<400> SEQUENCE: 4

Met Thr Tyr Pro Arg Arg Tyr Arg Arg Arg His Arg Pro Arg
1               5                   10                  15

Ser His Leu Gly Gln Ile Leu Arg Arg Pro Trp Leu Val His Pro
                20                  25                  30

Arg His Arg Tyr Arg Trp Arg Arg Lys Asn Gly Ile Phe Asn Thr Arg
            35                  40                  45

Leu Ser Arg Thr Phe Gly Tyr Thr Val Lys Ala Thr Thr Val Arg Thr
        50                  55                  60

Pro Ser Trp Ala Val Asp Met Met Arg Phe Asn Ile Asp Asp Phe Val
65                      70                  75                  80

Pro Pro Gly Gly Gly Thr Asn Lys Ile Ser Ile Pro Phe Glu Tyr Tyr
                    85                  90                  95

Arg Ile Arg Lys Val Lys Val Glu Phe Trp Pro Cys Ser Pro Ile Thr
                100                 105                 110

Gln Gly Asp Arg Gly Val Gly Ser Thr Ala Val Ile Leu Asp Asp Asn
                115                 120                 125

Phe Val Thr Lys Ala Thr Ala Leu Thr Tyr Asp Pro Tyr Val Asn Tyr
        130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Met Arg Leu Gln Thr Ser Arg Asn
                180                 185                 190

Val Asp His Val Gly Leu Gly Thr Ala Phe Glu Asn Ser Ile Tyr Asp
            195                 200                 205

Gln Asp Tyr Asn Ile Arg Val Thr Met Tyr Val Gln Phe Arg Glu Phe
        210                 215                 220

Asn Leu Lys Asp Pro Pro Leu Lys Pro
225                 230

<210> SEQ ID NO 5
<211> LENGTH: 30
<212> TYPE: DNA
<213> ORGANISM: Porcine circovirus

<400> SEQUENCE: 5
gaaccgcggg ctggctgaac ttttgaaagt                                     30

<210> SEQ ID NO 6
<211> LENGTH: 30
<212> TYPE: DNA
<213> ORGANISM: Porcine circovirus

<400> SEQUENCE: 6
gcaccgcgga aatttctgac aaacgttaca                                     30

<210> SEQ ID NO 7
<211> LENGTH: 21
<212> TYPE: DNA
<213> ORGANISM: Porcine circovirus

<400> SEQUENCE: 7
tttggtaccc gaaggccgat t                                              21
```

<210> SEQ ID NO 8
<211> LENGTH: 24
<212> TYPE: DNA
<213> ORGANISM: Porcine circovirus

<400> SEQUENCE: 8
attggtacct ccgtggattg ttct                                    24

<210> SEQ ID NO 9
<211> LENGTH: 39
<212> TYPE: DNA
<213> ORGANISM: Porcine circovirus

<400> SEQUENCE: 9
gaagttaacc ctaaatgaat aaaaataaaa accattacg                    39

<210> SEQ ID NO 10
<211> LENGTH: 37
<212> TYPE: DNA
<213> ORGANISM: Porcine circovirus

<400> SEQUENCE: 10
ggtggcgcct ccttggatac gtcatcctat aaaagtg                      37

<210> SEQ ID NO 11
<211> LENGTH: 30
<212> TYPE: DNA
<213> ORGANISM: Porcine circovirus

<400> SEQUENCE: 11
aggttataag tgggggtct ttaagattaa                               30

<210> SEQ ID NO 12
<211> LENGTH: 27
<212> TYPE: DNA
<213> ORGANISM: Porcine circovirus

<400> SEQUENCE: 12
ggaaacgtta ccgcagaaga agacacc                                 27

<210> SEQ ID NO 13
<211> LENGTH: 35
<212> TYPE: DNA
<213> ORGANISM: Porcine circovirus

<400> SEQUENCE: 13
actatagatc tttattcatt tagagggtct ttcag                        35

<210> SEQ ID NO 14
<211> LENGTH: 29
<212> TYPE: DNA
<213> ORGANISM: Porcine circovirus

<400> SEQUENCE: 14
tacgggcatg catgacgtgg ccaaggagg                               29

<210> SEQ ID NO 15
<211> LENGTH: 36
<212> TYPE: DNA
<213> ORGANISM: Porcine circovirus

<400> SEQUENCE: 15

-continued agacgagatc tatgaataat aaaaaccatt acgaag    36

<210> SEQ ID NO 16
<211> LENGTH: 31
<212> TYPE: DNA
<213> ORGANISM: Porcine circovirus

<400> SEQUENCE: 16
cgtaagcatg cagctgaaaa cgaaagaagt g    31

<210> SEQ ID NO 17
<211> LENGTH: 24
<212> TYPE: DNA
<213> ORGANISM: Porcine circovirus

<400> SEQUENCE: 17
gctgaacttt tgaaagtgag cggg    24

<210> SEQ ID NO 18
<211> LENGTH: 26
<212> TYPE: DNA
<213> ORGANISM: Porcine circovirus

<400> SEQUENCE: 18
tcacacagtc tcagtagatc atccca    26

<210> SEQ ID NO 19
<211> LENGTH: 21
<212> TYPE: DNA
<213> ORGANISM: Porcine circovirus

<400> SEQUENCE: 19
ccaactttgt aaccccctcc a    21

<210> SEQ ID NO 20
<211> LENGTH: 18
<212> TYPE: DNA
<213> ORGANISM: Porcine circovirus

<400> SEQUENCE: 20
gtggacccac cctgtgcc    18

<210> SEQ ID NO 21
<211> LENGTH: 20
<212> TYPE: DNA
<213> ORGANISM: Porcine circovirus

<400> SEQUENCE: 21
ccagctgtgg ctccatttaa    20

<210> SEQ ID NO 22
<211> LENGTH: 29
<212> TYPE: DNA
<213> ORGANISM: Porcine circovirus

<400> SEQUENCE: 22
ttcccatata aaataaatta ctgagtctt    29

<210> SEQ ID NO 23
<211> LENGTH: 19
<212> TYPE: DNA
<213> ORGANISM: Porcine circovirus

<400> SEQUENCE: 23

```
cagtcagaac gccctcctg                                              19

<210> SEQ ID NO 24
<211> LENGTH: 22
<212> TYPE: DNA
<213> ORGANISM: Porcine circovirus

<400> SEQUENCE: 24
cctagaaaca agtggtggga tg                                          22

<210> SEQ ID NO 25
<211> LENGTH: 19
<212> TYPE: DNA
<213> ORGANISM: Porcine circovirus

<400> SEQUENCE: 25
ttgtaacaaa ggccacagc                                              19

<210> SEQ ID NO 26
<211> LENGTH: 23
<212> TYPE: DNA
<213> ORGANISM: Porcine circovirus

<400> SEQUENCE: 26
gtgtgatcga tatccattga ctg                                         23
```

CHIMERIC INFECTIOUS DNA CLONES, CHIMERIC PORCINE CIRCOVIRUSES AND USES THEREOF

CROSS-REFERENCE TO RELATED U.S. APPLICATIONS

This continuation-in-part application claims the benefit under 35 U.S.C. § 120 of the prior, copending nonprovisional U.S. application Ser. No. 10/314,512, filed on Dec. 9, 2002, which claims the benefit under 35 U.S.C. § 119(e) of U.S. Provisional Application No. 60/424,840, filed on Nov. 8, 2002, which claims the benefit under 35 U.S.C. § 119(e) of U.S. Provisional Application No. 60/340,775, filed on Dec. 12, 2001. The three prior applications are incorporated herein by reference in their entirety.

REFERENCE TO A SEQUENCE LISTING

The material on a single compact disc containing a Sequence Listing file provided in the prior nonprovisional application is incorporated by reference. The date of creation is Jan. 22, 2003 and the size is approximately 9.5 kb.

STATEMENT REGARDING FEDERALLY SPONSORED RESEARCH OR DEVELOPMENT

This study was supported in part by a grant from the U.S. Department of Agriculture National Research Initiative Competitive Grant Program (NRI 2004-35204-14213).

BACKGROUND OF THE INVENTION

1. Field of the Invention

The present invention concerns infectious porcine circovirus type-1 (PCV1) and type-2 (PCV2) DNA clones, chimeric PCV1-2 infectious DNA clones and live chimeric viruses derived from the chimeric DNA clones, useful as vaccines. The invention further concerns two mutations in the PCV2 immunogenic capsid gene and protein, and the introduction of the ORF2 mutations in the chimeric clones.

2. Description of the Related Art

All patents and publications cited in this specification are hereby incorporated by reference in their entirety.

Porcine circovirus (PCV) was originally isolated as a noncytopathic cell culture contaminant of a porcine kidney cell line PK-15 (I. Tischer et al., "A very small porcine virus with circular single-stranded DNA," Nature 295:64-66 (1982); I. Tischer et al., "Characterization of papovavirus and picornavirus-like particles in permanent pig kidney cell lines," Zentralbl. Bakteriol. Hyg. Otg. A. 226(2):153-167 (1974)). PCV is a small icosahedral non-enveloped virus that contains a single stranded circular DNA genome of about 1.76 kb. PCV is classified in the family of Circoviridae along with other animal circoviruses such as chicken anemia virus (CAV), Psittacine beak and feather disease virus (PBFDV) and tentative members columbid circovirus (CoCV) discovered in pigeons, goose circovirus and canary circovirus, and three plant circoviruses (banana bunchy top virus, coconut foliar decay virus and subterranean clover stunt virus) (K. V. Phenix et al., "Nucleotide sequence analysis of a novel circovirus of canaries and its relationship to other members of the genus *circovirus* of the family Circoviridae," J. Gen. Virol. 82:2805-2809 (2001); Todd et al., "Genome sequence determinations and analyses of novel circoviruses from goose and pigeon," Virology 286:354-362 (2001); M. R. Bassami et al., "Psittacine beak and feather disease virus nucleotide sequence analysis and its relationship to porcine circovirus, plant circoviruses, and chicken anemia virus," Virology 249:453-459 (1998); J. Mankertz et al., "Transcription analysis of porcine circovirus (PCV)," Virus Genes 16:267-276 (1998); A. Mankertz et al., "Cloning and sequencing of columbid circovirus (CoCV), a new circovirus from pigeons," Arch. Virol. 145:2469-2479 (2000); B. M. Meehan et al., "Sequence of porcine circovirus DNA: affinities with plant circoviruses," J. Gen. Virol. 78:221-227 (1997); B. M. Meehan et al., "Characterization of novel circovirus DNAs associated with wasting syndromes in pigs," J. Gen. Virol. 79:2171-2179 (1998); D. Todd et al., "Comparison of three animal viruses with circular single-stranded DNA genomes," Arch. Virol. 117:129-135 (1991)).

Members of the three previously recognized animal circoviruses (PCV, CAV, and PBFDV) do not share nucleotide sequence homology or antigenic determinants with each other (M. R. Bassami et al., 1998, supra; D. Todd et al., 1991, supra). The genome of the newly identified CoCV shared about 40% nucleotide sequence identity with that of PCV (A. Mankertz et al., "Cloning and sequencing of columbid circovirus (CoCV), a new circovirus from pigeons," Arch. Virol. 145:2469-2479 (2000)). Recently, a novel human circovirus with a circular genome, designated as transfusion transmitted virus or TT virus (TTV), was identified from individuals associated with post-transfusion hepatitis (H. Miyata et al., "Identification of a novel GC-rich 113-nucleotide region to complete the circular, single-stranded DNA genome of TT virus, the first human circovirus," J. Virol. 73:3582-3586 (1999); T. Nishizawa et al., "A novel DNA virus (TTV) associated with elevated transaminase levels in posttransfusion hepatitis of unknown etiology," Biochem. Biophys. Res. Commun. 241:92-97 (1997)). Additionally, a human TTV-like mini virus (TLMV) was identified from normal blood donors (P. Biagini et al., "Genetic analysis of full-length genomes and subgenomic sequences of TT virus-like mini virus human isolates," J. Gen. Virol. 82: 379-383 (2001); K. Takahashi et al., "Identification of a new human DNA virus (TTV-like mini virus, TLMV) intermediately related to TT virus and chicken anemia virus," Arch. Virol. 145:979-93 (2000)) and a third novel human circovirus, known as SEN virus (SENV), was also discovered from humans with post-transfusion hepatitis (T. Umemura et al., "SEN virus infection and its relationship to transfusion-associated hepatitis," Hepathology 33:1303-1311 (2001)). The genomic organization of both human TTV and TLMV is similar to that of the CAV (P. Biagini et al., 2001, supra; H. Miyata et al., 1999, supra; K. Takahashi et al., 2000, supra). Although antibodies to PCV were found in various animal species including humans, mice, cattle and pigs (G. M. Allan et al., "Production, preliminary characterization and applications of monoclonal antibodies to porcine circovirus," Vet. Immunol. Immunopathol. 43:357-371 (1994); G. C. Dulac and A. Afshar, "Porcine circovirus antigens in PK-15 cell line (ATCC CCL-33) and evidence of antibodies to circovirus in Canadian pigs," Can. J. Vet. Res. 53:431-433 (1989); S. Edwards and J. J. Sands, "Evidence of circovirus infection in British pigs," Vet. Rec. 134:680-1 (1994); J. C. Harding and E. G. Clark, "Recognizing and diagnosing postweaning multisystemic wasting syndrome (PMWS)," Swine Health and Production 5:201-203 (1997); R. K. Hines and P. D. Lukert, "Porcine circovirus: a serological survey of swine in the United States," Swine Health and Production 3:71-73 (1995); G. P. Nayar et al., "Evidence for circovirus in cattle with respiratory disease and from aborted bovine fetuses," Can. Vet. J. 40:277-278 (1999); I.

Tischer et al., "Distribution of antibodies to porcine circovirus in swine populations of different breeding farms," Arch. Virol. 140:737-743 (1995); I. Tischer et al., "Presence of antibodies reacting with porcine circovirus in sera of humans, mice, and cattle," Arch. Virol. 140:1427-1439 (1995)), little is known regarding the pathogenesis of PCV in these animal species. Experimental infection of pigs with the PK-15 cells-derived PCV did not produce clinical disease and thus, this virus is not considered to be pathogenic to pigs (G. M. Allan et al., "Pathogenesis of porcine circovirus; experimental infections of colostrum deprived piglets and examination of pig foetal material," Vet. Microbiol. 44:49-64 (1995); I. Tischer et al., "Studies on epidemiology and pathogenicity of porcine circovirus," Arch. Virol. 91:271-276 (1986)). The nonpathogenic PCV derived from the contaminated PK-15 cell line was designated as porcine circovirus type 1 or PCV1.

Postweaning multisystemic wasting syndrome (PMWS), first described in 1991 (J. C. Harding and E. G. Clark, 1997, supra), is a complex disease of weaning piglets that is becoming increasingly more widespread. With the threat of a potential serious economic impact upon the swine industry, it has become urgent to develop a vaccine against PCV2, the primary causative agent of PMWS. PMWS mainly affects pigs between 5-18 weeks of age. Clinical PMWS signs include progressive weight loss, dyspnea, tachypnea, anemia, diarrhea, and jaundice. Mortality rate may vary from 1% to 2%, and up to 40% in some complicated cases in the U.K. (M. Muirhead, "Sources of information on PMWS/PDNS," Vet. Rec. 150:456 (2002)). Microscopic lesions characteristic of PMWS include granulomatous interstitial pneumonia, lymphadenopathy, hepatitis, and nephritis (G. M. Allan and J. A. Ellis, "Porcine circoviruses: a review," J. Vet. Diagn. Invest. 12:3-14 (2000); J. C. Harding and E. G. Clark, 1997, supra). PMWS has now been recognized in pigs in Canada, the United States (G. M. Allan et al., "Novel porcine circoviruses from pigs with wasting disease syndromes," Vet. Rec. 142:467-468 (1998); G. M. Allan et al., "Isolation of porcine circovirus-like viruses from pigs with a wasting disease in the USA and Europe," J. Vet. Diagn. Invest. 10:3-10 (1998); G. M. Allan and J. A. Ellis, 2000, supra; J. Ellis et al., "Isolation of circovirus from lesions of pigs with postweaning multisystemic wasting syndrome," Can. Vet. J. 39:44-51 (1998); A. L. Hamel et al., "Nucleotide sequence of porcine circovirus associated with postweaning multisystemic wasting syndrome in pigs," J. Virol. 72:5262-5267 (1998); M. Kiupel et al., "Circovirus-like viral associated disease in weaned pigs in Indiana," Vet. Pathol. 35:303-307 (1998); R. Larochelle et al., "Identification and incidence of porcine circovirus in routine field cases in Quebec as determined by PCR," Vet. Rec. 145:140-142 (1999); B. M. Meehan et al., 1998, supra; I. Morozov et al., "Detection of a novel strain of porcine circovirus in pigs with postweaning multisystemic wasting syndrome," J. Clin. Microbiol. 36:2535-2541 (1998)), most European countries (G. M. Allan et al., "Isolation of porcine circovirus-like viruses from pigs with a wasting disease in the USA and Europe," J. Vet. Diagn. Invest. 10:3-10 (1998); G. M. Allan and J. A. Ellis, 2000, supra; S. Edwards and J. J. Sands, 1994, supra; S. Kennedy et al., "Porcine circovirus infection in Northern Ireland," Vet. Rec. 142:495-496 (1998); A. Mankertz et al., "Characterization of PCV-2 isolates from Spain, Germany and France," Virus Res. 66:65-77 (2000); C. Rosell et al., "Identification of porcine circovirus in tissues of pigs with porcine dermatitis and nephropathy syndrome. Vet. Rec. 146:40-43 (2000); P. Spillane et al., "Porcine circovirus infection in the Republic of Ireland," Vet. Rec. 143:511-512 (1998); G. J. Wellenberg et al., "Isolation and characterization of porcine circovirus type 2 from pigs showing signs of post-weaning multisystemic wasting syndrome in the Netherlands," Vet. Quart. 22:167-72 (2000)) and some countries in Asia (C. Choi et al., "Porcine postweaning multisystemic wasting syndrome in Korean pig: detection of porcine circovirus 2 infection by immunohistochemistry and polymerase chain reaction," J. Vet. Diagn. Invest. 12:151-153 (2000); A. Onuki et al., "Detection of porcine circovirus from lesions of a pig with wasting disease in Japan," J. Vet. Med. Sci. 61:1119-1123 (1999)). PMWS potentially has a serious economic impact on the swine industry worldwide.

The primary causative agent of PMWS is a pathogenic strain of PCV designated as porcine circovirus type 2 or PCV2 (G. M. Allan et al., "Novel porcine circoviruses from pigs with wasting disease syndromes," Vet. Rec. 142:467-468 (1998); G. M. Allan et al., "Isolation of porcine circovirus-like viruses from pigs with a wasting disease in the USA and Europe," J. Vet. Diagn. Invest. 10:3-10 (1998); G. M. Allan et al., "Isolation and characterisation of circoviruses from pigs with wasting syndromes in Spain, Denmark and Northern Ireland," Vet. Microbiol. 66:115-23 (1999); G. M. Allan and J. A. Ellis, 2000, supra; J. Ellis et al., 1998, supra; A. L. Hamel et al., 1998, supra; B. M. Meehan et al., 1998, supra; I. Morozov et al., 1998, supra). The complete genomic sequence of the PMWS-associated PCV2 and nonpathogenic PCV1 have been determined (R. Larochelle et al., "Genetic characterization and phylogenetic analysis of porcine circovirus type 2 (PCV2) strains from cases presenting various clinical conditions," Virus Res. 90:101-112 (2002); M. Fenaux et al., "Genetic characterization of type 2 porcine circovirus (PCV-2) from pigs with postweaning multisystemic wasting syndrome in different geographic regions of North America and development of a differential PCR-restriction fragment length polymorphism assay to detect and differentiate between infections with PCV-1 and PCV-2," J. Clin. Microbiol. 38:2494-503 (2000); A. L. Hamel et al., 1998, supra; J. Mankertz et al., 1998, supra; B. M. Meehan et al., 1997, supra; B. M. Meehan et al., 1998, supra; I. Morozov et al., 1998, supra).

PCV1 is ubiquitous in pigs but is not pathogenic to pigs. In contrast, the genetically related PCV2 is pathogenic and causes PMWS in pigs. Sequence analyses reveals that the PMWS-associated PCV2 typically shares only about 75% nucleotide sequence identity with the nonpathogenic PCV1. Some other strains may vary somewhat to about 74% to about 76% nucleotide sequence identity. Both PCV1 and PCV2 have a very similar genomic organization and are small, non-enveloped viruses with a single stranded circular DNA genome of about 1.76 kb. The PCV genome contains at least two functional open reading frames (ORFs): ORF1 (930 bp) encodes the Rep proteins involved in viral replication (A. K. Cheung, "Transcriptional analysis of porcine circovirus," Virology 305: 168-180 (2003)) and ORF2 (699 bp) encodes the major immunogenic viral capsid protein (A. K. Cheung, 2003, supra; P. Nawagitgul et al., "Modified indirect porcine circovirus (PCV) type 2-based and recombinant capsid protein (ORF2)-based ELISA for the detection of antibodies to PCV," Immunol. Clin. Diagn. Lab Immunol. 9(1):33-40 (January 2002); P. Nawagitgul et al., "Open reading frame 2 of porcine circovirus type 2 encodes a major capsid protein," J. Gen. Virol. 81:2281-2287 (2000)).

Initial attempts to reproduce clinical PMWS in conventional pigs by PCV2 inoculation were unsuccessful (M. Balasch et al., "Experimental inoculation of conventional pigs with tissue homogenates from pigs with post-weaning multisystemic wasting syndrome," J. Comp. Pathol. 121: 139-148 (1999); M. Fenaux et al., "Cloned Genomic DNA of Type 2 Porcine Circovirus (PCV-2) Is Infectious When Injected Directly into the Liver and Lymph Nodes of SPF Pigs: Characterization of Clinical Disease, Virus Distribution, and Pathologic Lesions," J. Virol. 76:541-551 (2002)). Experimental reproduction of clinical PMWS in gnotobiotic pigs and conventional pigs with tissue homogenates from pigs with naturally occurring PMWS and with cell culture propagated PCV2 produced mixed results. Clinical PMWS was reproduced in gnotobiotic (SPF) pigs and colostrum-deprived and caesarian-derived pigs co-infected with PCV2 and porcine parvovirus (PPV) (G. M. Allan et al., "Experimental reproduction of severe wasting disease by co-infection of pigs with porcine circovirus and porcine parvovirus," J. Comp. Pathol. 121:1-11 (1999); S. Krakowka et al., "Viral wasting syndrome of swine: experimental reproduction of postweaning multisystemic wasting syndrome in gnotobiotic swine by coinfection with porcine circovirus 2 and porcine parvovirus," Vet. Pathol. 37:254-263 (2000)), and in PCV2-inoculated gnotobiotic pigs when their immune system was activated by keyhole hemocyanin in incomplete Freund's adjuvant (S. Krakowka et al., "Activation of the immune system is the pivotal event in the production of wasting disease in pigs infected with porcine circovirus-2 (PCV-2)," Vet. Pathol. 38:31-42 (2001)).

Clinical PMWS was also reproduced in cesarean derived/colostrum deprived pigs (CD/CD) inoculated with PCV2 alone (P. A. Harms et al., "Experimental reproduction of severe disease in CD/CD pigs concurrently infected with type 2 porcine circovirus and porcine reproductive and respiratory syndrome virus," Vet. Pathol. 38:528-539 (2001)) and in conventional pigs co-infected with PCV2 and either porcine parvovirus (PPV) or porcine reproductive and respiratory syndrome virus (PRRSV) (A. Rivora et al., "Experimental inoculation of conventional pigs with porcine reproductive and respiratory syndrome virus and porcine circovirus 2," J. Virol. 76: 3232-3239 (2002)). In cases of the PRRSV/PCV2 co-infection, the PMWS characteristic pathological signs such as lymphoid depletion, granulomatous inflammation and necrotizing hepatitis are induced by PCV2 and not by PRRSV (P. A. Harms et al., 2001, supra). However, clinical PMWS was not reproduced in gnotobiotic pigs infected with PCV2 alone (G. M. Allan et al., "Experimental infection of colostrums deprived piglets with porcine circovirus 2 (PCV2) and porcine reproductive and respiratory syndrome virus (PRRSV) potentiates PCV2 replication," Arch. Virol. 145:2421-2429 (2000); G. M. Allan et al., "A sequential study of experimental infection of pigs with porcine circovirus and porcine parvovirus: immunostaining of cryostat sections and virus isolation, J. Vet. Med. 47:81-94 (2000); G. M. Allan et al., "Experimental reproduction of severe wasting disease by co-infection of pigs with porcine circovirus and porcine parvovirus," J. Comp. Pathol. 121: 1-11 (1999); M. Balasch et al., 1999, supra; J. Ellis et al., "Reproduction of lesions of postweaning multisystemic wasting syndrome in gnotobiotic piglets," J. Vet. Diagn. Invest. 11:3-14 (1999); S. Kennedy et al., "Reproduction of lesions of postweaning multisystemic wasting syndrome by infection of conventional pigs with porcine circovirus type 2 alone or in combination with porcine parvovirus" J. Comp. Pathol. 122:9-24 (2000); S. Krakowka et al., 2001, supra; S. Krakowka et al., 2000, supra; R. M. Pogranichnyy et al., "Characterization of immune response of young pigs to porcine circovirus type 2 infection," Viral. Immunol. 13:143-153 (2000)). The virus inocula used in these studies were either homogenates of tissues from pigs with naturally occurring PMWS, or virus propagated in PK-15 cell cultures (G. M. Allan et al., "Experimental infection of colostrums deprived piglets with porcine circovirus 2 (PCV2) and porcine reproductive and respiratory syndrome virus (PRRSV) potentiates PCV2 replication," Arch. Virol. 145: 2421-2429 (2000); G. M. Allan et al., "A sequential study of experimental infection of pigs with porcine circovirus and porcine parvovirus: immunostaining of cryostat sections and virus isolation, J. Vet. Med. 47:81-94 (2000); G. M. Allan et al., "Experimental reproduction of severe wasting disease by co-infection of pigs with porcine circovirus and porcine parvovirus," J. Comp. Pathol. 121:1-11 (1999); M. Balasch et al., 1999, supra; J. Ellis et al., 1999, supra; S. Kennedy et al., 2000, supra; S. Krakowka et al., 2001, supra; S. Krakowka et al., 2000, supra; R. M. Pogranichnyy et al., 2000, supra). Since tissue homogenates may contain other common swine agents such as PPV and porcine reproductive and respiratory syndrome virus (PRRSV) (G. M. Allan et al., "Experimental infection of colostrums deprived piglets with porcine circovirus 2 (PCV2) and porcine reproductive and respiratory syndrome virus (PRRSV) potentiates PCV2 replication," Arch. Virol. 145:2421-2429 (2000); G. M. Allan et al., "Experimental reproduction of severe wasting disease by co-infection of pigs with porcine circovirus and porcine parvovirus," J. Comp. Pathol. 121:1-11 (1999); G. M. Allan and J. A. Ellis, 2000, supra; J. A. Ellis et al., "Coinfection by porcine circoviruses and porcine parvovirus in pigs with naturally acquired postweaning multisystemic wasting syndrome," J. Vet. Diagn. Invest. 12:21-27 (2000); C. Rosell et al., 2000, supra), and since the ATCC PK-15 cell line used for PCV2 propagation was persistently infected with PCV1 (G. C. Dulac and A. Afshar, 1989, supra), the clinical disease and pathological lesions reproduced in those studies may not be solely attributable to PCV2 infection (G. M. Allan et al., "Experimental infection of colostrums deprived piglets with porcine circovirus 2 (PCV2) and porcine reproductive and respiratory syndrome virus (PRRSV) potentiates PCV2 replication," Arch. Virol. 145:2421-2429 (2000); G. M. Allan et al., "A sequential study of experimental infection of pigs with porcine circovirus and porcine parvovirus: immunostaining of cryostat sections and virus isolation, J. Vet. Med. 47:81-94 (2000); G. M. Allan et al., "Experimental reproduction of severe wasting disease by co-infection of pigs with porcine circovirus and porcine parvovirus," J. Comp. Pathol. 121:1-11 (1999); G. M. Allan and J. A. Ellis, 2000, supra; J. A. Ellis et al., 2000, supra).

Clinical PMWS has also been reproduced in PCV2-inoculated CDCD pigs when vaccinated with *Mycoplasma hyopneumoniae* (G. M. Allan et al., "Immunostimulation, PCV-2 and PMWS," Vet. Rec. 147:171-172 (2000)). Two recent field studies by G. M. Allan et al., "Neonatal vaccination for *Mycoplasma hyopneumoniae* and postweaning multisystemic wasting syndrome: a field trial," Pig J. 48:34-41 (2001), and S. C. Kyriakis et al., "The effects of immunomodulation on the clinical and pathological expression of postweaning multisystemic wasting syndrome," J. Comp. Pathol. 126:38-46 (2002), tested the effect of immunomodulation by Mycoplasma hyopneumoniae vaccine on the development of PMWS in endemic herds, and showed a significant decrease in PMWS cases in unvaccinated groups compared to the vaccinated animals. However, another recent study using conventional SPF piglets under controlled laboratory conditions could not reproduce such an effect, suggesting that vaccinations with M. hyopneumoniae may potentially influence the development of clinical PMWS but it is clearly a secondary role to a PCV2 infection.

Based on these and other studies, PCV2 is nevertheless considered to be the primary but not the exclusive causative agent of PMWS.

The lack of an infectious virus stock of a biologically pure form of PCV2 has impeded the understanding of PCV2 pathogenesis and the etiological role of PCV2 in PMWS. Vaccinations against PPV and possibly PRRSV have not consistently been shown to prevent the onset of PMWS in PCV2 infected pigs. Consequently, finding a safe yet potent vaccine that specifically targets PMWS has been difficult. There is a definite art-recognized need in the veterinary field to produce an efficacious, safe vaccine against PCV2 infections and PMWS.

U.S. Pat. No. 6,287,856 (Poet et al.) and WO 99/45956 concern nucleic acids from psittacine beak and feather disease virus (BFDV), a circovirus that infects avian species, and from porcine circovirus (PCV). The patent proposes vaccine compositions comprising naked DNA or mRNA and discloses a nucleic acid vector for the transient expression of PCV in a eukaryotic cell comprising a cis-acting transcription or translation regulatory sequence derived from the human cytomegalovirus immediate or early gene enhancer or promoter functionally linked to a nucleic acid of the sequence. However, since the PCV DNA is derived solely from the PK-15 cell line, it is likely to comprise the nonpathogenic PCV1 discovered nearly 30 years ago by I. Tischer et al., 1974, supra, and, therefore, it is not likely to be effective in eliciting an immune reaction to PCV2 or infections caused by PCV2. Subunit vaccines of recombinant proteins made from vectors comprising open reading frames are also suggested in the patent but the open reading frames from PCV are not well characterized or distinguished from each other. Since the source of the PCV DNA is PK-15 cells, the proteins made from those vectors comprising the open reading frames of PCV1 would not possess reliable immunogenic properties, if any, against PCV2.

U.S. Pat. No. 6,217,883 (Allan et al.) and French Patent No. 2,781,159B relate to the isolation of five PCV strains from pulmonary or ganglionic samples taken from pigs infected with PMWS in Canada, California and France (Brittany), and their use in combination with at least one porcine parvovirus antigen in immunogenic compositions. Proteins encoded by PCV2 open reading frames (ORF) consisting of ORF1 to ORF13 are broadly described in the patent but there is no exemplification of any specific protein exhibiting immunogenic properties. The patent further discloses vectors consisting of DNA plasmids, linear DNA molecules and recombinant viruses that contain and express in vivo a nucleic acid molecule encoding the PCV antigen. Several other references, for example, U.S. Pat. No. 6,391,314 B1; U.S. Pat. No. 6,368,601 B1; French Patent No. 2,769,321; French Patent No. 2,769,322; WO 01/96377 A2; WO 00/01409; WO 99/18214; WO 00/77216 A2; WO 01/16330 A2; WO 99/29871; etc., also describe the administration of PCV1 or PCV2 polypeptides or the nucleic acids encoding the polypeptides of various strains.

However, the nonpathogenic PCV1 will not be useful against PCV2 infections and the pathogenic PCV2 strains described in the art, even if attenuated, are likely to be of limited value due to the usual tendency of a live virus to revert to its virulent state. Therefore, there is still a long-standing need in the art for a live, infectious, nonpathogenic antigen for the inoculation of pigs against serious infection or PMWS caused by PCV2 that is efficacious and remains safe in veterinary vaccines. These goals are met by the construction of the new live chimeric porcine circovirus described herein, which is based upon the genomic backbone of the nonpathogenic PCV1 isolated by I. Tischer et al. almost 30 years ago. The novel chimeric porcine circovirus of the present invention is able to satisfy that long-standing need by uniquely and advantageously retaining the nonpathogenic phenotype of PCV1 but eliciting specific immune response against pathogenic PCV2.

PCV2 causes pathological lesions characteristic of PMWS in specific-pathogen-free (SPF) pigs whereas PCV1 does not (M. Fenaux et al., 2002, supra). Based on the current studies, it is also observed that cell culture-derived PCV1 replicates more efficiently in PK-15 cells than PCV2 (see also M. Fenaux et al., "Immunogenicity and pathogenicity of the chimeric infectious DNA clones between pathogenic type 2 porcine circovirus (PCV2) and non-pathogenic PCV1 in weaning pigs," J. Virol. 77:11232-11243 (2003)). However, the genetic determinants for PCV2 pathogenicity in pigs and for the enhanced growth ability of PCV1 in PK-15 cells are not known. Thus, another set of objectives of the present invention is to identify and characterize the genetic determinants for PCV2 pathogenicity in vivo and for replication in vitro.

BRIEF SUMMARY OF THE INVENTION

The present invention concerns infectious chimeric DNA clones of porcine circovirus (PCV) and live chimeric viruses derived from the DNA clones that are useful as vaccines. The new live chimeric, genetically avirulent viruses are made from the nonpathogenic PCV1 genomic structure in which an immunogenic gene of a pathogenic PCV2 strain replaces a gene of the PCV1, typically in the same corresponding position. The invention encompasses the biologically functional plasmids, viral vectors and the like that contain the new recombinant nucleic acid molecules described herein, suitable host cells transfected by the vectors comprising the DNA and the immunogenic polypeptide expression products. Included within the scope of the present invention is a novel method of protecting pigs against viral infection or postweaning multisystemic wasting syndrome (PMWS) caused by PCV2 comprising administering to a pig in need of such protection an immunologically effective amount of a vaccine comprising, for example, the cloned chimeric DNA in a plasmid, a chimeric virus derived from the chimeric DNA clone, the polypeptide products expressed from the DNA described herein, etc. A further embodiment of the invention is drawn to novel mutants of the PCV2 immunogenic capsid gene and protein, and the introduction of the mutations in the chimeric clones to facilitate cell culture growth and ensure vaccine safety. The invention also provides new infectious PCV2 molecular DNA and reciprocal chimeric DNA clones of PCV that find use as experimental models in obtaining or characterizing the novel avirulent viral vaccines.

BRIEF DESCRIPTION OF THE DRAWINGS

The background of the invention and its departure from the art will be further described hereinbelow with reference to the accompanying drawings, wherein:

FIG. 1 represents the construction of an infectious PCV2 molecular DNA clone. The relative positions of the primer pair used to amplify the complete PCV2 genome are indicated by the arrows (reverse primer PCVSAC2, forward primer PCVSAC2). The PCV2 genomic DNA amplified by PCR is digested with SacII restriction enzyme, and purified. The purified and SacII-digested genomic DNA is ligated to form concatemers. Ligated concatemers are separated by gel electrophoresis, the tandem genome dimer of PCV2 is purified and cloned into pSK vector that is pre-digested with SacII enzyme to produce a molecular PCV2 DNA clone.

FIG. 2A shows the detection of PCV2 antigen by immunofluorescence assay (IFA) in PK-15 cells transfected with the cloned PCV2 plasmid DNA. Intense immunolabeling of PCV2 antigen is visualized in the nucleus, and to a lesser degree, cytoplasm of the transfected cells. FIG. 2B shows mock-transfected PK-15 cells.

FIG. 4A shows a normal lymph node from a control pig. Note the well-defined lymphoid follicles (arrows) (25×). FIG. 4B represents a microscopic section of the tracheobronchial lymph node from the pig in FIG. 3A inoculated 21 days previously by intralymphoid route with cloned PCV2 genomic DNA. Lymphoid follicles are poorly defined, there is mild-to-moderate lymphoid depletion, and mild multifocal granulomatous inflammation (25×). FIG. 4C represents a microscopic section of the lymph node in FIG. 4B in a larger magnification focusing on one follicle. Note the poorly defined follicle with macrophages and giant cells (arrow) replacing follicular lymphocytes (64×). FIG. 4D illustrates the immunohistochemical detection of PCV2 antigen in the same lymph node as FIG. 4B in macrophages (arrows) and giant cells (small arrowheads), and dendritic-like cells (large arrowheads) in the follicles (64×).

FIG. 8 represents the full-length DNA sequence of the cloned PCV2 molecular DNA (which corresponds to SEQ ID NO:1).

FIG. 9 represents the full-length DNA sequence of the cloned chimeric PCV1-2 DNA (which corresponds to SEQ ID NO:2).

FIG. 10 represents the 702 bp (699 bp sequence plus the 3 nucleotide stop codon) DNA sequence of the immunogenic ORF2 capsid gene of the cloned chimeric PCV1-2 DNA (which corresponds to SEQ ID NO:3).

FIG. 11 represents the putative amino acid translation of the immunogenic ORF2 capsid gene of the chimeric PCV1-2 DNA (which corresponds to SEQ ID NO:4).

DETAILED DESCRIPTION OF THE INVENTION

Figure 2A:
FIGS. 2A and 2B illustrate that the cloned PCV2 plasmid DNA is infectious when transfected in vitro in PK-15 cells.

In accordance with the present invention, there are provided infectious molecular and chimeric nucleic acid molecules of porcine circovirus (PCV), live chimeric viruses produced from the chimeric nucleic acid molecule and veterinary vaccines to protect pigs from viral infection or postweaning multisystemic wasting syndrome (PMWS) caused by PCV2. The invention further provides immunogenic polypeptide expression products that may be used as vaccines. Also described are two novel nucleotide mutations of the PCV2 immunogenic capsid gene resulting in two novel amino acid mutations of the PCV2 immunogenic capsid protein that are shown to be responsible for increased growth rate in vitro and attenuation of virulence in vivo, and therefore find beneficial use in the chimeric nucleic acid molecule of this invention.

The new avirulent, infectious chimeric DNA molecule of PCV (PCV1-2) comprises a nucleic acid molecule encoding an infectious, nonpathogenic PCV1 that contains an immunogenic open reading frame (ORF) gene of a pathogenic PCV2 in place of an ORF gene in the PCV1 genome. The infectious chimeric PCV1-2 DNA clone preferably contains the immunogenic capsid gene (ORF2) of the PCV2 DNA cloned in the genomic backbone of the infectious, nonpathogenic PCV1 DNA clone. Generally, the capsid gene of the PCV2 DNA replaces the ORF2 gene of the PCV1 DNA in the nonpathogenic PCV1 genomic structure but it is contemplated that a variety of positional permutations may be constructed through genetic engineering to obtain other avirulent or attenuated chimeric DNA clones. The reciprocal chimeric infectious PCV2-1 DNA clone between PCV1 and PCV2 is disclosed as a control to analyze the chimeric PCV1-2 clone of the invention and is constructed by replacing the capsid gene of PCV2 with that of PCV1 in the backbone of the pathogenic PCV2 infectious DNA clone. In addition to being an experimental model, the reciprocal chimeric PCV2-1 DNA clone may find use in making specially tailored vaccines.

The cloned genomic DNA of PCV2 described herein is shown to be in vitro and in vivo infectious when transfected into PK-15 cells and given to pigs. The infectious PCV2 DNA clone produces pathological lesions characteristic of PMWS in pigs allowing for an improved characterization of clinical disease and understanding of virus distribution in the tissue cells. This new, readily reproducible pathogenic agent lends itself to the development of a suitable vaccination program to prevent PMWS in pigs.

The novel chimeric PCV1-2 DNA clone is also infectious by both in vitro transfection of PK-15 cells and in vivo administration to pigs. In transfected PK-15 cells, the chimeric PCV1-2 DNA clone expresses the PCV2 capsid antigen (the immunogenic capsid protein of PCV2) whereas the reciprocal chimeric PCV2-1 DNA clone expresses the PCV1 capsid antigen, which is demonstrated by immunofluorescence assay (IFA) using antibodies specific to PCV1 or PCV2 capsid antigen. Seroconversion to PCV2-specific antibody is detected in pigs inoculated with the infectious PCV2 clone as well as the chimeric PCV1-2 clone. Detecting the seroconversion to PCV2-specific antibody establishes that the chimeric PCV1-2 DNA clone induces the PCV2-specific antibody in infected pigs and, consequently, acts to protect inoculated pigs from infection with PCV2.

The below examples describe the evaluation of the immunogenicity and pathogenicity of the chimeric DNA clones in inoculated pigs in more detail. Basically, seroconversions to antibodies against PCV2 ORF2 antigen are detected in pigs inoculated with the PCV2 DNA clone (Group 3) and the chimeric PCV1-2 DNA clone (Group 4). All of the pigs inoculated with the PCV1 clone and the reciprocal chimeric PCV2-1 DNA clone (Groups 2 and 5, respectively) seroconvert to the PCV1 antibody. The viruses recovered from selected pigs in each group are partially sequenced and confirmed to be the authentic respective infectious DNA clones used in the inoculation. Gross and microscopic lesions in various tissues of animals inoculated with the PCV2 DNA clone are significantly more severe than those found in pigs inoculated with PCV1, chimeric PCV1-2 and reciprocal chimeric PCV2-1 DNA clones.

Surprisingly and advantageously, the chimeric PCV1-2 infectious DNA clone having the immunogenic capsid gene (ORF2) of the pathogenic PCV2 cloned into the nonpathogenic PCV1 genomic backbone induces a specific antibody response to the pathogenic PCV2 capsid antigen while it uniquely retains the nonpathogenic nature of PCV1 in pigs. Animals inoculated with the chimeric PCV1-2 infectious DNA clone develop a mild infection resembling that of PCV1 inoculated animals while seroconverting to the antibody against the ORF2 capsid protein of the pathogenic PCV2. The average length of viremia observed in PCV1 and chimeric PCV1-2 inoculated animals is shorter, 0.625 weeks and 1 week respectively, than that in pathogenic PCV2 inoculated animals which is about 2.12 weeks. The lack of detectable chimeric PCV1-2 viremia in some inoculated animals does not affect seroconversion to antibody against PCV2 ORF2 capsid protein in the PCV1-2 inoculated pigs (Group 4). The results indicate that, even though the chimeric PCV1-2 viremia is short or undetectable in some inoculated animals, the chimeric PCV1-2 virus is able to induce antibody response against PCV2 ORF2 capsid protein. The special ability of the chimeric PCV1-2 infectious DNA clone to induce the immune response specific to the pathogenic PCV2 immunogenic ORF2 capsid protein yet remain nonpathogenic to pigs makes the chimeric PCV1-2 clone particularly useful as a genetically engineered live-attenuated vaccine and other types of vaccines.

The novel, purified and isolated nucleic acid molecules of this invention comprise the full-length DNA sequence of the cloned chimeric PCV1-2 DNA set forth in SEQ ID NO:2, shown in FIG. 9 and deposited in the American Type Culture Collection under Patent Deposit Designation PTA-3912; its complementary strand (i.e., reverse and opposite base pairs) or the nucleotide sequences having at least 95% homology to the chimeric nucleotide sequence (i.e., a significant active portion of the whole gene). Conventional methods that are well known in the art can be used to make the complementary strands or the nucleotide sequences possessing high homology, for instance, by the art-recognized standard or high stringency hybridization techniques. The purified and isolated nucleic acid molecule comprising the DNA sequence of the immunogenic capsid gene of the cloned chimeric PCV1-2 DNA is also set forth in SEQ ID NO:3 and FIG. 10.

Suitable cells containing the chimeric nucleic acid molecule uniquely produce live, infectious chimeric porcine circoviruses. The live, infectious chimeric virus is derived from the chimeric DNA clone by transfecting PK-15 cells via in vitro and in vivo transfections as illustrated herein. A preferred example of the cloned chimeric PCV1-2 DNA is the nucleotide sequence set forth in SEQ ID NO:2 and FIG. 9. The invention further envisions that the chimeric virus is derived from the complementary strand or the nucleotide sequences having a high homology, at least 95% homology, to the chimeric nucleotide sequence.

Also included within the scope of the present invention are biologically functional plasmids, viral vectors and the like that contain the new recombinant nucleic acid molecules described herein, suitable host cells transfected by the vectors comprising the chimeric and molecular DNA clones and the immunogenic polypeptide expression products. A particularly preferred immunogenic protein has the amino acid sequence set forth in SEQ ID NO:4 and FIG. 11. The biologically active variants thereof are further encompassed by the invention. One of ordinary skill in the art would know how to modify, substitute, delete, etc., amino acid(s) from the polypeptide sequence and produce biologically active variants that retain the same, or substantially the same, activity as the parent sequence without undue effort.

To produce the immunogenic polypeptide products of this invention, the process may include the following steps: growing, under suitable nutrient conditions, prokaryotic or eucaryotic host cells transfected with the new recombinant nucleic acid molecules described herein in a manner allowing expression of said polypeptide products, and isolating the desired polypeptide products of the expression of said nucleic acid molecules by standard methods known in the art. It is contemplated that the immunogenic proteins may be prepared by other techniques such as, for example, biochemical synthesis and the like.

Another embodiment of the present invention relates to novel mutations of the nucleotide and amino acid sequences of the PCV2 immunogenic capsid gene and protein. PCV2 is the primary causative agent of postweaning multisystemic wasting syndrome (PMWS), whereas the PK-15 cell culture-derived porcine circovirus type 1 (PCV1) is nonpathogenic to pigs. The molecular mechanisms of PCV2 replication and pathogenesis have been poorly understood. As fully described herein, the important identification and isolation of two amino acid mutations within the PCV2 capsid protein that are vital for PCV2 pathogenicity in vivo and improved growth ability in PK-15 cells provides a viable mechanism by which the chimeric PCV1-2 vaccine of the present invention can grow better in cell cultures or be made safer in vaccinations.

To identify genetic determinants for virulence and replication, a pathogenic PCV2 isolate is serially passaged for 120 times in PK-15 cells, and the viruses that are harvested from passages 1 (VP1) and 120 (VP120) are biologically, genetically and experimentally characterized. A one-step growth curve is used to compare the growth characteristics of PCV1, PCV2 VP1, and PCV2 VP120. The results show that the PCV2 VP120 virus replicates to a similar titer as PCV1 but more efficiently than PCV2 VP1 in PK-15 cells with at least 1 log difference. The complete genomic sequences of viruses at passages 0, 30, 60, 90, and 120 are determined. Two novel amino acid mutations are identified in the capsid gene after 120 passages, and it is shown that these two mutations are responsible for the increased growth rate in vitro and the attenuation of virulence in vivo. There are only two nucleotide differences as well, cytosine to guanine (C to G) and adenine to cytosine (A to C), both of which are non-silent mutations that result in the two amino acid changes. The first mutation occurs at passage 30, in which a proline at position 110 of the capsid protein is substituted for an alanine (P110A), and this mutation remains in the subsequent passages. In position 328 of the nucleotide sequence, cytosine changes to guanine (C to G) leading to this amino acid change of P110A. The second mutation, a substitution of an arginine for a serine at position 191 of the capsid protein (R191S), appears at passage 120 but not in earlier passages. In nucleotide position 573, adenine changes to cytosine (A to C) leading to this second amino acid change of R191S.

To characterize the pathogenicity of the VP120 virus, 31 specific-pathogen-free (SPF) pigs are randomly divided into three groups. Ten pigs in Group 1 receive phosphate buffered saline as negative controls. Eleven Group 2 pigs are inoculated intramuscularly and intranasally with $10^{4.9}TCID_{50}$ of PCV2 VP120. Ten pigs in Group 3 are inoculated with $10^{4.9}TCID_{50}$ of PCV2 VP1. PCV2 viremia is detected in 9/10 pigs in the PCV2 VP1 group, but only in 4/11 pigs in PCV120 group. The viremia in VP1 group (mean 3 weeks) lasts longer than that of VP120 group (mean 1.6 weeks). In addition, the PCV2 genomic copy loads in serum, as determined by quantitative real-time PCR, in the PCV2 VP1 group are higher than those in PCV2 VP120 group (p<0.0001). Gross and histopathologic lesions found in pigs inoculated with PCV2 VP1 are more severe than those inoculated with PCV2 VP120 at both 21 and 42 DPI necropsies (p=0.0032 and p=0.0274, respectively). Taken together, the results demonstrate that the P110A and R191S mutations in the capsid of PCV2 enhance the growth ability of PCV2 in vitro and attenuate the virus in vivo.

As a result of the P110A and R191S mutations in the capsid protein, PCV2 VP 120 replicates more efficiently (p=0.0053) in PK-15 cells with at least 1 log difference in infectious titer compared to the passage 1 virus. PCV2 VP120 replicates to a similar level with the PK-15 cell culture-adapted PCV1, and thus these two mutations either alone or collectively are responsible for the enhanced growth of PCV2 VP120 in vitro. Allan et al. (G. M. Allan et al., 1994, supra) attempted to infect human Vero cells with PCV1. Intranuclear immune staining, characteristic of PCV1 replication, was not detected until the $6^{th}$ cell culture passage in Vero cells. By passage 15, PCV1 replicated in Vero cells similarly to PK-15 cells. However, it has not been previously reported in the literature that 120 passages of the PCV2 in the PK-15 cell line will result in significantly improved replication efficiency to mimic the PK-15 cell culture-adapted PCV1.

Surprisingly, when SPF piglets are inoculated with the PCV2 VP120, fewer pigs develop viremia with shorter duration and lower PCV2 genomic copy loads compared to PCV2 VP1 inoculated pigs. It is shown that the nonpathogenic PK-15 cell-adapted PCV1 has a short average viremia length of 0.625 weeks in infected pigs. Analyses of the gross, microscopic and IHC mean scores reveal that the PCV2 VP120 virus inoculated pigs have milder pathological lesions and clinical signs than the PCV2 VP1 virus inoculated pigs. Taken together, the results from this invention show that PCV2 VP 120 has advantageously been adapted to grow better in PK-15 cells and is attenuated in pathogenicity in vivo.

After 120 passages in PK-15 cells, only two amino acid mutations are detected in the entire PCV2 genome, suggesting that the PCV2 genome is relatively stable. This may explain why the sequences of all known PCV2 field isolates identified to date are very conserved (M. Fenaux et al., 2002, supra; R. Larochelle et al., 2002, supra). The P110A mutation surprisingly occurs early (passage 30) during the serial passage, and involves two hydrophobic amino acids, proline and alanine. The change from proline to alanine may alter the tertiary structure of the capsid protein as proline is often involved in the bending regions of protein structures. This P110A mutation is then retained in the subsequent higher passages including passage 120. The uniqueness of the retained P110A mutation through passage 120 compared to the sequences of known PCV1 and PCV2 field isolates strongly correlates the mutation with a biological role. The R191S mutation occurs very late during the serial passage (between passages 90 and 120), and is also unique to the VP120 as the known PCV2 and PCV1 isolates do not have a serine residue at this position. Only glycine, alanine and threonine substitutions at this position have been previously identified in field isolates of PCV1 and PCV2.

Amino acid substitutions induced by cell culture passage or chemical mutagenesis techniques have been routinely used for the attenuation of many viruses, and have led to the productions of many vaccines (G. F. Brooks et al., "Pathogenesis & control of viral diseases," In: Jawetz, Melnick, &

Adelberg's Medical Microbiology, 21$^{st}$ Ed. (Publishers Appleton & Lange) 30: 363-365 (1998)). A single amino acid substitution can lead to the attenuation of a virus. For example, it has been previously reported that substitution of a proline for a leucine at residue 101 of the nonstructural 4B protein of the mosquito-borne Dengue 4 (DEN4) virus resulted in decreased viral replication in mosquito but a proportionally increased replication in human Vero cells (K. A. Hanley et al., "A trade-off in replication in mosquito versus mammalian systems conferred by a point mutation in the NS4B protein of dengue virus type 4," Virology. 312: 222-232 (2003)). Hence, the balancing control of efficient replication of DEN4 virus in either mosquito or human Vero cells was maintained by a single amino acid change. In the Circoviridae family, a single amino acid mutation in the VP1 capsid protein of CAV was found to be responsible for the pathogenicity of the virus in chickens (S. Yamaguchi et al., "Identification of a genetic determinant of pathogenicity in chicken anaemia virus," J. Gen. Virol. 82: 1233-1238 (2001)). Taken together, the results from the present invention strongly correlate the mutation to biological activity and demonstrate that P110A, R191S or collectively, is responsible for the attenuation of PCV2 VP120 in pigs or for the improved growth ability of PCV2 in PK-15 cells.

Since the results from this invention demonstrate that the P110A and R191S mutations in the capsid of PCV2 enhance the growth ability of PCV2 in vitro and attenuate the virus in vivo, the P110A and R191S mutations (both singly and collectively) may be advantageously introduced into the capsid gene of the chimeric PCV1-2 vaccine to make the chimera PCV1-2 vaccine of the invention grow better in cell cultures or make it safer in pigs. This is accomplished by inserting the mutated immunogenic capsid gene containing the novel P110A and R191S mutations in the chimeric clones in lieu of using the ORF2 of the pathogenic PCV2. The mutations are introduced into the capsid gene of the PCV1-2 vaccine using art-recognized techniques such as those found in the instruction manual for the QuikChange® Multi Site-Directed Mutagenesis Kit commercially available from Stratagene Inc., La Jolla, Calif. Alternatively, the mutated PCV2 ORF2 for use in the chimeric virus may be made by well-known biochemical synthesis processes to substitute one or both of the proline and arginine with the alanine and serine amino acids at positions 110 and 191, respectively, of the immunogenic capsid protein. The final mutant clones may be readily sequenced to ensure that the intended P110A, R191S or both mutations are properly introduced and there is no other unwanted mutation. The PCV1-2 vaccine containing the mutation may be further tested in cell culture by routine procedures to select the combination that facilitates cell culture growth or ensures improved safety measures when vaccinating pigs due to the further attenuation of PCV2 virulent properties, if any persist. While the benefit of the PCV1-2 chimera lies in its natural avirulent trait, the alternative use of the mutated PCV2 ORF2 to make the PCV1-2 chimera provides another embodiment of the present invention that is available if further safening of the natural live chimera vaccine becomes warranted.

Vaccines of the chimeric viral and molecular DNA clones, and methods of using them, are also included within the scope of the present invention. Inoculated pigs are protected from serious viral infection and PMWS caused by PCV2. The novel method protects pigs in need of protection against viral infection or PMWS by administering to the pig an immunologically effective amount of a vaccine according to the invention, such as, for example, a vaccine comprising an immunogenic amount of the chimeric PCV1-2 DNA, the cloned chimeric virus, a plasmid or viral vector containing the chimeric DNA of PCV1-2, the polypeptide expression products, the recombinant PCV2 DNA, etc. Other antigens such as PRRSV, PPV, other infectious swine agents and immune stimulants may be given concurrently to the pig to provide a broad spectrum of protection against viral infections.

The vaccines comprise, for example, the infectious chimeric PCV1-2 DNA, the cloned PCV chimeric DNA genome in suitable plasmids or vectors such as, for example, the pSK vector, an avirulent, live chimeric virus, an inactivated chimeric virus, etc. in combination with a nontoxic, physiologically acceptable carrier and, optionally, one or more adjuvants. The vaccine may also comprise the infectious PCV2 molecular DNA clone described herein. The infectious chimeric PCV1-2 DNA, the plasmid DNA containing the infectious chimeric viral genome and the live chimeric virus are preferred with the live chimeric virus being most preferred. The avirulent, live viral vaccine of the present invention provides an advantage over traditional viral vaccines that use either attenuated, live viruses which run the risk of reverting back to the virulent state or killed cell culture propagated whole virus which may not induce sufficient antibody immune response for protection against the viral disease.

The adjuvant, which may be administered in conjunction with the vaccine of the present invention, is a substance that increases the immunological response of the pig to the vaccine. The adjuvant may be administered at the same time and at the same site as the vaccine, or at a different time, for example, as a booster. Adjuvants also may advantageously be administered to the pig in a manner or at a site different from the manner or site in which the vaccine is administered. Suitable adjuvants include, but are not limited to, aluminum hydroxide (alum), immunostimulating complexes (IS-COMS), non-ionic block polymers or copolymers, cytokines (like IL-1, IL-2, IL-7, IFN-α, IFN-β, IFN-γ, etc.), saponins, monophosphoryl lipid A (MLA), muramyl dipeptides (MDP) and the like. Other suitable adjuvants include, for example, aluminum potassium sulfate, heat-labile or heat-stable enterotoxin isolated from *Escherichia coli*, cholera toxin or the B subunit thereof, diphtheria toxin, tetanus toxin, pertussis toxin, Freund's incomplete or complete adjuvant, etc. Toxin-based adjuvants, such as diphtheria toxin, tetanus toxin and pertussis toxin may be inactivated prior to use, for example, by treatment with formaldehyde.

The vaccines may further contain additional antigens to promote the immunological activity of the infectious chimeric PCV DNA clones such as, for example, porcine reproductive and respiratory syndrome virus (PRRSV), porcine parvovirus (PPV), other infectious swine agents and immune stimulants.

The new vaccines of this invention are not restricted to any particular type or method of preparation. The cloned viral vaccines include, but are not limited to, infectious DNA vaccines (i.e., using plasmids, vectors or other conventional carriers to directly inject DNA into pigs), live vaccines, modified live vaccines, inactivated vaccines, subunit vaccines, attenuated vaccines, genetically engineered vaccines, etc. These vaccines are prepared by standard methods known in the art.

The live viral vaccine is generally the most desirable vaccine in that all possible immune responses are activated in the recipient of the vaccine, including systemic, local, humoral and cell-mediated immune responses. A killed vaccine, on the other hand, can only induce humoral immune response. Albeit the most desirable, however, live viral vaccines have several disadvantages, such as the potential risk of contamination with live adventitious viral agents or the risk that the virus may revert to virulence in the field. Remarkably, the unique PCV1-2 chimeric DNA of the present invention overcomes those disadvantages. Using only the immunogenic genes of the pathogenic PCV2, the chimeric DNA constructs a live, replicating chimeric virus that is nonpathogenic yet elicits the complete, beneficial immune responses of live viral vaccines against the pathogenic PCV2 virus. The live virus vaccine based on the chimeric virus will have little chance, if any, for reversion to a pathogenic phenotype. Thus, the new chimeric virus based on the structure of the nonpathogenic PCV1 has a huge advantage over any recombinant PCV2 DNA virus, any live, attenuated PCV2 vaccine or any other type of vaccine predicated solely on PCV2 for immunity against the PCV2 infections.

Although the live viral vaccine is most preferred, other types of vaccines may be used to inoculate pigs with the new chimeric virus and other antigens described herein. To prepare inactivated virus vaccines, for instance, the virus propagation from the infectious DNA clone is done by methods known in the art or described herein. Serial virus inactivation is then optimized by protocols generally known to those of ordinary skill in the art.

Inactivated virus vaccines may be prepared by treating the chimeric virus derived from the cloned PCV DNA with inactivating agents such as formalin or hydrophobic solvents, acids, etc., by irradiation with ultraviolet light or X-rays, by heating, etc. Inactivation is conducted in a manner understood in the art. For example, in chemical inactivation, a suitable virus sample or serum sample containing the virus is treated for a sufficient length of time with a sufficient amount or concentration of inactivating agent at a sufficiently high (or low, depending on the inactivating agent) temperature or pH to inactivate the virus. Inactivation by heating is conducted at a temperature and for a length of time sufficient to inactivate the virus. Inactivation by irradiation is conducted using a wavelength of light or other energy source for a length of time sufficient to inactivate the virus. The virus is considered inactivated if it is unable to infect a cell susceptible to infection.

The preparation of subunit vaccines typically differs from the preparation of a modified live vaccine or an inactivated vaccine. Prior to preparation of a subunit vaccine, the protective or antigenic components of the vaccine must be identified. Such protective or antigenic components include certain amino acid segments or fragments of the viral capsid proteins which raise a particularly strong protective or immunological response in pigs; single or multiple viral capsid proteins themselves, oligomers thereof, and higher-order associations of the viral capsid proteins which form virus substructures or identifiable parts or units of such substructures; oligoglycosides, glycolipids or glycoproteins present on or near the surface of the virus or in viral substructures such as the lipoproteins or lipid groups associated with the virus, etc. Preferably, a capsid protein, such as the protein encoded by the ORF2 gene, is employed as the antigenic component of the subunit vaccine. Other proteins encoded by the infectious DNA clone may also be used. These immunogenic components are readily identified by methods known in the art. Once identified, the protective or antigenic portions of the virus (i.e., the "subunit") are subsequently purified and/or cloned by procedures known in the art. The subunit vaccine provides an advantage over other vaccines based on the live virus since the subunit, such as highly purified subunits of the virus, is less toxic than the whole virus.

If the subunit vaccine is produced through recombinant genetic techniques, expression of the cloned subunit such as the ORF2 (capsid) gene, for example, may be optimized by methods known to those in the art (see, for example, Maniatis et al., "Molecular Cloning: A Laboratory Manual," Cold Spring Harbor Laboratory, Cold Spring Harbor, Mass., 1989). If the subunit being employed represents an intact structural feature of the virus, such as an entire capsid protein, the procedure for its isolation from the virus must then be optimized. In either case, after optimization of the inactivation protocol, the subunit purification protocol may be optimized prior to manufacture.

To prepare attenuated vaccines from pathogenic clones, the tissue culture adapted, live, pathogenic PCV2 is first attenuated (rendered nonpathogenic or harmless) by methods known in the art, typically made by serial passage through cell cultures. Attenuation of pathogenic clones may also be made by gene deletions or viral-producing gene mutations. Then, the attenuated PCV2 viruses may be used to construct additional chimeric PCV1-2 viruses that retain the nonpathogenic phenotype of PCV1 but can vary in the strength of the immunogenicity traits selected from the PCV2 genome through recombinant technology. Desirably, the attenuation of the PCV2 is accomplished by obtaining the P110A, R191S or both mutations in the ORF2 and using the mutant PCV2 to construct the chimeric PCV1-2 viruses as described herein.

The most preferred vaccine employs the live chimeric virus DNA clone, in particular, the clone containing the immunogenic genes of PCV2 cloned in the backbone of the nonpathogenic PCV1. Advantageously, the live chimeric virus, which is naturally avirulent when constructed through genetic engineering, does not require time-consuming attenuation procedures. The virus uniquely serves as a live but nonpathogenic replicating virus that produces immunogenic proteins against PCV2 during virus replication, which can then elicit a full range of immune responses against the pathogenic PCV2.

As a further benefit, the preferred live chimeric virus of the present invention provides a genetically stable vaccine that is easier to make, store and deliver than other types of attenuated vaccines. Avirulent or attenuated vaccines based upon chimeric viruses are generally considered as safe as, if not safer than, the traditionally modified live vaccines (J. Arroyo et al., "Molecular basis for attenuation of neurovirulence of a yellow fever Virus/Japanese encephalitis virus chimera vaccine (ChimeriVax-JE)," J. Virol. 75(2):934-942 (2001); F. Guirakhoo et al., "Recombinant chimeric yellow fever-dengue type 2 virus is immunogenic and protective in nonhuman primates," J. Virol. 74(12):5477-5485 (2000); S. Tang et al., "Toward a poliovirus-based simian immunodeficiency virus vaccine: correlation between genetic stability and immunogenicity," J. Virol. 71(10):7841-7850 (1997)). For example, the ChimeriVax-JE vaccine against Japanese encephalitis virus (JEV), which is a genetically engineered derivative of the yellow fever virus vaccine YFV17D in which the genes encoding the structural proteins prM and E of YFV17D are replaced with the corresponding genes of the attenuated JEV SA14-14-2 strain, has been shown to be genetically stable after prolonged passages both in vitro and in vivo (J. Arroyo et al., 2001, supra). Another chimeric virus vaccine ChimeriVax-D2 against Dengue virus type 2, which is an attenuated chimeric yellow fever (YF)-dengue type 2 (dengue-2) virus, has also been found to be genetically stable; its sequences were reported to be unchanged after 18 passages in Vero cells (F. Guirakhoo et al., 2000, supra).

Another preferred vaccine of the present invention utilizes suitable plasmids for delivering the nonpathogenic chimeric DNA clone to pigs. In contrast to the traditional vaccine that uses live or killed cell culture propagated whole virus, this invention provides for the direct inoculation of pigs with the plasmid DNA containing the infectious chimeric viral genome.

Additional genetically engineered vaccines, which are desirable in the present invention, are produced by techniques known in the art. Such techniques involve, but are not limited to, further manipulation of recombinant DNA, modification of or substitutions to the amino acid sequences of the recombinant proteins and the like.

Genetically engineered vaccines based on recombinant DNA technology are made, for instance, by identifying alternative portions of the viral gene encoding proteins responsible for inducing a stronger immune or protective response in pigs (e.g., proteins derived from ORF3, ORF4, etc.). Such identified genes or immuno-dominant fragments can be cloned into standard protein expression vectors, such as the baculovirus vector, and used to infect appropriate host cells (see, for example, O'Reilly et al., "Baculovirus Expression Vectors: A Lab Manual," Freeman & Co., 1992). The host cells are cultured, thus expressing the desired vaccine proteins, which can be purified to the desired extent and formulated into a suitable vaccine product.

If the clones retain any undesirable natural abilities of causing disease, it is also possible to pinpoint the nucleotide sequences in the viral genome responsible for any residual virulence, and genetically engineer the virus avirulent through, for example, site-directed mutagenesis. Site-directed mutagenesis is able to add, delete or change one or more nucleotides (see, for instance, Zoller et al., DNA 3:479-488, 1984). An oligonucleotide is synthesized containing the desired mutation and annealed to a portion of single stranded viral DNA. The hybrid molecule, which results from that procedure, is employed to transform bacteria. Then double-stranded DNA, which is isolated containing the appropriate mutation, is used to produce full-length DNA by ligation to a restriction fragment of the latter that is subsequently transfected into a suitable cell culture. Ligation of the genome into the suitable vector for transfer may be accomplished through any standard technique known to those of ordinary skill in the art. Transfection of the vector into host cells for the production of viral progeny may be done using any of the conventional methods such as calcium-phosphate or DEAE-dextran mediated transfection, electroporation, protoplast fusion and other well-known techniques (e.g., Sambrook et al., "Molecular Cloning: A Laboratory Manual," Cold Spring Harbor Laboratory Press, 1989). The cloned virus then exhibits the desired mutation. Alternatively, two oligonucleotides can be synthesized which contain the appropriate mutation. These may be annealed to form double-stranded DNA that can be inserted in the viral DNA to produce full-length DNA.

Genetically engineered proteins, useful in vaccines, for instance, may be expressed in insect cells, yeast cells or mammalian cells. The genetically engineered proteins, which may be purified or isolated by conventional methods, can be directly inoculated into pigs to confer protection against viral infection or postweaning multisystemic wasting syndrome (PMWS) caused by PCV2.

An insect cell line (like HI-FIVE) can be transformed with a transfer vector containing nucleic acid molecules obtained from the virus or copied from the viral genome which encodes one or more of the immuno-dominant proteins of the virus. The transfer vector includes, for example, linearized baculovirus DNA and a plasmid containing the desired polynucleotides. The host cell line may be co-transfected with the linearized baculovirus DNA and a plasmid in order to make a recombinant baculovirus.

Alternatively, DNA from a pig suffering from PMWS, which encode one or more capsid proteins, the infectious PCV2 molecular DNA clone or the cloned PCV chimeric DNA genome can be inserted into live vectors, such as a poxvirus or an adenovirus and used as a vaccine.

An immunologically effective amount of the vaccines of the present invention is administered to a pig in need of protection against viral infection or PMWS. The immunologically effective amount or the immunogenic amount that inoculates the pig can be easily determined or readily titrated by routine testing. An effective amount is one in which a sufficient immunological response to the vaccine is attained to protect the pig exposed to the virus which causes PMWS. Preferably, the pig is protected to an extent in which one to all of the adverse physiological symptoms or effects of the viral disease are significantly reduced, ameliorated or totally prevented.

The vaccine can be administered in a single dose or in repeated doses. Dosages may range, for example, from about 1 microgram to about 1,000 micrograms of the plasmid DNA containing the infectious chimeric DNA genome (dependent upon the concentration of the immuno-active component of the vaccine), preferably 100 to 200 micrograms of the chimeric PCV1-2 DNA clone, but should not contain an amount of virus-based antigen sufficient to result in an adverse reaction or physiological symptoms of viral infection. Methods are known in the art for determining or titrating suitable dosages of active antigenic agent to find minimal effective dosages based on the weight of the pig, concentration of the antigen and other typical factors. Preferably, the infectious chimeric viral DNA clone is used as a vaccine, or a live infectious chimeric virus can be generated in vitro and then the live chimeric virus is used as a vaccine. In that case, from about 50 to about 10,000 of the 50% tissue culture infective dose ($TCID_{50}$) of live chimeric virus, for example, can be given to a pig.

Desirably, the vaccine is administered to a pig not yet exposed to the PCV virus. The vaccine containing the chimeric PCV1-2 infectious DNA clone or other antigenic forms thereof can conveniently be administered intranasally, transdermally (i.e., applied on or at the skin surface for systemic absorption), parenterally, etc. The parenteral route of administration includes, but is not limited to, intramuscular, intravenous, intraperitoneal, intradermal (i.e., injected or otherwise placed under the skin) routes and the like. Since the intramuscular and intradermal routes of inoculation have been successful in other studies using viral infectious DNA clones (E. E. Sparger et al., "Infection of cats by injection with DNA of feline immunodeficiency virus molecular clone," Virology 238:157-160 (1997); L. Willems et al., "In vivo transfection of bovine leukemia provirus into sheep," Virology 189:775-777 (1992)), these routes are most preferred, in addition to the practical intranasal route of administration. Although less convenient, it is also contemplated that the vaccine is given to the pig through the intralymphoid route of inoculation. A unique, highly preferred method of administration involves directly injecting the plasmid DNA containing PCV1-2 chimera into the pig intramuscularly, intradermally, intralymphoidly, etc.

When administered as a liquid, the present vaccine may be prepared in the form of an aqueous solution, syrup, an elixir, a tincture and the like. Such formulations are known in the art and are typically prepared by dissolution of the antigen and other typical additives in the appropriate carrier or solvent systems. Suitable carriers or solvents include, but are not limited to, water, saline, ethanol, ethylene glycol, glycerol, etc. Typical additives are, for example, certified dyes, flavors, sweeteners and antimicrobial preservatives such as thimerosal (sodium ethylmercurithiosalicylate). Such solutions may be stabilized, for example, by addition of partially hydrolyzed gelatin, sorbitol or cell culture medium, and may be buffered by conventional methods using reagents known in the art, such as sodium hydrogen phosphate, sodium dihydrogen phosphate, potassium hydrogen phosphate, potassium dihydrogen phosphate, a mixture thereof, and the like.

Liquid formulations also may include suspensions and emulsions that contain suspending or emulsifying agents in combination with other standard co-formulants. These types of liquid formulations may be prepared by conventional methods. Suspensions, for example, may be prepared using a colloid mill. Emulsions, for example, may be prepared using a homogenizer.

Parenteral formulations, designed for injection into body fluid systems, require proper isotonicity and pH buffering to the corresponding levels of porcine body fluids. Isotonicity can be appropriately adjusted with sodium chloride and other salts as needed. Suitable solvents, such as ethanol or propylene glycol, can be used to increase the solubility of the ingredients in the formulation and the stability of the liquid preparation. Further additives that can be employed in the present vaccine include, but are not limited to, dextrose, conventional antioxidants and conventional chelating agents such as ethylenediamine tetraacetic acid (EDTA). Parenteral dosage forms must also be sterilized prior to use.

Another embodiment of the present invention involves a new method of preparing an infectious, nonpathogenic chimeric nucleic acid molecule of PCV1-2, which comprises removing an open reading frame (ORF) gene of a nucleic acid molecule encoding an infectious nonpathogenic PCV1, replacing the same position with an immunogenic ORF gene of a nucleic acid molecule encoding an infectious pathogenic PCV2, and recovering the chimeric nucleic acid molecule. The nucleic acid molecule is typically DNA. A preferred method replaces the ORF2 gene of the nonpathogenic PCV1 DNA with the immunogenic ORF2 capsid gene of the infectious pathogenic molecular DNA of PCV2 described herein. It is contemplated that other ORF positions or immunogenic fragments thereof can be exchanged between the PCV1 and PCV2 DNA to construct the attenuated infectious chimeric DNA clones according to the methods described herein.

The recombinant nucleic acid molecule is then used to construct the live, infectious, replicating chimeric virus of the present invention that advantageously retains the nonpathogenic nature of PCV1 yet expresses the immunogenic ORF2 protein of the pathogenic PCV2 and elicits a complete immune response against the pathogenic PCV2. Desirably, the PCV1-2 DNA clone serves as a genetically engineered avirulent, live vaccine against PCV2 infection and PMWS in pigs.

An infectious DNA clone of PCV2 is constructed, as described herein, so that a biologically pure and homogeneous infectious virus stock can be generated for pathogenesis studies and the development of nonpathogenic, chimeric vaccines. The course of clinical disease, virus distribution and pathological lesions associated with PCV2 infection are more definitively characterized by using this molecular DNA clone and a biologically pure and homogeneous infectious PCV2 virus stock derived from the molecular DNA clone than have been observed in the past, which lends itself to the development of the desired vaccine products of the present invention.

The PCV2 molecular clone is generated by ligating two copies of the complete PCV2 genome in tandem into the pSK vector. In sharp contrast to the single copy genome disclosed in the art, the infectious DNA PCV2 clone made by the methods described herein contains two complete copies of the PCV2 genome ligated together in tandem repeat. Ligating two copies of genome in tandem provides a similar circular genome that mimics the usual circular genome of PCV2. The advantage of having two copies of the genome in tandem in the infectious DNA PCV2 clone is to be able to maximize replication when the infectious DNA clone is transfected in vitro and in vivo. Thus, the clone of the invention operates more efficiently and effectively than the prior single copy genome.

Infection of animals with the molecular viral clone is extremely useful to studying the genetic determinants of viral replication and virulence in the host. Type-2 porcine circovirus (PCV2) has been incriminated as the causative agent of postweaning multisystemic wasting syndrome (PMWS). PMWS is a complex disease syndrome in swine and multiple factors may be involved in the clinical presentation of PMWS. However, the difficulty in producing a biologically pure form of PCV2 due to the presence of other common swine agents in the tissue homogenates of diseased pigs has impeded a definitive characterization of the clinical disease and pathological lesions solely attributable to PCV2 infection. This is the first time an infectious molecular DNA clone of PCV2 has been constructed and used to characterize the disease and pathological lesions associated with PCV2 infection by direct in vivo transfection of pigs with the molecular clone.

The homogeneous PCV2 live virus stock derived from the molecular clone is shown to be infectious in vitro when transfected into PK-15 cells. The cloned PCV2 genomic DNA is also infectious when directly injected into the livers and superficial iliac lymph nodes of specific-pathogen-free (SPF) pigs. Animals injected with the cloned PCV2 plasmid DNA develop an infection and disease resembling that induced by intranasal inoculation with a homogenous, infectious PCV2 live virus stock. Seroconversion to PCV2-specific antibody is detected in the majority of pigs from the inoculated groups at 35 days postinoculation (DPI).

The onset and duration of viremia in pigs inoculated with the chimeric PCV1-2 DNA clone are similar to those of the pigs inoculated with the nonpathogenic PCV1 DNA clone, whereas viremia in pigs inoculated with the PCV2 clone appears earlier and lasted longer. Beginning at 14 DPI and lasting about 2-4 weeks, viremia is detected in the majority of the PCV2-inoculated animals. Similarly, the majority of inoculated pigs necropsied at 35 DPI seroconverted to PCV2-antibodies. PCV2 antigen is detected in various tissues and organs in inoculated pigs. Gross lesions are limited to the lungs and lymph nodes, and are characterized by systematically enlarged tan colored lymph nodes, lungs that failed to collapse and mild multifocal tan-colored foci of consolidation. Gross lesions affecting the lymph nodes in both the nonpathogenic PCV1 and the chimeric PCV1-2 inoculated pigs are mild and limited to only a few animals, whereas the pathogenic PCV2 inoculated pigs all have moderate-to-severe swelling and discoloration of lymphoid tissues (Table 9, below). Statistical analysis reveals that the scores of the gross lesions in the lymph nodes of the chimeric PCV1-2 inoculated animals are similar to those in nonpathogenic PCV1 inoculated pigs. At 21 DPI, PCV2 inoculated pigs have gross lesions that are statistically more severe than those of the PCV1 and the chimeric PCV1-2 inoculated pigs. Histopathological lesions and PCV2-specific antigen are detected in numerous tissues and organs including brain, lung, heart, kidney, tonsil, lymph nodes, spleen, ileum and liver of the inoculated (infected) pigs. The histopathological lesions in multiple tissues and organs similar to those of PMWS are reproduced with the PCV2 molecular DNA clone as well as with the infectious virus prepared in vitro from the molecular DNA clone. Microscopically, at both 21 and 49 DPIs, the chimeric PCV1-2 inoculated animals have statistically less microscopic lesions than the PCV2 inoculated animals. The microscopic lesion scores in lymph nodes of the chimeric PCV1-2 inoculated pigs are similar to those of the nonpathogenic PCV1, the reciprocal chimeric PCV2-1 and the uninoculated control animals. Moderate to severe microscopic lesions are found in multiple tissues of pathogenic PCV2 inoculated animals including lung, liver, lymphoid, spleen, brain, heart, kidney and tonsil tissue. However, in chimeric PCV1-2 inoculated animals, mild to moderate microscopic lesions are limited only to liver, lymph nodes and kidney tissues (see Table 10, below).

There are no remarkable clinical signs of PMWS in the control or any of the inoculated pigs. Although the characteristic clinical symptoms of PMWS are not observed with the cloned PCV2 plasmid DNA (the infectious PCV2 DNA clone) or with a biologically pure PCV2 infectious virus stock, PCV2 is clearly responsible for the PMWS-like histopathological lesions reproduced in the below illustrative examples. It is generally believed that PCV2 is the primary but not the sole pathogenic agent responsible for the onset of clinical PMWS.

This invention more definitively characterizes the clinical course and pathological lesions exclusively attributable to PCV2 infection. The present data in the below illustrative examples indicate that the readily reproduced, cloned PCV2 genomic DNA is available to replace infectious virus for the PCV2 pathogenesis and immunization studies. While PCV2 is shown as essential for development of PMWS, other factors or agents such as PRRSV, PPV, etc. may be required to induce the full spectrum of clinical signs and lesions associated with advanced cases of PMWS. However, with the knowledge that PCV2 is a key factor, the novel infectious, replicating viral clone of the present invention can be further modified or genetically engineered to achieve the desired optimal immunogenic effect through methods known to those of ordinary skill in immunology and molecular genetics.

The availability of the infectious DNA clone of PCV2 described herein makes it feasible to develop the genetically engineered attenuated vaccine for preventing PCV2 infection and PMWS in pigs. It is known that PCV2 replicates in the lymph nodes, lungs and liver during natural infection, and one of the major pathogenic effects is the impairment of the immune system by degradation of the lymphoid structures (S. Krakowka et al., 2001, supra; G. M. Allan and J. A. Ellis, 2000, supra; S. Kennedy et al., 2000, supra; G. J. Wellenberg et al., 2000, supra; G. M. Allan et al., "Experimental reproduction of severe wasting disease by co-infection of pigs with porcine circovirus and porcine parvovirus," J. Comp. Pathol. 121:1-11(1999); J. Ellis et al., "Reproduction of lesions of postweaning multisystemic wasting syndrome in gnotobiotic piglets," J. Vet. Diagn. Invest. 11:3-14 (1999); J. C. Harding and E. G. Clark, 1997, supra). By using this novel infectious PCV2 molecular DNA clone, the clinical disease, pathological lesions and virus distribution exclusively attributable to PCV2 infection are more definitively characterized.

The structural and functional relationships of the PCV genes are better understood due to the availability of the PCV2, PCV1, chimeric PCV1-2, and reciprocal chimeric PCV2-1 infectious DNA clones described herein. Will et al., "Cloned HBV DNA causes hepatitis in chimpanzees," Nature 299:740-742 (1982), first demonstrated the feasibility of using a cloned hepatitis B virus DNA to infect chimpanzees by direct in vivo injection. This approach has since been used to study viral replication and pathogenesis of several other viruses (T. W. Dubensky et al., "Direct transfection of viral and plasmid DNA into the liver or spleen of mice," Proc. Natl. Acad. Sci. USA 81:7529-7533 (1984); R. Girones et al., "Complete nucleotide sequence of a molecular clone of woodchuck hepatitis virus that is infectious in the natural host," Proc. Natl. Acad. Sci. USA 86:1846-1849(1989); N. L. Letvin et al., "Risks of handling HIV," Nature 349:573 (1991); C. Seeger et al., "The cloned genome of ground squirrel hepatitis virus is infectious in the animal. Proc. Natl. Acad. Sci. USA. 81:5849-5852 (1984); E. E. Sparger et al., "Infection of cats by injection with DNA of feline immunodeficiency virus molecular clone," Virology 238:157-160 (1997); R. Sprengel et al., "Homologous recombination between hepadnaviral genomes following in vivo DNA transfection: implications for studies of viral infectivity," Virology 159:454-456 (1987); H. Will et al., 1982, supra; L. Willems et al., "In vivo transfection of bovine leukemia provirus into sheep," Virology 189:775-777 (1992)).

The construction of an infectious PCV2 molecular DNA clone, and the demonstration of infection by direct injection of cloned PCV2 plasmid DNA into the liver and lymph nodes of pigs in the context of the present invention are advantageous for PCV2 studies. This in vivo transfection system will enhance the study of the structural and functional relationship of PCV2 genes using recombinant plasmids constructed in vitro to test different regions or genes of PCV2 for their roles in virus replication and pathogenesis in the host. The replication and pathogenesis of PCV2 can be studied in vivo without having to produce infectious virus stocks by propagating PCV2 in cell cultures. This is advantageous as serial cell culture passages may select for viral variants. Another advantage of using cloned PCV2 genomic DNA, instead of live virus, for animal studies is its relative ease for quantitation of the inoculation dose. The amount of the cloned PCV2 DNA used for animal inoculation can be easily determined by a spectrophotometer, whereas the dose of live PCV2 virus requires infectivity titration in cell cultures and confirmation of infection by IFA. Direct injection of animals with cloned PCV2 plasmid DNA eliminates the problems associated with the presence of other indigenous swine agents in tissue homogenate inocula in animal studies.

In the present invention, the immunogenic ORF2 capsid gene is switched between the pathogenic PCV2 and the nonpathogenic PCV1 to produce the unique structure of the chimeric PCV1-2 infectious DNA clone. Surprisingly and advantageously, the chimeric PCV1-2 infectious clone replicated, expressed the immunogenic ORF2 capsid antigen in vitro and in vivo, and induced a specific antibody response against PCV2 ORF2 but retained the nonpathogenic nature of PCV1. The chimeric PCV1-2 infectious DNA clone has the ability to induce a strong immune response against PCV2 while inducing only a limited infection with mild pathologic lesions similar to that of the nonpathogenic PCV1. For vaccine development, the relatively easy storage and stability of cloned DNA, and the economy of large-scale recombinant PCV2 plasmid DNA and chimeric PCV1-2 DNA clone production provides an attractive means of delivering a live, infectious viral DNA vaccine or genetically engineered, attenuated viral vaccines to pigs. Therefore, the chimeric PCV1-2 infectious DNA clone taught in this invention is a useful vaccine candidate against PCV2 infection and PMWS.

It should be appreciated that all scientific and technological terms used herein have the same meaning as commonly understood by those of ordinary skill in the art. For purposes of this invention, the term "infectious" means that the virus replicates in pigs, regardless of whether or not the virus causes any diseases. "SPF" refers to Specific-pathogen-free pigs. The "gnotobiotic" pigs intend germ-free pigs. The terms "PCV2 plasmid DNA," "PCV2 genomic DNA" and "PCV2 molecular DNA" are being used interchangeably to refer to the same cloned nucleotide sequence.

The infectious PCV1/PCV2 chimeric DNA clone (strain designation "PCV1-2 chimera"), the infectious PCV2 molecular DNA clone (strain designation "PCV2 clone") and the biologically pure and homogeneous PCV2 stock derived from an Iowa sample of PCV2 that had been isolated from a pig with severe PMWS and identified as isolate number 40895 (strain designation "PCV2 #40895") are deposited under the conditions mandated by 37 C.F.R. § 1.808 and maintained pursuant to the Budapest Treaty in the American Type Culture Collection (ATCC), 10801 University Boulevard, Manassas, Va. 20110-2209, U.S.A. The DNA sequences described herein are contained within 6,490 bp plasmids cloned into pBluescript SK(+) vector (pSK) (Stratagene Inc., La Jolla, Calif.) and transformed into *Escherichia coli* DH5α competent cells. The plasmids containing the infectious chimeric PCV1-2 DNA clone (identified as "chimeric porcine circovirus Type 1 (PCV1) and Type 2 (PCV2) infectious DNA clone") and the infectious PCV2 molecular DNA clone (identified as "infectious DNA clone of Type 2 porcine circovirus (PCV2)") have been deposited in the ATCC on Dec. 7, 2001 and have been assigned ATCC Patent Deposit Designations PTA-3912 and PTA-3913, respectively. It should be appreciated that other plasmids, which may be readily constructed using site-directed mutagenesis and the techniques described herein, are also encompassed within the scope of the present invention. The biologically pure and homogeneous PCV2 sample of isolate number 40895 (identified as "Type 2 porcine circovirus (PCV2)") has also been deposited in the ATCC on Dec. 7, 2001 and has been assigned ATCC Patent Deposit Designation PTA-3914. The genomic (nucleotide) sequence of the PCV2 isolate number 40895 has been deposited with the Genbank database and has been publicly available since Jul. 23, 2000 under accession number AF264042.

The following examples demonstrate certain aspects of the present invention. However, it is to be understood that these examples are for illustration only and do not purport to be wholly definitive as to conditions and scope of this invention. It should be appreciated that when typical reaction conditions (e.g., temperature, reaction times, etc.) have been given, the conditions both above and below the specified ranges can also be used, though generally less conveniently. The examples are conducted at room temperature (about 23° C. to about 28° C.) and at atmospheric pressure. All parts and percents referred to herein are on a weight basis and all temperatures are expressed in degrees centigrade unless otherwise specified.

A further understanding of the invention may be obtained from the non-limiting examples that follow below.

EXAMPLE 1

Generation of a PK-15 Cell Line Free of PCV1 Contamination

The source of the PCV2 isolate was from a spleen tissue sample of a pig with naturally occurring PMWS (PCV2 serial identification number 40895, referred to as "isolate 40895") (M. Fenaux et al., 2000, supra). Immunohistochemical staining (IHC) with PCV2-specific antibody confirmed the presence of PCV2 antigen in the tissue. The spleen tissues were stored at −80° C. until use.

The PK-15 cell line purchased from the American Type Culture Collection (ATCC accession number CCL-33) was persistently infected with PCV1 (G. C. Dulac and A. Afshar, 1989, supra). Since only a subpopulation of PK-15 cells was persistently infected (id.), a PK-15 cell line that is free of PCV1 contamination by end-point dilution was generated. Protocol proceeded as follows: PK-15 cells were grown in MEM with Earle's salts and L-glutamine (Life Technologies, Inc., Grand Island, N.Y.) supplemented with 10% fetal bovine serum (FBS) and 1×antibiotic (Life Technologies, Inc.). Confluent cell monolayers were trypsinized, and the cells were then counted and serially diluted to an end point with one cell per 0.2 ml. The end point dilution was plated in 96-well plates and allowed to grow into a monolayer starting from a single cell. Cells from each well were tested for PCV1 DNA using a PCR-RFLP assay capable of detecting and differentiating PCV1 and PCV2 (M. Fenaux et al., 2000, supra). PK-15 cells from wells that were tested negative for PCV1 by the PCR-RFLP assay were subsequently expanded. The PCV1 free PK-15 cell line was subcultured five additional passages and was found negative for PCV1 DNA by PCR at each passage.

Four cell lines that were negative for PCV1 contamination were produced by the end-point dilution of the persistently infected PK-15 cells from ATCC. The cell lines remained negative for PCV1 by PCR after the five additional passages. One of the cell lines was subsequently expanded and was shown to be able to support PCV2 replication when the cells were transfected with the PCV2 molecular DNA clone (FIG. 2) and infected with PCV2 virus. The cloned cells were further used for the in vitro transfection of PCV2 molecular DNA clone to generate a biologically pure PCV2 infectious virus stock for the animal inoculation experiment.

EXAMPLE 2

Construction of the PCV2 Infectious DNA Clone

To construct a PCV2 molecular DNA clone, a pair of PCR primers was designed according to the published sequence of the PCV2 isolate 40895 (M. Fenaux et al., 2000, supra): forward primer F-PCVSAC2 (5'-GAACCGCGGGCTG-GCTGAACTTTTGAAAGT-3'), set forth in SEQ ID NO:5, and reverse primer R-PCVSAC2 (5'-GCACCGCG-GAAATTTCTGACAAACGTTACA-3'), set forth in SEQ ID NO:6. This pair of primers amplifies the complete genome of PCV2 with an overlapping region containing the unique SacII restriction enzyme site (FIG. 1). DNA was extracted using the QIAamp DNA Minikit (Qiagen, Inc., Valencia, Calif.) from a spleen tissue sample of a pig with naturally occurring PMWS (isolate 40895) (M. Fenaux et al., 2000, supra). The extracted DNA was amplified by PCR with AmpliTaq Gold polymerase (Perkin-Elmer, Norwalk, Conn.). The PCR reaction consisted of an initial enzyme activation step at 95° C. for 9 min, followed by 35 cycles of denaturation at 94° C. for 1 min, annealing at 48° C. for 1 min, extension at 72° C. for 3 min, and a final extension at 72° C. for 7 min. The PCR product of expected size was separated by gel electrophoresis and purified with the glassmilk procedure with a Geneclean Kit (Bio 101, Inc., La Jolla, Calif.).

To construct a molecular DNA clone containing a tandem dimer of PCV2 genome, the PCR product containing the complete PCV2 genome was first ligated into the advanTAge plasmid vector (Clontech, Palo Alto, Calif.). E. Coli DH5α competent cells were transformed. The recombinant plasmids were verified by restriction enzyme digestion. The full length PCV2 genomic DNA was excised from the advanTAge vector by digestion with SacII restriction enzyme. The digested PCV2 genomic DNA was ligated with T4 DNA ligase at 37° C. for only 10 min, which favors the production of tandem dimers. The tandem dimers were subsequently cloned into pBluescript SK(+) vector (pSK) (Stratagene Inc., La Jolla, Calif.) (FIG. 1). Recombinant plasmids containing tandem dimers of PCV2 genome (herein referred to as PCV2 molecular DNA clone) were confirmed by PCR, restriction enzyme digestion, and DNA sequencing. The DNA concentration of the recombinant plasmids was determined spectrophotometrically.

Figure 2B:
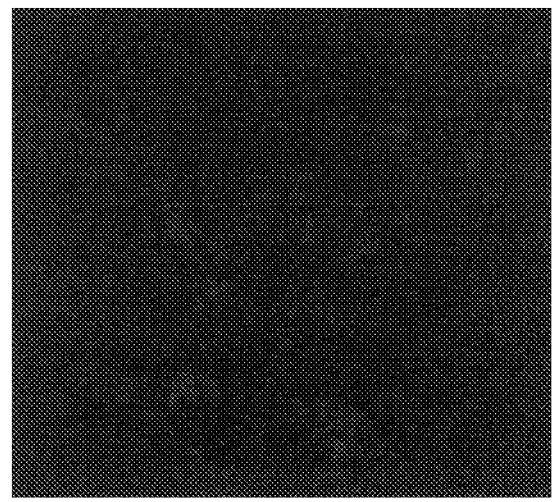

Specifically, the complete genome of the PCV2 (isolate 40895) was amplified by PCR to construct the infectious PCV2 molecular DNA clone. Two copies of the complete PCV2 genome were ligated in tandem into the pSK vector to produce the PCV2 molecular DNA clone (FIG. 1). The infectivity of the PCV2 molecular DNA clone was determined by in vitro transfection of the PK-15 cells. IFA with PCV2-specific antibody confirmed that the molecular DNA clone is infectious in vitro and that about 10-15% of the PK-15 cells were transfected. PCV2-specific antigen was visualized by IFA in the nucleus, and to a lesser degree, cytoplasm of the transfected cells (FIG. 2). The cells mock-transfected with the empty pSK vector remained negative for PCV2 antigen.

EXAMPLE 3

In Vitro Transfection with the PCV2 Molecular DNA Clone and Generation of a Biologically Pure and Homogenous PCV2 Infectious Virus Stock To test the infectivity of the molecular DNA clone in vitro, PK-15 cells free of PCV1 contamination were grown in 8-well LabTek chamber slides. When the PK-15 cells reached about 85% confluency, cells were transfected with the molecular DNA clone using Lipofectamine Plus Reagents according to the protocol supplied by the manufacturer (Life Technologies, Inc). Mock-transfected cells with empty pSK vector were included as controls. Three days after transfection, the cells were fixed with a solution containing 80% acetone and 20% methanol at 4° C. for 20 min., and an immunofluorescence assay using a PCV2-specific rabbit polyclonal antisera was performed to determine the in vitro infectivity of the molecular DNA clone (see below).

To generate a biologically pure and homogeneous PCV2 infectious virus stock for the animal inoculation experiment, PK-15 cells free of PCV1 contamination were cultivated in T-25 culture flasks and transfected with the PCV2 molecular DNA clone. PK-15 cells were grown to about 85% confluency in T-25 flasks. The cells were washed once with sterile PBS buffer before transfection. For each transfection reaction in a T-25 flask, 12 μg of the PCV2 plasmid DNA was mixed with 16 μl of Plus Reagent in 0.35 ml of MEM media. A flask of mock-transfected cells with empty pSK vector was included as the negative control. After incubation at room temperature for 15 min., 50 μl of Lipofectamine Reagent diluted in 0.35 ml of MEM media was added to the mixture and incubated at room temperature for another 15 min. The transfection mixture was then added to a T-25 flask of PK-15 cells containing 2.5 ml of fresh MEM. After incubation at 37° C. for 3 hrs, the media was replaced with fresh MEM media containing 2% FBS and 1× antibiotics. The transfected cells were harvested at 3 days post transfection and stored at −80° C. until use. The infectious titer of the virus stock was determined by IFA (see below).

Basically, biologically pure and homogenous PCV2 infectious virus stock was generated by transfection of PK-15 cells with the PCV2 molecular DNA clone. PCV2 virions produced by in vitro transfection were infectious since the transfected cell lysates were successfully used to infect PK-15 cells. Thus, the PCV2 molecular DNA clone is capable of producing infectious PCV2 virions when transfected in vitro. The infectious titer of the homogenous PCV2 virus stock prepared from transfected cells was determined to be $1 \times 10^{4.5}$ TCID$_{50}$/ml. This virus stock was used to inoculate pigs in Group 2. Lysates of cells mock-transfected with the empty pSK vector were unable to infect PK-15 cells.

EXAMPLE 4

Virus Titration by Immunofluorescence Assay (IFA)

To determine the infectious titer of the homogenous PCV2 virus stock, PK-15 cells were cultivated on 8-well LabTek chamber slides. The virus stock was serially diluted 10-fold in MEM, and each dilution was inoculated onto 10 wells of the monolayers of the PK-15 cells growing on the LabTek chamber slides. Wells of non-inoculated cells were included as controls. The infected cells were fixed at 3 days post inoculation with a solution containing 80% acetone and 20% methanol at 4° C. for 20 min. After washing the cells with PBS buffer, the infected cells were incubated with a 1:1,000 diluted PCV2-specific rabbit polyclonal antibody (S. D. Sorden et al., "Development of a polyclonal-antibody-based immunohistochemical method for the detection of type 2 porcine circovirus in formalin-fixed, paraffin-embedded tissue," J. Vet. Diagn. Invest. 11:528-530 (1999)) at 37° C. for 1 hr. The cells were then washed three times with PBS buffer, and incubated with a secondary FITC-labeled goat anti-rabbit IgG (Kirkegaard & Perry Laboratories Inc, Gaithersburg, Md.) at 37° C. for 45 min. After washing the slides three times with PBS buffer, and the slides were mounted with fluoromount-G, cover-slipped and examined under a fluorescence microscope. The 50% tissue culture infectious dose per ml (TCID$_{50}$/ml) was calculated. Initially, cells were transfected with a plasmid construct containing a single copy of PCV2 genome but the infectious PCV2 titer from the single genome construct is much lower than the one containing the tandem genome. Therefore, the plasmid construct containing the dimeric form of PCV2 genome was used for the in vitro and in vivo transfection experiments.

EXAMPLE 5

In Vivo Transfection of Pigs with the PCV2 Molecular DNA Clone and Experimental Inoculation of Pigs with the Homogeneous PCV2 Infectious Virus Stock Forty specific-pathogen-free (SPF) swine of 4 weeks of age were randomly assigned into 4 rooms of 10 animals each. Prior to inoculation, the SPF pigs were tested for antibodies to PCV, PRRSV, PPV and swine hepatitis E virus. Pigs in Group 1 were uninoculated and served as negative controls. Pigs in Group 2 were each inoculated intranasally with about $1.9 \times 10^5$ $TCID_{50}$ of the PCV2 infectious virus stock derived from the PCV2 molecular DNA clone. Pigs in Group 3 received direct intrahepatic injection of the recombinant plasmid DNA of the PCV2 molecular clone. Each pig was injected with a total of 200 µg of recombinant plasmid DNA (the cloned PCV2 plasmid DNA), through an ultrasound-guided technique, into 6 different sites of the liver. Pigs in Group 4 were each injected with a total of 200 µg of the recombinant PCV2 plasmid DNA directly into the superficial iliac lymph nodes, and each lymph node received two separate injections. The animals were monitored daily for clinical signs of disease. Serum samples were collected from each animal at 0, 7, 14, 21, 28, 35 days post inoculation (DPI). At 21 DPI, five pigs were randomly selected from each group and necropsied. The remaining five animals in each group were necropsied at 35 DPI. Various tissues and organs were collected during necropsy and processed for histological examination and immunohistochemical staining (see below).

The results are shown in Table 1 below. All inoculated pigs from Groups 2, 3 and 4 were negative for PCV2 antibodies at 0 DPI. Two pigs in the uninoculated control Group 1 had detectable PCV2 maternal antibody at 0 DPI. The maternal antibody in these two piglets waned by 7 DPI. No seroconversion to PCV2 antibody was detected in any of the 10 uninoculated control pigs. In Group 2 pigs intranasally inoculated with PCV2 infectious virus, 1 piglet seroconverted to PCV2 antibody at 21 DPI. By 35 DPI, 4 of the 5 remaining Group 2 pigs had seroconverted. Seroconversion in transfected animals from Groups 3 and 4 first appeared at 28 DPI. By 35 DPI, 5 of 5 remaining pigs from Group 3 and 3 of 5 remaining pigs from Group 4 had seroconverted to PCV2 antibody.

PPV antibodies were tested at 3 and 21 DPI for all pigs, and at 35 DPI for the remaining pigs. Maternal antibodies to the ubiquitous swine agent PPV were detected in the SPF piglets. The PPV HI antibody titers in all piglets but one decreased significantly from 3 DPI (an average titer of 1:2,665) to 21 DPI (an average titer of 1:246), indicating the antibody detected in these piglets was passively derived. One piglet had a slightly increased PPV HI titer from 1:32 at 3 DPI to 1:64 at 21 DPI, which is likely due to testing variation. Serum samples collected from all pigs at 0, 21, and 35 DPI were further tested for PPV DNA with a published PCR assay (J. M. Soucie et al., "Investigation of porcine parvovirus among persons with hemophilia receiving Hyate: C porcine factor VIII concentrate," Transfusion 40:708-711 (2000)). No PPV viremia was detected from any pigs at any DPI, further indicating the pigs were not infected by PPV.

TABLE 1

Seroconversion to PCV2 Specific Antibodies in Pigs Inoculated With PCV2 Live Virus or Directly Injected With Cloned PCV2 Plasmid DNA

| Group | Inocula | Route of Inoculation | 0 | 7 | 14 | 21 | 28 | 35 |
|---|---|---|---|---|---|---|---|---|
| 1 | None | | 2/10[a] | 0/10 | 0/10 | 0/10 | 0/5 | 0/5 |
| 2 | PCV2 live virus[b] | Intranasal | 0/10 | 0/10 | 0/10 | 1/10 | 1/5 | 4/5 |
| 3 | PCV2 DNA[c] | Intrahepatic | 0/10 | 0/10 | 0/10 | 0/10 | 1/5 | 5/5 |
| 4 | PCV2 DNA[c] | Intralymphoid | 0/10 | 0/10 | 0/10 | 0/10 | 1/5 | 3/5 |

[a] PCV2 antibody was measured with an ELISA, number positive/number tested.
[b] A biologically pure and homogeneous PCV2 virus stock generated by transfection of PK-15 cells with PCV2 molecular DNA clone.
[c] Cloned PCV2 genomic DNA in pSK plasmid.

EXAMPLE 6

PCR-RFLP Analyses

To measure PCV2 viremia in pigs transfected with PCV2 molecular DNA clone and in pigs infected with PCV2 infectious virus stock, serum samples collected at different DPIs were tested for the presence of PCV2 DNA by the general methods of a PCR-RFLP assay previously described (M. Fenaux et al., 2000, supra). Viral DNA was extracted from 50 µl of each serum sample using the DNAzol® reagent according to the protocol supplied by the manufacturer (Molecular Research Center, Cincinnati, Ohio). The extracted DNA was resuspended in DNase-, RNase-, and proteinase-free water and tested for PCV2 DNA by PCR-RFLP (id.). PCR products from selected animals were sequenced to verify the origin of the virus infecting pigs.

Serum samples were collected from all control and inoculated animals at 0, 7, 14, 21, 28, and 35 DPIs and assayed for PCV2 viremia by detection of PCV2 DNA (id.). The results are shown in Table 2 below. PCV2 DNA was not detected in the Group 1 uninoculated control pigs at any DPI. Viremia was detected in 7/10 pigs from Group 2 at 14 DPI and 8/10 by 35 DPI. Viremia lasted only a few weeks as the PCV2 DNA was not detectable at 28 DPI and 35 DPI in all 5 remaining pigs from Group 2. In Group 3 pigs that were intrahepatically injected with PCV2 molecular DNA clone, 8/10 pigs were viremic at 14 DPI, and 9/10 pigs had detectable viremia by 35 DPI. Group 4 pigs were injected with PCV2 molecular DNA clone into the lymph nodes. Two of 10 pigs at 14 DPI and 8 of 10 pigs at 21 DPI from Group 4 were viremic. The results show that PCV2 molecular DNA clone is infectious when injected directly into the liver and superficial iliac lymph nodes of SPF pigs. PCR products amplified from selected animals were sequenced. The sequence of the PCR products amplified from selected animals was identical to the corresponding region of the PCV2 molecular DNA clone.

TABLE 2

Detection of Viremia (PCV2 DNA) by PCR in Sera of Inoculated and Control Pigs

| Group | Inocula | Route of Inoculation | Days Postinoculation ||||||  |
|---|---|---|---|---|---|---|---|---|---|
| | | | 0 | 7 | 14 | 21 | 28 | 35 | Total |
| 1 | None | | 0/10[a] | 0/10 | 0/10 | 0/10 | 0/5 | 0/5 | 0/10 |
| 2 | PCV2 live virus[b] | Intranasal | 0/10 | 0/10 | 7/10 | 5/10 | 0/5 | 0/5 | 8/10 |
| 3 | PCV2 DNA[c] | Intrahepatic | 0/10 | 0/10 | 8/10 | 6/10 | 3/5 | 3/5 | 9/10 |
| 4 | PCV2 DNA[c] | Intralymphoid | 0/10 | 0/10 | 2/10 | 8/10 | 2/5 | 0/5 | 8/10 |

[a]10 pigs in each group, number positive/number tested.
[b]A biologically pure and homogeneous PCV2 virus stock generated by transfection of PK-15 cells with PCV2 molecular DNA clone.
[c]Cloned PCV2 genomic DNA in pSK plasmid.

EXAMPLE 7

Clinical Evaluation

Pigs were weighed on 0 DPI and at the time of necropsy. Rectal temperatures and clinical respiratory disease scores, ranging from 0 to 6 (0=normal, 6=severe) (P. G. Halbur et al., "Comparison of the pathogenicity of two U.S. porcine reproductive and respiratory syndrome virus isolates with that of the Lelystad virus," Vet. Pathol. 32:648-660 (1995)), were recorded every other day from 0 to 35 DPI. Clinical observations including evidence of central nervous system disease, liver disease (icterus), musculoskeletal disease, and changes in body condition, were also recorded daily.

To evaluate the gross pathology and histopathology, five pigs from each group were randomly selected for necropsies at 21 and 35 DPI. The necropsy team was blinded to infection status of the pigs at necropsy. Complete necropsies were performed on all pigs. An estimated percentage of the lung with grossly visible pneumonia was recorded for each pig based on a previously described scoring system (id.). The scoring system is based on the approximate volume that each lung lobe contributes to the entire lung: the right cranial lobe, right middle lobe, cranial part of the left cranial lobe, and the caudal part of the left cranial lobe each contribute 10% of the total lung volume, the accessory lobe contributes 5%, and the right and left caudal lobes each contribute 27.5%. Other lesions such as enlargement of lymph nodes were noted separately. Sections for histopathologic examination were taken from nasal turbinate, lungs (seven sections) (id.), heart, brain, lymph nodes (tracheobronchial, iliac, mesenteric, subinguinal), tonsil, thymus, liver, gall bladder, spleen, joints, small intestine, colon, pancreas, and kidney. The tissues were examined in a blinded fashion and given a subjective score for severity of lung, lymph node, and liver lesions. Lung scores ranged from 0 (normal) to 3 (severe lymphohistiocytic interstitial pneumonia). Liver scores ranged from 0 (normal) to 3 (severe lymphohistiocytic hepatitis). Lymph node scores were for an estimated amount of lymphoid depletion of follicles ranging from 0 (normal or no lymphoid depletion) to 3 (severe lymphoid depletion and histiocytic replacement of follicles).

The serology protocol involved collecting blood on arrival at 11 to 12 days of age, and from all pigs at 0, 7, 14, 21, 28, and 35 DPIs. Serum antibodies to PRRSV were assayed using Herd Check PRRSV ELISA (IDEXX Laboratories, Westbrook, Mass.). Serum antibodies to PPV were detected by a hemagglutination inhibition (HI) assay (H. S. Joo et al., "A standardized haemagglutination inhibition test for porcine parvovirus antibody," Aust. Vet. J. 52:422-424 (1976)). Serum antibodies to PCV2 were detected by a modified indirect ELISA based on the recombinant ORF2 protein of PCV2 (P. Nawagitgul et al., "Modified indirect porcine circovirus (PCV) type 2-based and recombinant capsid protein (ORF2)-based ELISA for the detection of antibodies to PCV," Immunol. Clin. Diagn. Lab Immunol. 1:33-40 (2002)). A partially purified PCV2 antigen was prepared from Hi Five cells (Invitrogen, Carlsbad, Calif.) infected with recombinant baculovirus containing the major capsid ORF2 protein of PCV2 (P. Nawagitgul et al., "Open reading frame 2 of porcine circovirus type 2 encodes a major capsid protein," J. Gen. Virol. 81:2281-2287 (2000)). Cell lysates of Hi Five cells infected with wild-type baculovirus were prepared similarly and served as negative control antigen. The Immulon 2 HB polystyrene microtiter plates (Dynex Technologies Inc, Chantilly, Va.) were coated with optimal concentrations of positive and negative antigens at 4° C. for 36 hrs. One hundred µl of each serum sample diluted 1:100 in 5% milk diluent (Kirkegaard & Perry Laboratories, Inc.) was added into each well. The serum samples were tested in quadruplicate: 2 wells for negative control antigen and 2 parallel wells for PCV2 antigen. Positive control and negative control sera were included in each plate. The sera were incubated at 37° C. for 30 min. and then washed 5 times with 0.1 M PBS buffer containing 0.1% Tween-20. A peroxidase-labeled secondary anti-swine IgG (Sigma Co, St. Louis, Mo.) was incubated at 37° C. for 30 min. The plates were washed again and incubated with 2,2'-azino-di-(3-ethylbenzthiazoline-6-sulfonate) (Kirkegaard & Perry Laboratories Inc) at 37° C. for 15 min. for color development. The optical density (OD) was read at 405 nm. The corrected OD of each tested and control sera was calculated by subtraction of mean OD value of the wells containing negative antigen from that of the parallel wells containing PCV2 antigen. The data was normalized by dividing the corrected OD value of a tested serum sample (S) with that of the positive control serum (P) and reported as S/P ratios. The samples with S/P ratios $\leq 0.12$, 0.12 to 0.2, and >0.2 were considered as negative, equivocal and positive, respectively.

From the results of the clinical evaluation, none of the control and inoculated pigs showed obvious signs of disease resembling those of clinical PMWS. There was no difference in weight gain or mean rectal temperatures between any of the four groups. The control pigs of Group 1 remained normal throughout the experiment. There was mild transient respiratory disease observed in the majority of the pigs in PCV2 DNA-transfected and PCV2 virus-infected groups from 8 to 14 DPI. This was characterized by mild dyspnea (clinical respiratory scores of 1 to 2) of one-to-two days duration in individual pigs and 5-6 days duration for the group.

There were no gross lesions observed in the control pigs at necropsy. Pigs in the three inoculated groups had gross lesions limited to the lungs and lymph nodes (see Table 3, below). The lesions were similar among pigs in the PCV2 plasmid DNA-transfected and PCV2 virus-infected groups. Lungs failed to collapse and had random, multifocal, moderately well-demarcated areas of tan-to-purple consolidation involving 0-2% of the lung (FIG. 3) at 21 DPI, and 0-13% of the lung at 35 DPI. Lymph nodes were systemically enlarged 2 to 5 times normal size, firm, and tan (FIG. 3) at both 21 and 35 DPI in most of the pigs from all three PCV2-inoculated groups.

Microscopic examination revealed no lesions in any tissues of the control pigs except for the livers. Eight of ten control pigs had very mild multifocal lymphoplasmacytic inflammation predominately in the periportal regions of the liver as is commonly observed in normal pigs and considered normal background (P. G. Halbur et al, 2001, supra).

Figure 3A:
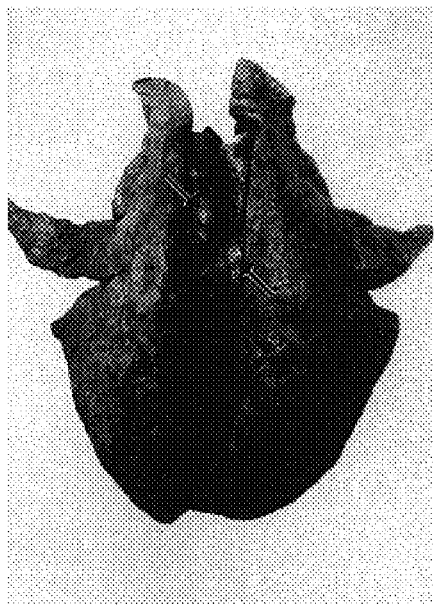
FIG. 3A shows the lungs from a pig inoculated by intralymphoid route with PCV2 DNA at 21 DPI. The lungs are rubbery, failed to collapse, and are mottled tan-red. Tracheobronchial lymph nodes are markedly enlarged and tan (arrows).
Figure 3B:
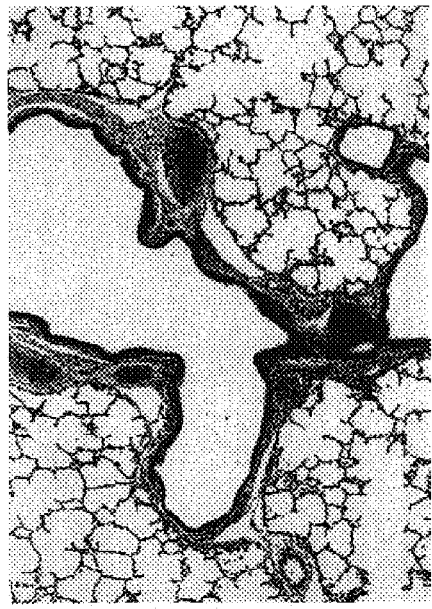
FIG. 3B represents a microscopic section of a normal lung from a control pig (25×).
Figure 3C:
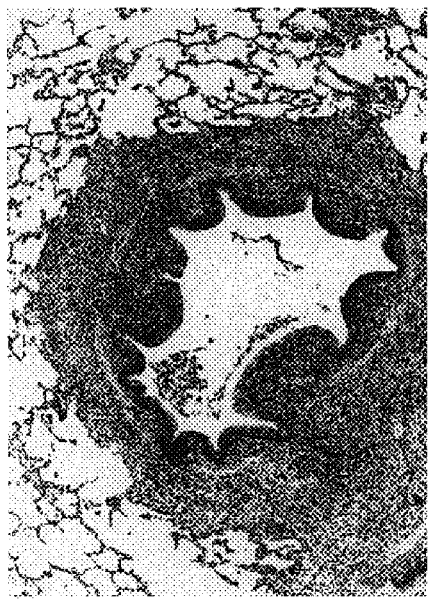
FIG. 3C represents a microscopic section of the lung from the pig in FIG. 3A. Note the peribronchiolar lymphohistiocytic inflammation and mild necrotizing bronchiolitis (25×).

Pigs from the two PCV2 plasmid DNA-transfected groups (intrahepatic and intralymphoid) and the PCV2 virus-infected group (intranasal) had similar lesions in brain, lung, heart, kidney, lymphoid tissues (tonsil, lymph nodes, spleen), ileum, and liver (see Table 4, below). Brain lesions were observed in 23/30 of the pigs from the three inoculated groups and were characterized as mild-to-moderate multifocal lymphoplasmacytic meningoencephalitis with perivascular cuffing and gliosis. Lung lesions were observed in 28/30 PCV2-inoculated pigs and characterized as mild-to-moderate peribronchiolar lymphoplasmacytic and histiocytic bronchointerstitial pneumonia (FIG. 3C). One pig from the PCV2 virus-infected Group 2 necropsied at 21 DPI, and one pig each from the two PCV2 plasmid DNA-transfected groups necropsied at 35 DPI had ulcerative and proliferative bronchiolitis with fibroplasia and granulomatous inflammation in the lamina propria and peribronchiolar regions of bronchi. Mild multifocal lymphoplasmacytic myocarditis was also observed in 18/30 PCV2-inoculated pigs. In 14/30 of the PCV2-inoculated pigs, mild-to-moderate multifocal lymphoplasmacytic interstitial nephritis was observed. No lesions were observed in the thymuses. Mild-to-moderate lymphoid depletion (FIG. 4B) and histiocytic replacement of follicles was observed in the tonsil of 8/30, in the spleen of 7/30, and in the lymph nodes of 26/30 of the PCV2-inoculated pigs. Moderate granulomatous lymphadenitis with giant cells (FIG. 4C) was observed at 21 DPI in three pigs inoculated intranasally with PCV2 virus, and in one pig at 35 DPI in each of the PCV2 plasmid DNA-transfected groups. Mild lymphoplasmacytic and histiocytic enterocolitis were observed in 3/5 pigs in the PCV2 virus-infected group, in 3/5 pigs in the PCV2 plasmid DNA intrahepatically-transfected group, and 1/5 pigs in the PCV2 plasmid DNA intralymphoid-transfected group at 35 DPI. One pig in each of the PCV2 plasmid DNA-transfected groups had mild lymphoid depletion with histiocytic replacement and low numbers of giant cells in the Peyer's patches. Mild-to-moderate lymphoplasmacytic hepatitis was observed in 29/30 of the three PCV2-inoculated pigs. Low numbers of widely scattered individually necrotic hepatocytes surrounded by lymphohistiocytic inflammation was observed in one pig in each of the PCV2 plasmid DNA-transfected groups at 21 DPI. Lesions in other tissues were unremarkable.

Microscopic lesions in the lung, liver and lymph nodes were scored according to published scoring systems (Table 4, below) (P. G. Halbur et al., 2001, supra; P. G. Halbur et al., 1995, supra). There were no acceptable scoring systems for other tissues and organs. The average scores of lesions in lung and lymph nodes in pigs of the three PCV2-inoculated groups were statistically different from those in the control pigs of Group 1. The average scores of the liver lesions in pigs of the three PCV2-inoculated groups are not statistically different from those of control pigs.

TABLE 3

Gross Lesions of Lung and Lymph Nodes in Control and PCV2-Inoculated Pigs

| Group | Inocula | Route of Inoculation | 21 DPI Lymph Nodes | 21 DPI Lung | 35 DPI Lymph Nodes | 35 DPI Lung |
|---|---|---|---|---|---|---|
| 1 | None | | 0/5[a] | 0/5 | 0/5 | 0/5 |
| 2 | PCV2 live virus[b] | Intranasal | 5/5 | 1/5(0-1)[c] | 5/5 | 4/5(0-5) |
| 3 | PCV2 DNA[d] | Intrahepatic | 2/5 | 2/5(0-2) | 5/5 | 2/5(0-13) |
| 4 | PCV2 DNA[d] | Intralymphoid | 4/5 | 5/5(0-1) | 3/5 | 1/5(0-9) |

[a]Five pigs from each group were necropsied at 21 DPI, and the remaining 5 pigs were necropsied at 35 DPI. Number positive/number tested.
[b]A biologically pure and homogeneous PCV2 virus stock generated by transfection of PK-15 cells with PCV2 molecular DNA clone.
[c]Number with lesions/number tested (range of the estimated percent of the lung affected by grossly visible pneumonia lesions, 0-100%)
[d]Cloned PCV2 genomic DNA in pSK plasmid.

TABLE 4

Distribution of Histopathological Lesions in Control and PCV2-Inoculated Pigs

| Group | Inocula | Route of Inoculation | DPI[a] | Lung[b] | Liver[c] | LN[d] | Spleen | Thymus | Ileum | Brain | Heart | Kidney | Tonsil |
|---|---|---|---|---|---|---|---|---|---|---|---|---|---|
| 1 | None | | 21 | 0/5(0.0) | 4/5(0.8) | 0/5(0.0) | 0/5 | 0/5 | 0/5 | 0/5 | 0/5 | 0/5 | 0/5 |
| | | | 35 | 0/5(0.0) | 4/5(0.8) | 0/5(0.0) | 0/5 | 0/5 | 0/5 | 0/5 | 0/5 | 0/5 | 0/5 |
| 2 | PCV2 virus | Intranasal | 21 | 5/5(1.6) | 5/5(1.2) | 3/5(1.2) | 1/5 | 0/5 | 0/5 | 4/5 | 3/5 | 1/5 | 0/5 |
| | | | 35 | 3/5(0.6) | 4/5(1.0) | 4/5(0.8) | 3/5 | 0/5 | 3/5 | 4/5 | 0/5 | 1/5 | 3/5 |

TABLE 4-continued

Distribution of Histopathological Lesions in Control and PCV2-Inoculated Pigs

| Group | Inocula | Route of Inoculation | DPI[a] | Lung[b] | Liver[c] | LN[d] | Spleen | Thymus | Ileum | Brain | Heart | Kidney | Tonsil |
|---|---|---|---|---|---|---|---|---|---|---|---|---|---|
| 3 | PCV2 DNA | Intrahepatic | 21 | 5/5(1.0) | 5/5(1.0) | 5/5(1.0) | 1/5 | 0/5 | 0/5 | 5/5 | 4/5 | 1/5 | 0/5 |
|   |   |   | 35 | 5/5(1.2) | 5/5(1.0) | 4/5(1.0) | 2/5 | 0/5 | 3/5 | 3/5 | 4/5 | 5/5 | 3/5 |
| 4 | PCV2 DNA | Intralymphoid | 21 | 5/5(1.2) | 5/5(1.0) | 5/5(0.8) | 0/5 | 0/5 | 0/5 | 4/5 | 4/5 | 3/5 | 0/5 |
|   |   |   | 35 | 5/5(1.0) | 5/5(1.2) | 5/5(1.4) | 0/5 | 0/5 | 1/5 | 3/5 | 3/5 | 3/5 | 2/5 |

[a]Days postinoculation (DPI): 5 animals from each group were necropsied at 21 DPI and the remaining 5 animals from each group were necropsied at 35 DPI
[b]Number positive/number tested (Average histological lung score: 0 = normal, 1 = mild interstitial pneumonia, 2 = moderate, 3 = severe)
[c]Number positive/number tested (Average histological liver score: 0 = normal, 1 = mild hepatitis, 2 = moderate, 3 = severe)
[d]Number positive/number tested (Average histological lymphoid (LN) depletion score: 0 = normal, 1 = mild, 2 = moderate, 3 = severe)

EXAMPLE 8

Immunohistochemistry

Immunohistochemistry (IHC) detection of PCV2-specific antigen was performed on all tissues collected during necropsies at DPIs 21 and 35. A rabbit polyclonal PCV2-specific antiserum was used for the IHC, and the general procedures have been previously described (S. D. Sorden et al., 1999, supra).

Figure 3D:
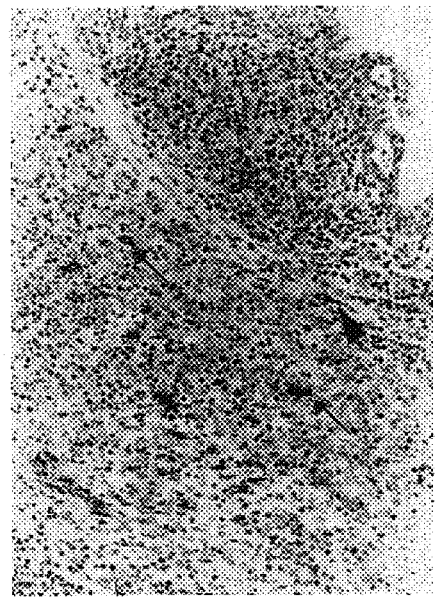
FIG. 3D illustrates the immunohistochemical staining of the lung in FIG. 3A. Note the PCV2 antigen in macrophages (arrows) and fibroblast-like cells (arrow heads) around airways (64×).
Figure 5:
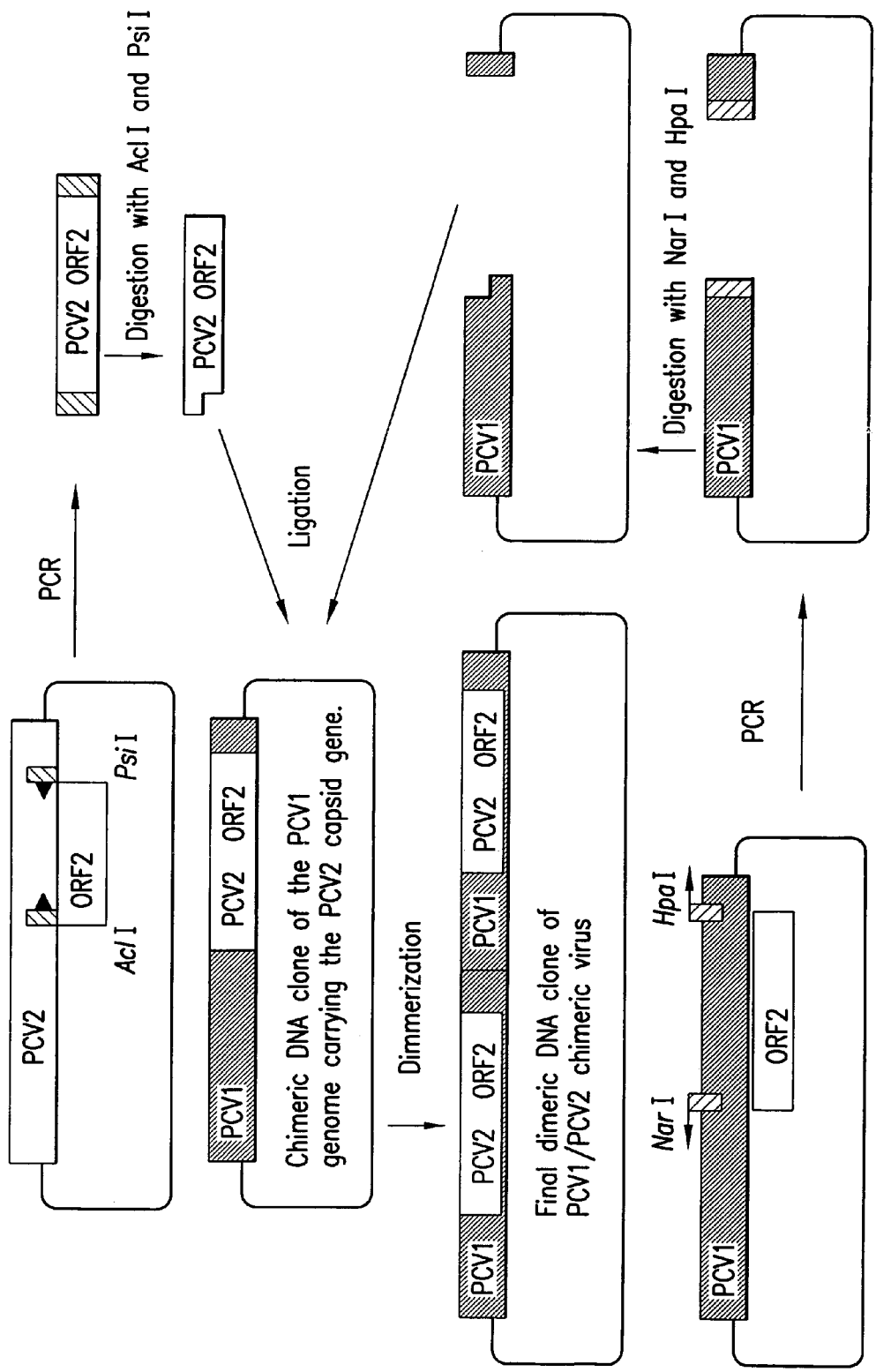
FIG. 5 illustrates the construction of a chimeric PCV1-2 (PCV1/PCV2) DNA clone with the nonpathogenic PCV1 genome carrying the immunogenic ORF2 capsid gene of the pathogenic PCV2. The dimmerized DNA clone is used for in vitro transfection of PK-15 cells to produce live chimeric virus expressing ORF2 protein of PCV2, and in vivo animal experiments to confirm activity.

For the detection and tissue distribution of PCV2 antigen, IHC staining of PCV2 antigen was done on brain, lungs, turbinate, heart, kidneys, tonsil, lymph nodes, spleen, thymus, ileum, liver, gall bladder and pancreas of all pigs necropsied at 21 and 35 DPI. All tissues from the control pigs were negative for PCV2 antigen. Tissue distribution of PCV2 antigen in the three PCV2-inoculated groups was similar (see Table 5, below). In the brain, the PCV2 antigen was found predominately in mononuclear cells, fibroblast-like cells, and endothelial cells in the meninges and choroid plexus and less often in endothelial cells and perivascular mononuclear cells in the cerebrum and cerebellum. In the lungs, PCV2 antigen was detected within alveolar and septal macrophages and in fibroblast-like cells in the lamina propria of airways (FIG. 3D). In the heart, PCV2 antigen was detected in widely scattered macrophages and endothelial cells. In kidneys, PCV2 antigen was detected within tubular epithelial cells and mononuclear cells in the interstitium. In the lymphoid tissues (lymph nodes, spleen, tonsil, and Peyer's patches), PCV2 antigen was detected primarily within macrophages and dendritic-like cells and giant cells within follicles (FIG. 4D). PCV2 antigen was also detected within macrophages in the lamina propria of the small intestine. In the liver, PCV2 antigen was detected within mononuclear cells and Kupffer cells. PCV2 antigen was not detected in turbinate, thymus, or gall bladder.

EXAMPLE 9

Construction of the Nonpathogenic PCV1 Infectious DNA Clone

The procedure used to construct a PCV1 infectious DNA clone is essentially the same as that described herein for PCV2. A pair of PCR primers, KPNPCV1.U set forth in SEQ ID NO:7 and KPNPCV1.L set forth in SEQ ID NO:8 (see Table 6, below), was designed based on the published sequence of PCV1. This pair of primers amplifies the complete genome of PCV1 with an overlapping region containing the unique KpnI restriction enzyme site. The DNA of the PCV1 virus was extracted from the contaminated ATCC PK-15 cell line that was obtained from the American Type Culture Collection (ATCC accession number CCL-33). The PCV1 DNA was extracted from the ATCC PK-15 cells persistently infected with PCV1, using the QIAmp DNA minikit (Qiagen, Inc., Valencia, Calif.). The extracted DNA was amplified by PCR with AmpliTaq Gold Polymerase (Perkin-Elmer, Norwalk, Conn.). The PCR cycles consisted of an initial step of 95° C. for 10 min., followed by 35 cycles of denaturation at 94° C. for 1 min., annealing at 48° C. for 1 min., extension at 72° C. for 2 min., and a final extension at 72° C. for 7 min. The PCR product of expected size was separated by gel electrophoresis and purified by the glassmilk procedure using a Geneclean Kit (Bio 101, Inc., La Jolla, Calif.). The purified PCR product containing the complete PCV1 genome was first ligated into the advanTAge plasmid vector (Clontech, Palo Alto, Calif.). Escherichia coli DH5α competent cells were used for transformation. The recombinant plasmids were verified by restriction enzyme digestion. The full length PCV1 genomic DNA was excised from the advanTAge vector by digestion

TABLE 5

Detection and Distribution of PCV2-Specific Antigen by Immunohistochemistry in Control and PCV2-Inoculated Pigs

| Group | Inocula | Route of Inoculation | DPI[a] | Lung | Liver | LN | Spleen | Thymus | Ileum | Brain | Heart | Kidney | Tonsil |
|---|---|---|---|---|---|---|---|---|---|---|---|---|---|
| 1 | None |   | 21 | 0/5[b] | 0/5 | 0/5 | 0/5 | 0/5 | 0/5 | 0/5 | 0/5 | 0/5 | 0/5 |
|   |   |   | 35 | 0/5 | 0/5 | 0/5 | 0/5 | 0/5 | 0/5 | 0/5 | 0/5 | 0/5 | 0/5 |
| 2 | PCV2 virus | Intranasal | 21 | 4/5 | 5/5 | 5/5 | 3/5 | 0/5 | 3/5 | 3/5 | 1/5 | 1/5 | 2/5 |
|   |   |   | 35 | 1/5 | 2/5 | 3/5 | 2/5 | 0/5 | 0/5 | 2/5 | 0/5 | 0/5 | 0/5 |
| 3 | PCV2 DNA | Intrahepatic | 21 | 5/5 | 5/5 | 5/5 | 5/5 | 0/5 | 0/5 | 5/5 | 1/5 | 0/5 | 2/5 |
|   |   |   | 35 | 4/5 | 4/5 | 3/5 | 4/5 | 0/5 | 3/5 | 4/5 | 2/5 | 2/5 | 3/5 |
| 4 | PCV2 DNA | Intralymphoid | 21 | 4/5 | 4/5 | 5/5 | 4/5 | 0/5 | 3/5 | 3/5 | 0/5 | 0/5 | 3/5 |
|   |   |   | 35 | 3/5 | 4/5 | 5/5 | 4/5 | 0/5 | 2/5 | 3/5 | 1/5 | 0/5 | 4/5 |

[a]Days postinoculation (DPI): 5 animals from each group were necropsied at 21 DPI and the remaining 5 animals from each group were necropsied at 35 DPI
[b]Number positive/number tested.

with KpnI restriction enzyme. The full-length PCV1 genomic DNA was ligated into pBluescript SK(+) (pSK) vector (Stratagene, La Jolla, Calif.) with T4 DNA ligase at 37° C. overnight. Recombinant plasmids containing the full-length PCV1 genome were isolated with a Qiagen plasmid mini kit (Qiagen, Valencia, Calif.) and were verified by restriction enzyme digestion and DNA sequencing. The full-length PCV1 genomic DNA was excised from the pSK vector by KpnI digestion, and dimmerized to make the PCV1 infectious DNA clone as described above in Example 2 for the PCV2 infectious clone. These tandem dimers were made because the dimmerized tandem DNA clones are advantageously found to be more efficient to transfect cells and produce infectious virions. To make the tandem dimer of the PCV1 DNA, the digested PCV1 genomic DNA was ligated with T4 DNA ligase at 37° C. for only 10 min., which favors the production of tandem dimers. The tandem dimers were subsequently cloned into pBluescript SK(+) (pSK) vector (Stratagene, La Jolla, Calif.). Recombinant plasmids containing tandem dimers of PCV1 genome (herein referred to as "PCV1 DNA clone") were confirmed by PCR, restriction enzyme digestion, and DNA sequencing. The DNA concentration of the recombinant plasmids was determined spectrophotometrically.

TABLE 6

Oligonucleotide Primers Employed in this Invention

| Primer | Direction | Primer Sequence | Application |
|---|---|---|---|
| | | Construction primers: | |
| KPNPCV1.U. | >[a] | 5'-TTTGGTACCCGAAGGCCGATT-'3 (corresponds to SEQ ID NO:7) | PCV1 DNA clone construction |
| KPNPCV1.L. | < | 5'-ATTGGTACCTCCGTGGATTGTTCT-'3 (corresponds to SEQ ID NO:8) | PCV1 DNA clone construction |
| Hpa I-2 | < | 5'-GAAGTTAACCCTAAATGAATAAAAATAAAAACCATTACG-'3 (corresponds to SEQ ID NO:9) | PCV1-2 DNA clone construction |
| Nar I-3 | > | 5'-GGTGGCGCCTCCTTGGATACGTCATCCTATAAAAGTG-'3 (corresponds to SEQ ID NO:10) | PCV1-2 DNA clone construction |
| Psi I-5 | > | 5'-AGGTTATAAGTGGGGGGTCTTTAAGATTAA-'3 (corresponds to SEQ ID NO:11) | PCV1-2 DNA clone construction |
| Acl I-6 | < | 5'-GGAAACGTTACCGCAGAAGAAGACACC-'3 (corresponds to SEQ ID NO:12) | PCV1-2 DNA clone construction |
| Bgl-II-ORF2 | > | 5'-ACTATAGATCTTTATTCATTTAGAGGGTCTTTCAG-'3 (corresponds to SEQ ID NO:13) | PCV2-1 DNA clone construction |
| SpH-I-ORF2 | < | 5'-TACGGGCATGCATGACGTGGCCAAGGAGG-'3 (corresponds to SEQ ID NO:14) | PCV2-1 DNA clone construction |
| Bgl-II-PCV2 | < | 5'-AGACGAGATCTATGAATAATAAAAACCATTACGAAG-'3 (corresponds to SEQ ID NO:15) | PCV2-1 DNA clone construction |
| SpH-I-PCV2 | > | 5'-CGTAAGCATGCAGCTGAAAACGAAAGAAGTG-'3 (corresponds to SEQ ID NO:16) | PCV2-1 DNA clone construction |
| | | Detection primers: | |
| MCV1 | > | 5'-GCTGAACTTTTGAAAGTGAGCGGG-'3 (corresponds to SEQ ID NO:17) | PCV1 and PCV2 detection |
| MCV2 | < | 5'-TCACACAGTCTCAGTAGATCATCCCA-'3 (corresponds to SEQ ID NO:18) | PCV1 and PCV2 detection |
| Orf.PCV1 | < | 5'-CCAACTTTGTAACCCCCTCCA-'3 (corresponds to SEQ ID NO:19) | PCV1 and PCV2-1 detection |

TABLE 6-continued Oligonucleotide Primers Employed in this Invention

| Primer | Direction | Primer Sequence | Application |
|---|---|---|---|
| Gen.PCV1 | > | 5'-GTGGACCCACCCTGTGCC-'3 (corresponds to SEQ ID NO:20) | PCV1 and PCV1-2 detection |
| Nested.Orf.PCV1 | < | 5'-CCAGCTGTGGCTCCATTTAA-'3 (corresponds to SEQ ID NO:21) | PCV1 and PCV2-1 detection |
| Nested.Gen.PCV1 | > | 5'-TTCCCATATAAAATAAATTACTGAGTCTT-'3 (corresponds to SEQ ID NO:22) | PCV1 and PCV1-2 detection |
| Orf.PCV2 | < | 5'-CAGTCAGAACGCCCTCCTG-'3 (corresponds to SEQ ID NO:23) | PCV2 and PCV1-2 detection |
| Gen.PCV2 | > | 5'-CCTAGAAACAAGTGGTGGGATG-'3 (corresponds to SEQ ID NO:24) | PCV2 and PCV2-1 detection |
| Nested.Orf.PCV2 | < | 5'-TTGTAACAAAGGCCACAGC-'3 (corresponds to SEQ ID NO:25) | PCV2 and PCV1-2 detection |
| Nested.Gen.PCV2 | > | 5'-GTGTGATCGATATCCATTGACTG-'3 (corresponds to SEQ ID NO:26) | PCV2 and PCV2-1 detection |

[a]Primer direction.

EXAMPLE 10

Figure 6:
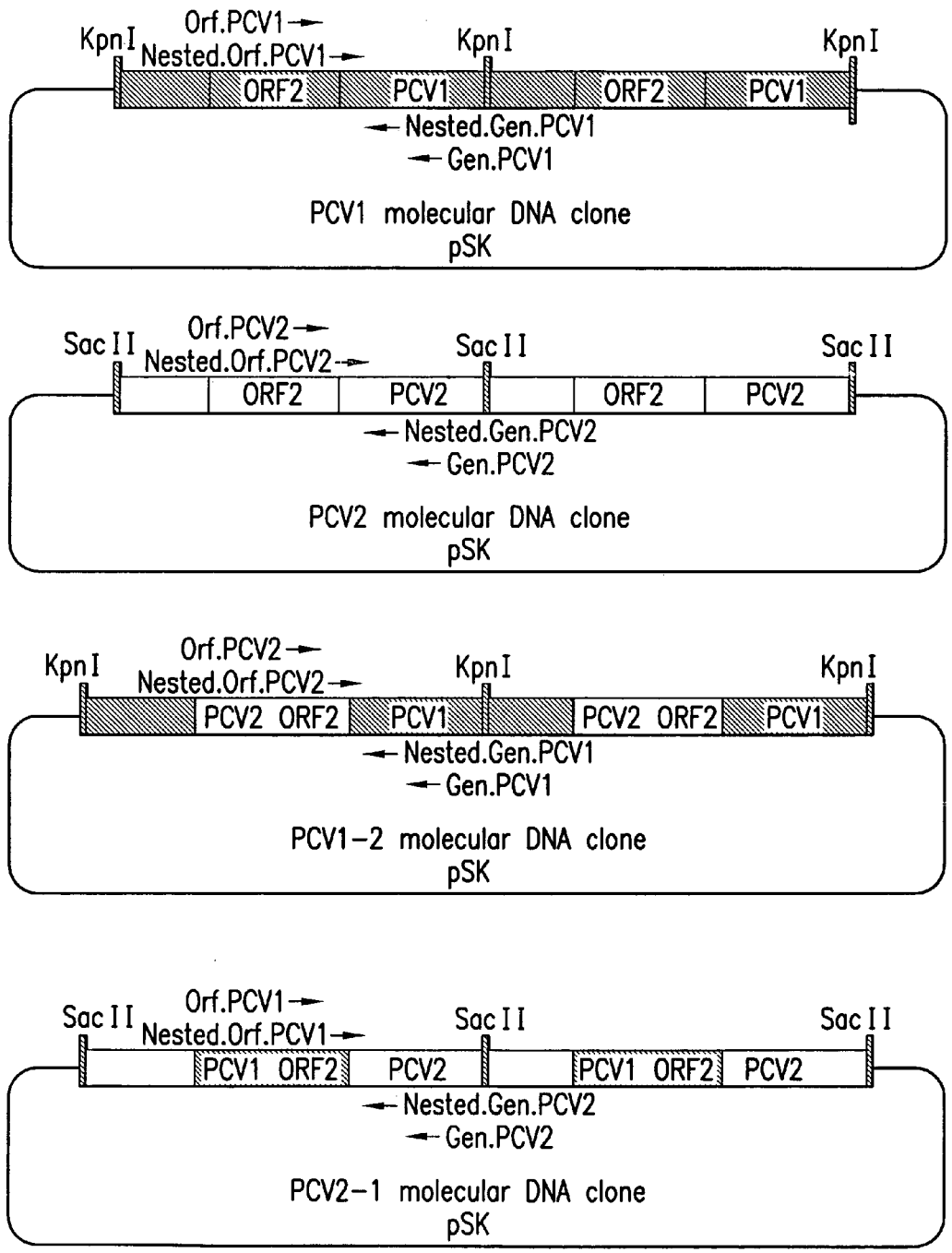
FIG. 6 represents the construction and organization of the infectious PCV1, PCV2, chimeric PCV1-2 and reciprocal chimeric PCV2-1 molecular DNA clones. The PCV2 DNA clone is constructed by ligating two full-length linear PCV2 genomes in tandem into the Bluescript SK vector (pSK) by the general methods described previously (M. Fenaux et al., 2002, supra). PCV1 DNA clone is constructed by ligating two full-length linear PCV1 genomes in tandem into pSK vector. Chimeric PCV1-2 DNA clone is constructed by replacing the ORF2 capsid gene of PCV1 with that of the PCV2 in the nonpathogenic PCV1 genomic backbone in pSK vector. Reciprocal chimeric PCV2-1 DNA clone is constructed by replacing the ORF2 capsid gene of the pathogenic PCV2 with that of the nonpathogenic PCV1 in the pathogenic PCV2 genomic backbone in pSK vector. Both chimeric clones are dimmers in pSK vector. The arrows represent the relative locations of the PCR primers for the detection of PCV1, PCV2, PCV1-2 and PCV2-1 viremia in inoculated animals.
Figure 7A:
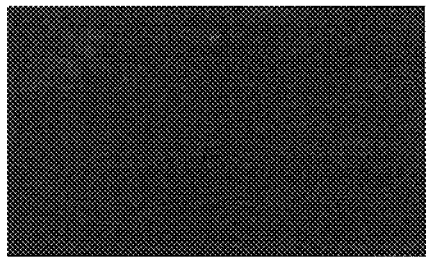
FIGS. 7A-7J demonstrate that the PCV1, PCV2, chimeric PCV1-2 and reciprocal chimeric PCV2-1 DNA clones are infectious and express respective viral antigens when transfected in vitro in PK-15 cells. The left panel (7A, 7C, 7E, 7G and 7I) is stained with monoclonal antibody against the PCV1 ORF2. The right panel (7B, 7D, 7F, 7H and 7J) is stained with antibody against PCV2. Panels 7A and 7B are mock transfected PK-15 cells. Panels 7C and 7D are PK-15 cells transfected with the PCV1 DNA clone. Panels 7E and 7F are PK-15 cells transfected with the PCV2 DNA clone. Panels 7G and 7H are PK-15 cells transfected with the chimeric PCV1-2 DNA clone. Panels 7I and 7J are PK-15 cells transfected with the reciprocal chimeric PCV2-1 DNA clone.
Figure 7B:
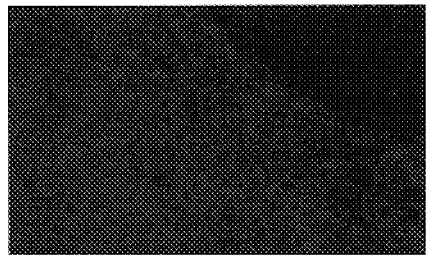
Figure 7C:
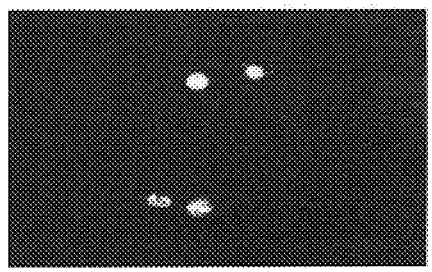
Figure 7D:
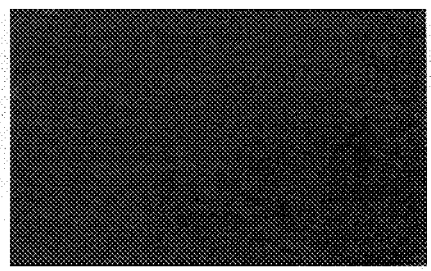
Figure 7E:
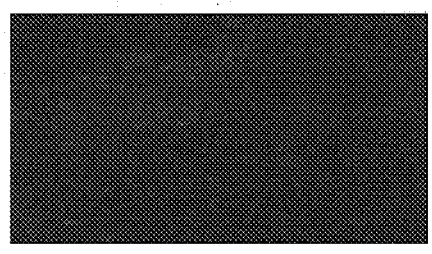
Figure 7F:
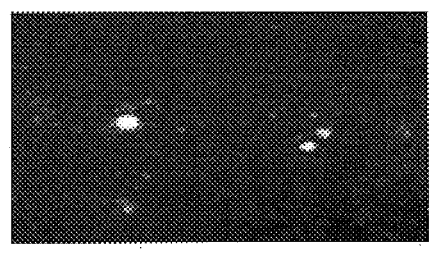
Figure 7G:
Figure 7H:
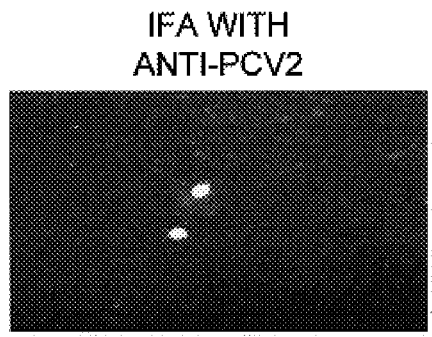
Figure 7I:
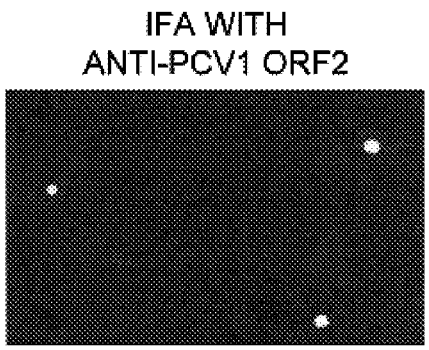
Figure 7J:

Evaluation of Infectivity of the PCV1 DNA Clone when Transfected into PK-15 Cells Free of Virus Contamination The infectivity of the PCV1 molecular DNA clone was determined by in vitro transfection of the PK-15 cells. IFA with PCV1 specific monoclonal antibody (a gift from Dr. Gordon Allan, Belfast, U.K.) confirmed that the PCV1 molecular DNA clone is infectious in PK-15 cells. PCV1-specific antigen was visualized by IFA in the nucleus, and to a lesser degree cytoplasm of the transfected cells. The cells mock-transfected with the empty pSK vector remained negative for PCV1 antigen.

EXAMPLE 11

Construction of a Chimeric PCV1-2 Viral DNA Clone

A chimeric virus was constructed between the nonpathogenic PCV1 and the PMWS-associated PCV2 by using infectious DNA clones of PCV1 and PCV2. To construct a chimeric PCV1-2 DNA clone, the ORF2 capsid gene of the nonpathogenic PCV1 was removed from the PCV1 infectious DNA clone, and replaced with the immunogenic ORF2 capsid gene of the pathogenic PCV2 in the genome backbone of PCV1 (see FIGS. 5 and 6). Two pairs of PCR primers were designed. The first primer pair for PCV2 ORF2, Psi I-5 set forth in SEQ ID NO:11 and Acl I-6 set forth in SEQ ID NO:12, was designed with point mutations at the 5' ends of the primers to create restriction enzyme sites AclI and PsiI to amplify the ORF2 gene of PCV2 and introduce flanking PsiI and AclI restriction enzyme sites by point mutation. The PCR reaction for the PCV2 ORF2 amplification consisted of an initial step at 95° C. for 9 min., followed by 38 cycles of denaturation at 95° C. for 1 min., annealing at 48° C. for 1 min., extension at 72° C. for 1 min., and a final extension at 72° C. for 7 min.

A second pair of PCR primers, Hpa I-2 set forth in SEQ ID NO:9 and Nar I-3 set forth in SEQ ID NO:10, was designed for the amplification of the pSK+ vector and its PCV1 genome insert. Point mutations were introduced at the 5' ends of the PCR primers to create flanking restriction enzyme sites NarI and HpaI. This primer pair amplified the pSK+ vector and its insert PCV1 genomic DNA lacking the ORF2 capsid gene, that is, the PCV1 genome minus the PCV1 ORF2 (pSK-PCV1 ΔORF2) by using the PCV1 infectious DNA clone as the PCR template. The PCR reaction consisted of an initial step at 95° C. for 9 min., followed by 38 cycles of denaturation at 95° C. for 1 min., annealing at 50° C. for 1 min., extension at 72° C. for 3.5 min., and a final extension at 72° C. for 7 min. The PCV2 ORF2 PCR product was digested with the AclI and PsiI to remove the introduced point mutations. The pSK-PCV1 ΔORF2 product (the pSK vector-PCV1 genome PCR product lacking ORF2 gene of PCV1) was digested with the NarI and HpaI to remove the PCR introduced point mutations. The latter digestion produced a sticky end and a blunt end complementary to the PCV2 ORF2 PCR product digested by the AclI and PsiI restriction enzymes. The digested PCV2 ORF2 product and the ORF2-deleted pSK-PCV1 product were ligated with T4 DNA ligase to form the chimeric PCV1-2 genomic DNA clone, in which the ORF2 gene of PCV1 is replaced with the ORF2 gene of PCV2. Once the two PCR products were digested and religated, all the PCR introduced point mutations used to facilitate cloning were removed in the resulting chimeric clone. *Escherichia coli*

DH5α competent cells were transformed. The recombinant plasmids containing the chimeric DNA clone were isolated and confirmed by PCR, restriction enzyme digestion and partial DNA sequencing. The full-length chimeric PCV1-2 genome was excised from the pSK+ vector (the recombinant plasmid) with KpnI digestion. The chimeric DNA genome was then dimmerized by a short 10-minute ligation reaction with T4 DNA ligase that favors the formation of linear dimers to produce the PCV 1-2 chimeric infectious DNA clone (FIG. 6). The recombinant plasmids containing two copies of the chimeric viral genome were confirmed by PCR, restriction enzyme digestion and DNA sequencing.

EXAMPLE 12

Evaluation of In Vitro Infectivity of PCV1-2 Chimeric DNA Clone

The viability of the chimeric PCV DNA clone (nonpathogenic PCV1 with the immunogenic capsid gene of PCV2) was tested in PK-15 cells. When PK-15 cells were transfected with the chimeric viral DNA clone, viral antigen specific for PCV2 ORF2 capsid was detected by IFA at about 2 days post-transfection. The PCV1 capsid antigen was not detected in transfected cells. This experiment indicated that the chimeric DNA clone is infectious in vitro, is replicating in PK-15 cells and producing the immunogenic capsid protein of PCV2.

EXAMPLE 13

Construction of a Reciprocal Chimeric PCV2-1 DNA Clone

To construct a reciprocal PCV2-1 chimeric DNA clone, the ORF2 capsid gene of PCV2 is replaced by that of the non-pathogenic PCV1 in the genome backbone of the pathogenic PCV2 (FIG. 6). Two PCR primer pairs were designed: the pair, Bgl-II-ORF2 set forth in SEQ ID NO:13 and SpH-I-ORF2 set forth in SEQ ID NO:14, amplifies the PCV1 ORF2 gene and introduces flanking BglII and SpHI restriction enzyme sites by point mutation. The second PCR primer pair, Bgl-II-PCV2 set forth in SEQ ID NO:15 and SpH-I-PCV2 set forth in SEQ ID NO:16, amplified the pSK vector and the PCV2 genome minus the ORF2 gene (pSK-PCV2 ΔORF2) by using the PCV2 infectious DNA clone as the PCR template, and introduced flanking restriction enzymes sites BglII and SpHI by point mutation. The pSK-PCV2 ΔORF2 product and the PCV1 ORF2 PCR product were digested by BglII and SpHI restriction enzymes to produce complementary sticky and blunt ends ligated together. After transformation into *E. Coli* cells, the authentic recombinant plasmids were isolated and confirmed by enzyme digestion and partial DNA sequencing. The full-length reciprocal chimeric PCV2-1 genome was excised from the recombinant plasmid by SacII digestion, and dimmerized as described herein to produce the reciprocal chimeric PCV2-1 infectious clone.

EXAMPLE 14

In vitro Transfection of PK-15 Cells with PCV1, PCV2, PCV1-2 and PCV2-1 DNA Clones The infectivity of PCV2 clone in vitro and in vivo has been demonstrated in the above Examples 3-5. To test the infectivity of the PCV1 and two chimeric clones in vitro, PK-15 cells free of PCV1 contamination prepared per the method of Example 1 were grown in 8-well LabTek chambers slides (Nalge Nunc Int., Denmark). When the PK-15 cells reached about 80% confluency, cells were transfected with PCV1, PCV2, PCV1-2 and PCV2-1 DNA clones respectively, using the Lipofectamine Plus Reagent according to the protocols supplied by the manufacturer (Life Technologies, Inc.). Mock-transfected cells with empty pSK vector were included as controls. Three days after transfection, the cells were fixed with a solution containing 80% acetone and 20% methanol at 4° C. for 20 min. Evidence of infectivity and virus replication in cells transfected with the PCV1 and PCV2-1 DNA clones were confirmed by indirect immunofluorescence assay (IFA) using monoclonal antibody against PCV1 ORF2 capsid gene, kindly provided by Dr. G. M. Allan (G. M. Allan et al., "Production, preliminary characterization and applications of monoclonal antibodies to porcine circovirus," Vet. Immunol. Immunopathol. 43:357-371 (1994)). The fixed cells were washed with phosphate buffered saline (PBS) and incubated with 1:20 diluted PCV1 monoclonal antibody at 37° C. for 1 hour. The cells were then washed three times with PBS buffer and incubated with fluorescein isothiocyanate (FITC) labeled goat anti-mouse immunoglobulin G (Kirkegaard & Perry Laboratories, Inc., Gaithersburg, Md.) at 37° C. for 45 min. After washing three times with PBS buffer, the slides were mounted with fluoromount-G, coverslipped, and examined under a fluorescence microscope. The infectivity of cells transfected with the PCV2 and the chimeric PCV1-2 DNA clones were confirmed by IFA using antibody specific for PCV2, as previously described in Example 4.

The infectivity of the PCV1, the chimeric PCV1-2 DNA and the reciprocal chimeric PCV2-1 DNA clones were substantiated by the in vitro transfection of PK-15 cells. Two identical copies of the complete PCV1 genome were ligated in tandem into the pSK vector to produce the PCV1 DNA clone (FIG. 6). The chimeric PCV1-2 DNA clone had the ORF2 capsid gene of PCV1 replaced by that of the pathogenic PCV2 in the backbone of the nonpathogenic PCV1 genome. The reciprocal chimeric PCV2-1 DNA clone had the ORF2 capsid gene of PCV2 replaced by that of the nonpathogenic PCV1 in the backbone of the pathogenic PCV2 genome. If infectious in vitro, the chimeric PCV1-2 DNA clone will produce the ORF2 capsid antigen of PCV2 and the reciprocal chimeric PCV2-1 DNA clone will express PCV1 ORF2 capsid antigen in transfected PK-15 cells. The results showed that the PCV1, the chimeric PCV1-2 and the reciprocal chimeric PCV2-1 DNA clones were all surprisingly shown to be infectious when transfected into PK-15 cells and expressed respective viral capsid antigen proteins as demonstrated by IFA using antibodies specific for PCV1 or PCV2. IFA using monoclonal antibodies against PCV1 ORF2 and antibodies against PCV2 confirmed that the PCV1 DNA and the PCV1-2 DNA clones were infectious. IFA using PCV1 ORF2-specific monoclonal antibody showed that the PCV1-2 chimeric DNA clone was also infectious. About 10-20% of the transfected PK-15 cells were positive for PCV1 capsid antigen and PCV2 antigen, and expressed PCV1 ORF2 antigen, within the nucleus of transfected cells (FIG. 7).

EXAMPLE 15

Experimental Inoculation of Pigs with PCV1, PCV2, Chimeric PCV1-2 and Reciprocal Chimeric PCV2-1 DNA Clones To evaluate the immunogenicity and pathogenicity of the chimeric DNA clones, forty specific-pathogen-free (SPF)

pigs of 4-6 weeks of age were randomly assigned into five rooms of 8 animals each. Prior to inoculation, animals were tested for antibodies to PCV, PRRSV, PPV, and swine hepatitis E virus. In addition, pre-inoculation serum samples were tested by PCR for PCV1 and PCV2 nucleic acid to confirm that the pigs are not naturally infected by either of the viruses. The PCV1, PCV2, PCV1-2 and PCV2-1 DNA clones were all inoculated by direct injection of the cloned plasmid DNA into the superficial iliac lymph nodes of pigs. Pigs in Group 1 received phosphate buffered saline (PBS buffer) and served as the negative control. Group 2 pigs were each injected into the superficial iliac lymph nodes with 200 µg of infectious PCV1 DNA clone. Group 3 pigs were each injected with 200 µg of infectious PCV2 DNA clone. Group 4 pigs each received injections of 200 µg of infectious chimeric PCV1-2 DNA clone. Group 5 pigs each received 200 µg of the infectious reciprocal chimeric PCV2-1 DNA clone. All animals were monitored daily for clinical signs of disease. Serum samples were collected from each animal at −2, 7, 14, 21, 28, 35, 42 and 49 days post-inoculation (DPI). At 21 DPI, four randomly selected animals from each group were necropsied. The remaining four animals in each group were necropsied at 49 DPI. Various tissues and organs were collected during necropsy as previously described in Example 7, and processed for histological examination.

The immunogenicity of the PCV1, the PCV2 and the chimeric infectious DNA clones was examined in the pigs. Serum samples collected from all control and inoculated animals at −2 (0), 7, 14, 21, 28, 35, 42 and 49 DPIs were assayed for PCV1, PCV2, PCV1-2 and PCV2-1 viremia by PCR detection of clone-specific DNA sequences, for anti-PCV1 antibody by IFA and for anti-PCV2 ORF2 antibody by ELISA. Prior to inoculation at −2 DPI, animals from all five groups tested negative by PCR for both PCV1 and PCV2 DNA.

Negative control animals were negative for both PCV1 and PCV2 viremia throughout the study (see Table 7, below). Five pigs in the uninoculated control group had detectable PCV2 maternal antibody at −2 DPI and 2 pigs had detectable PCV1 maternal antibodies at 7 DPI (see Table 8, below). The maternal antibodies to both PCV1 and PCV2 in these piglets waned by 21 DPI. No seroconversion to either PCV1 or PCV2 was detected in any of the 8 uninoculated control pigs throughout the study.

In the PCV1 inoculated group, viremia was first detected in an inoculated pig at 7 DPI (Table 7, below), and was last detected at 35 DPI. Five out of 8 animals inoculated with PCV1 infectious DNA clone were positive for PCV1 viremia. Average length of continuous PCV1 viremia was 0.625 weeks. By 21 DPI, all animals in the PCV1 inoculated group had seroconverted to PCV1 and remained positive to PCV1 antibodies until the end of the study at 49 DPI.

The PCV2 DNA clone is shown herein to be infectious in pigs. In the PCV2 DNA clone inoculated group, PCV2 viremia was first detected at 7 DPI (Table 7, below). By 21 DPI, all PCV2 inoculated Group 3 animals were positive for PCV2 viremia. The average length of PCV2 viremia was 2.12 weeks. Two pigs in the PCV2 inoculated group had detectable levels of maternal PCV2 antibodies at 7 DPI (Table 8, below), and the maternal antibodies in these piglets waned by 14 DPI. Seroconversion to PCV2, assayed by a PCV2-specific ELISA, was first detected at 35 DPI. By 42 DPI, all pigs inoculated with PCV2 infectious DNA clone had seroconverted to PCV2.

In Group 4 pigs inoculated with PCV1-2 chimeric infectious DNA clone, viremia specific for the chimeric virus was first detected at 14 DPI (Table 7, below). Four out of 7 inoculated animals became viremic to PCV1-2 between 14 DPI and 42 DPI. The average length of chimeric PCV1-2 viremia was 1 week. One pig had detectable levels of maternal PCV2 antibodies at 7 and 14 DPI, but the maternal antibody waned by 21 DPI (Table 8, below). Seroconversion to PCV2 ORF2-specific antibody first occurred at 28 DPI. By 49 DPI, all pigs inoculated with chimeric PCV1-2 DNA clone had seroconverted to PCV2 ORF2-specific antibody.

In pigs inoculated with the reciprocal chimeric PCV2-1 clone, viral DNA specific for PCV2-1 chimeric virus was not detected in serum samples (Table 7, below). However, by 21 DPI all animals in Group 5 seroconverted to PCV1 antibody. PCR products amplified from selected pigs in each group were sequenced and confirmed to be the authentic respective infectious clones used in the inoculation in each group.

TABLE 7

Detection of Viremia by Nested PCR in Sera of Inoculated and Control Pigs

| | | DPI | | | | | | | |
|---|---|---|---|---|---|---|---|---|---|
| Group | Inoculum | −2 | 7 | 14 | 21 | 28 | 35 | 42 | 49 | Total |
| 1 | PBS[a] | 0/8[b] | 0/8 | 0/8 | 0/8 | 0/4 | 0/4 | 0/4 | 0/4 | 0/8 |
| 2 | PCV1 DNA[c] | 0/8 | 1/8 | 1/8 | 2/8 | 0/4 | 2/4 | 0/4 | 0/4 | 5/8 |
| 3 | PCV2 DNA[c] | 0/8 | 3/8 | 6/8 | 7/8 | 1/4 | 2/4 | 2/4 | 0/4 | 8/8 |
| 4 | PCV1-2 DNA[c] | 0/7 | 0/7 | 1/7 | 2/7 | 2/4 | 2/4 | 2/4 | 0/4 | 4/7 |
| 5 | PCV2-1 DNA[c] | 0/8 | 0/8 | 0/8 | 0/8 | 0/4 | 0/4 | 0/4 | 0/4 | 0/8 |

[a]phosphate buffered saline (PBS) used as negative control
[b]Eight pigs in each group; number positive/number tested
[c]Cloned genomic PCV or chimeric PCV DNA in pSK plasmid

TABLE 8

Seroconversion to Antibodies Against PCV2 in Pigs Inoculated with PCV2 or Chimeric PCV1-2 DNA Clones and Seroconversion to Antibodies Against PCV1 in Pigs Inoculated with PCV1 or PCV2-1 DNA Clones

| | | | DPI[c] | | | | | | | |
|---|---|---|---|---|---|---|---|---|---|---|
| Group | Inoculum[a] | Antibody Tested For[b] | −2 | 7 | 14 | 21 | 28 | 35 | 42 | 49 |
| 1 | PBS | PCV1 | NA | 2/8 | 2/8 | 1/8 | 0/4 | 0/4 | 0/4 | 0/4 |
| | | PCV2 | 5/8 | 5/8 | 2/8 | 0/8 | 0/4 | 0/4 | 0/4 | 0/4 |
| 2 | PCV1 DNA | PCV1 ORF2 | NA | 3/8 | 2/8 | 8/8 | 4/4 | 4/4 | 4/4 | 4/4 |
| 3 | PCV2 DNA | PCV2 complete virus | 3/8 | 2/8 | 0/8 | 0/8 | 0/4 | 3/4 | 4/4 | 4/4 |

TABLE 8-continued

Seroconversion to Antibodies Against PCV2 in Pigs Inoculated
with PCV2 or Chimeric PCV1-2 DNA Clones and
Seroconversion to Antibodies Against PCV1 in Pigs Inoculated
with PCV1 or PCV2-1 DNA Clones

| | | | DPI[c] | | | | | | |
|---|---|---|---|---|---|---|---|---|---|
| Group | Inoculum[a] | Antibody Tested For[b] | −2 | 7 | 14 | 21 | 28 | 35 | 42 | 49 |
| 4 | PCV1-2 DNA | PCV2 complete virus | 2/8 | 1/8 | 1/8 | 0/8 | 1/4 | 1/4 | 3/4 | 4/4 |
| 5 | PCV2-1 DNA | PCV1 ORF2 | NA | 3/8 | 3/8 | 8/8 | 3/4 | 3/4 | 4/4 | 4/4 |

[a]Phosphate buffered saline (PBS) used as negative control. The inocula were cloned genomic PCV and PCV chimeric DNA in pSK plasmid
[b]PCV1 antibody to ORF2 was measured with an indirect immunofluorescence assay specific for PCV1 antigen. PCV2 antibody was measured with an enzyme-linked immunosorbent assay.
[c]Days post inoculation, number positive/number tested.

EXAMPLE 16

Clinical Evaluation

Pigs were weighed on 0 DPI and at the time of necropsies. Rectal temperatures and clinical respiratory scores, ranging from 0 to 6 (0=normal; 6=severe) (P. G. Halbur et al., "Comparison of the pathogenicity of two U.S. porcine reproductive and respiratory syndrome virus isolates with that of the Lelystad virus," Vet. Pathol. 32:648-660 (1995)), were recorded every other day from 0 to 49 DPI. Clinical observations, including evidence of central nervous system disease, liver disease (icterus), muscoloskeletal disease and changes in body condition, were also recorded daily. A team of two people performed all clinical evaluations.

None of the control or inoculated pigs showed obvious signs of the full-spectrum clinical PMWS. There were no differences in weight gain or mean rectal temperatures between any of the groups. One of the pigs from PCV1-2 inoculated Group 3 died one day after inoculation. After necropsy and clinical analysis, no pathogenic agent was detected and death was not associated with the inoculation procedure or the chimeric PCV1-2 virus.

EXAMPLE 17

Gross Pathology and Histopathology

Four pigs from each group were necropsied at 21 and 49 DPI, respectively. The necropsy team was blinded to infection status of the pigs at necropsy. Complete necropsies were performed on all pigs. An estimated percentage of the lung with grossly visible pneumonia was recorded for each pig based on a previously described scoring system (P. G. Halbur et al., 1995, supra). Other lesions such as enlargement of lymph nodes were noted separately. Sections for histopathologic examination were taken from nasal turbinate, lungs (seven sections) (id.), heart, brain, lymph nodes (tracheobronchial, iliac, mesenteric, subinguinal), tonsil, thymus, liver, gall bladder, spleen, joints, small intestine, colon, pancreas, and kidney. The tissues were examined in a blinded fashion and given a subjective score for severity of lung, lymph node, and liver lesions as described in Example 7. Lung scores ranged from 0 (normal) to 3 (severe lymphohistiocytic interstitial pneumonia). Liver scores ranged from 0 (normal) to 3 (severe lymphohistiocytic hepatitis). Lymph node scores were for an estimated amount of lymphoid depletion of follicles ranging from 0 (normal or no lymphoid depletion) to 3 (severe lymphoid depletion and histiocytic replacement of follicles).

To determine the pathogenicity of PCV1, PCV2, chimeric PCV1-2 and reciprocal chimeric PCV2-1 infectious DNA clones in pigs, gross lesions were examined first. The results are shown in Table 9 below. Lymph nodes of animals from the uninoculated control Group 1 were normal at both 21 and 49 DPIs. Pigs in the four inoculated groups had variable degrees of gross lesions limited to the lymph nodes. In PCV1 inoculated Group 2 pigs, lymph nodes were grossly normal at 21 DPI, however, mild to moderate swelling and discoloration of lymph nodes was detected at 49 DPI. All PCV2 inoculated Group 3 pigs had enlarged lymph nodes two to five times the normal size, that were firm and tan colored at both 21 and 49 DPIs. Lymph nodes from chimeric PCV1-2 inoculated animals were mild to moderately swollen and discolored at both 21 and 49 DPIs in 5 out of 7 pigs. In Group 5 pigs, inoculated with the PCV2-1 clone, 1 out of 8 animals had mild swelling and discoloration of the lymph nodes at 21 DPI. The average scores of gross lesions of the lymph nodes in pigs inoculated with chimeric PCV1-2 clone were not statistically different from those in Groups 1, 2, and 5, but were statistically different from those of the pathogenic PCV2 inoculated Group 3 pigs at both 21 and 49 DPIs. Average lymphoid gross lesion scores on 49 DPI from the PCV1, PCV2, and PCV1-2 inoculated animals were not statistically different from each other, but were all statistically different from the average gross lesion scores of Groups 1 and 5.

Next, microscopic lesions were examined. The results are shown in Table 10 below. No microscopic lesions were detected in either uninoculated control Group 1 pigs or PCV1 inoculated Group 2 pigs at any DPI. Microscopic lung lesions characterized as mild peribronchiolar lymphoplasmacytic and histiocytic bronchointerstitial pneumonia, were observed in 1 out 8 of the PCV2 inoculated pigs. In PCV1-2 and PCV2-1 inoculated animals, no microscopic lesions were observed in the lungs. No lesions were observed in the thymuses of any inoculated pigs. Mild multifocal lymphoplasmacytic myocarditis was observed in 2 of 8 pigs in the PCV2 inoculated group. Heart tissues from PCV1-2 and PCV2-1 inoculated animals were free of microscopic lesions. Mild multifocal lymphoplasmacytic interstitial nephritis was observed in 4 out of 8 pigs in PCV2 inoculated group, in 2 out of 7 PCV1-2 inoculated pigs and in 1 out of 8 PCV2-1 inoculated pigs. Mild-to-moderate lymphoid depletion and histiocytic replacement of follicles were observed in the tonsil in 5 out of 8 pigs, in the spleen in 3 out of 8 pigs, and in the lymph nodes in 8 out of 8 pigs in the PCV2-inoculated group. In the chimeric PCV1-2 inoculated animals, mild lymphoid depletion and histiocytic replacement of follicles were observed in the lymph nodes of 2 out of 7 pigs but were not detected in either the spleen or tonsils. No lymphoid depletion and histiocytic replacement of follicles were observed in the lymph nodes, spleen or tonsils of the reciprocal chimeric PCV2-1 inoculated animals. Mild-to-moderate lymphoplasmacytic hepatitis was observed in 7 out of the 8 PCV2-inoculated pigs. Mild lymphoplasmacytic hepatitis was observed in 2 out of the 7 chimeric PCV1-2 inoculated pigs. No lymphoplasmacytic hepatitis was observed in reciprocal chimeric PCV2-1 inoculated pigs. Lesions in other tissues were unremarkable.

Microscopic lesions in the lung, liver, and lymph nodes were scored according to a published scoring system (P. G. Halbur et al., 1995, supra). The results are shown in Table 10 below. Average scores of lesions in lymph nodes in pigs from the chimeric PCV1-2 inoculated Group 4 were similar to those from Groups 1, 2 and 5 but were statistically different from those of the pathogenic PCV2 inoculated Group 3 pigs, at both 21 and 49 DPIs. Average microscopic liver lesion scores from the chimeric PCV1-2 inoculated group at 21 DPI were statistically different from those of PCV2 inoculated Group 3 animals but were similar to those of Groups 1, 2 and 5 pigs at 21 DPI. At 49 DPI, the average microscopic liver scores from Group 4 chimeric PCV1-2 inoculated pigs were not statistically different from those of Groups 1, 2, 3 and 5 pigs. There were no acceptable scoring systems for other tissues or organs.

TABLE 9

Gross Lesions of Lymph Nodes in Control and Inoculated Pigs

| Group | Inoculum[a] | DPI[b] 21 | 49 |
|---|---|---|---|
| 1 | PBS | 0/4(0.0) | 0/4(0.0) |
| 2 | PCV1 DNA | 0/4(0.0) | 4/4(1.5) |
| 3 | PCV2 DNA | 4/4(2.5) | 4/4(2.25) |
| 4 | PCV1-2 DNA | 2/3(0.66) | 3/4(1.25) |
| 5 | PCV2-1 DNA | 1/4(0.25) | 0/4(0.0) |

[a]Phosphate buffered saline (PBS) used as negative control. The inocula were cloned genomic PCV or chimeric PCV DNA in pSK plasmid.
[b]Four pigs from each group were necropsied at 21 DPI and the remaining pigs were necropsied at 49 DPI; number positive/number tested. Number with lesions/number tested (range of estimated severity lymph node enlargement)

EXAMPLE 18

Serology

Blood was collected from all pigs at −2, 7, 14, 21, 28, 35, 42 and 49 DPIs. Serum antibodies to PRRSV were assayed using Herd Check PRRSV ELISA (IDEXX Laboratories, Westbrook, Mass.). Serum antibodies to PPV were detected by a hemagglutination inhibition (HI) assay (H. S. Joo et al., "A standardized haemagglutination inhibition test for porcine parvovirus antibody," Aust. Vet. J. 52:422-424 (1976)). Serum antibodies to PCV2 were detected by a modified indirect ELISA based on the recombinant ORF2 capsid protein of PCV2 as described hereinabove (see also P. Nawagitgul et al., "Modified indirect porcine circovirus (PCV) type 2-based and recombinant capsid protein (ORF2)-based ELISA for the detection of antibodies to PCV," Immunol. Clin. Diagn. Lab Immunol. 1:33-40 (2002)). Serum antibodies to PCV1 were detected by an indirect immunofluorescence assay (IFA). PK-15 cells infected with PCV1 were grown on eight-well LabTek chamber slides. When the infected PK-15 cells reach about 95-100% confluency, the infected cells were fixed with a solution containing 80% acetone and 20% methanol at 4° C. for 20 min. The fixed cells were washed once with PBS buffer. One hundred microliters of 1:10 diluted pig serum sample in PBS was added to the chambers, and incubated for 1 hour at 37° C. The cells were then washed three times with PBS and incubated for 45 min. at 37° C. with FITC-labeled goat anti-swine secondary antibody. The slides were subsequently washed three times with PBS, mounted with fluoromount-G, coverslipped and examined under a fluorescent microscope. For the positive control, PCV1 infected cells were incubated with a diluted PCV1 specific monoclonal antibody (gift of Dr. G. M. Allan), followed by an incubation with FITC-labeled goat anti-mouse IgG (Kirkegaard & Perry Laboratories, Inc., Gaithersburg, Md.). For the negative control, PCV1 infected cells were incubated with 1:10 diluted swine serum free of PCV1 and PCV2 antibody, followed by an incubation with FITC-labeled goat anti-swine IgG (Kirkegaard& Perry Laboratories, Inc., Gaithersburg, Md.).

TABLE 10

Distribution of Histopathological Lesions in Different Tissues/Organs from Control and Inoculated Pigs

| Group | Inoculum[a] | DPI[b] | Lung[c] | Liver[d] | Lymph Nodes[e] | Spleen | Thymus | Ileum | Brain | Heart | Kidney | Tonsil |
|---|---|---|---|---|---|---|---|---|---|---|---|---|
| 1 | PBS | 21 | 0/4(0.0) | 0/4(0.0) | 0/4(0.0) | 0/4 | 0/4 | 0/4 | 0/4 | 0/4 | 0/4 | 0/4 |
|   |   | 49 | 0/4(0.0) | 0/4(0.0) | 0/4(0.0) | 0/4 | 0/4 | 0/4 | 0/4 | 0/4 | 0/4 | 0/4 |
| 2 | PCV1 DNA | 21 | 0/4(0.0) | 0/4(0.0) | 0/4(0.0) | 0/4 | 0/4 | 0/4 | 0/4 | 0/4 | 0/4 | 0/4 |
|   |   | 49 | 0/4(0.0) | 0/4(0.0) | 0/4(0.0) | 0/4 | 0/4 | 0/4 | 0/4 | 0/4 | 0/4 | 0/4 |
| 3 | PCV2 DNA | 21 | 0/4(0.0) | 4/4(1.5) | 4/4(1.75) | 3/4 | 0/4 | 0/4 | 1/4 | 1/4 | 2/4 | 3/4 |
|   |   | 49 | 1/4(0.25) | 3/4(0.75) | 4/4(1.0) | 0/4 | 0/4 | 0/4 | 1/4 | 2/4 | 2/4 |
| 4 | PCV1-2 DNA | 21 | 0/3(0.0) | 1/3(0.33) | 1/3(0.33) | 0/4 | 0/4 | 0/4 | 0/4 | 0/4 | 0/4 | 0/4 |
|   |   | 49 | 0/4(0.0) | 1/4(0.25) | 1/4(0.25) | 0/4 | 0/4 | 0/4 | 0/4 | 0/4 | 2/4 | 0/4 |
| 5 | PCV2-1 DNA | 21 | 0/4(0.0) | 0/4(0.0) | 0/4(0.0) | 0/4 | 0/4 | 0/4 | 0/4 | 0/4 | 0/4 | 0/4 |
|   |   | 49 | 0/4(0.0) | 0/4(0.0) | 1/4(0.25) | 0/4 | 0/4 | 0/4 | 0/4 | 0/4 | 0/4 | 0/4 |

[a]Phosphate buffered saline (PBS) used as negative control. The inocula were cloned genomic PCV or chimeric PCV DNA in pSK plasmid.
[b]Four pigs from each group were necropsied at 21 DPI and the remaining pigs were necropsied at 49 DPI.
[c]Number positive/number tested (average histological lung score: 0, normal; 1, mild interstitial pneumonia; 2, moderate; 3, severe).
[d]Number positive/number tested (Average histological liver sore: 0, normal; 1, mild hepatitis; 2, moderate; 3, severe.)
[e]Number positive/number tested (Average histological lymphoid (lymph nodes) depletion score: 0, normal; 1, mild; 2, moderate; 3, severe.)

EXAMPLE 19

PCR Detection

To detect PCV1, PCV2, chimeric PCV1-2 and reciprocal chimeric PCV2-1 viremia in sera from inoculated pigs, serum samples collected at different DPIs were tested by PCR. Viral DNA was extracted from 100 µl of each serum sample using DNAzol reagent according to the manufacturer's protocol (Molecular Research Center, Cincinnati, Ohio). The extracted DNA was resuspended in DNase, RNase and proteinase-free water. To amplify clone-specific genomic sequences of PCV1, PCV2, chimeric PCV1-2 and chimeric reciprocal PCV2-1, two sets of nested PCR primer pairs were designed (Table 6, above). The first set of nested primers was designed based on published PCV1 sequences. Primers Gen.PCV1 set forth in SEQ ID NO:20 and Orf. PCV1 set forth in SEQ ID NO:19 amplified a 400 bp fragment in the presence of the PCV1 genome. The nested primers, nested.Gen.PCV1 set forth in SEQ ID NO:22 and nested.Orf.PCV1 set forth in SEQ ID NO:21, amplified a 220 bp fragment.

To detect PCV2 viremia, PCV2 primer pair Gen.PCV2 set forth in SEQ ID NO:24 and Orf.PCV2 set forth in SEQ ID NO:23 amplified a 900 bp fragment in the presence of PCV2 in the first round of PCR. Primers nested.Gen.PCV2 set forth in SEQ ID NO:26 and nested.Orf.PCV2 set forth in SEQ ID NO:25 amplified a 600 bp fragment in the nested PCR.

To detect chimeric PCV1-2 viremia, the first round of PCR reaction employed the PCV1-specific primer Gen. PCV1 set forth in SEQ ID NO:20 and the PCV2 ORF2-specific primer Orf.PCV2 set forth in SEQ ID NO:23 to amplify a chimeric fragment of 580 bp. For the nested PCR, PCV1-specific primer nested.Gen.PCV1 set forth in SEQ ID NO:22 and the PCV2 ORF2-specific primer nested.Orf. PCV2 set forth in SEQ ID NO:25 were used to amplify a chimeric fragment of 370 bp.

To detect reciprocal chimeric PCV2-1 viremia, the first round of PCR employed the PCV2-specific primer Gen. PCV2 set forth in SEQ ID NO:24 and the PCV1 ORF2-specific primer Orf.PCV1 set forth in SEQ ID NO:19 to amplify a chimeric fragment of 700 bp. For the nested PCR, the PCV2-specific primer nested.Gen.PCV2 set forth in SEQ ID NO:26 and the PCV1 ORF2-specific primer nested.Orf. PCV1 set forth in SEQ ID NO:21 were used to amplify a 460 bp chimeric fragment. All PCR parameters were essentially the same, consisting of 38 cycles of denaturation at 94° C. for 1 min., annealing at 45° C. for 1 min., and extension at 72° C. for 1.5 min. The serum samples from negative control pigs were tested by a PCR-RFLP diagnostic assay, which can detect and differentiate both PCV1 and PCV2 as described previously (M. Fenaux et al., "Genetic characterization of type 2 porcine circovirus (PCV-2) from pigs with postweaning multisystemic wasting syndrome in different geographic regions of North America and development of a differential PCR-restriction fragment length polymorphism assay to detect and differentiate between infections with PCV-1 and PCV-2," J. Clin. Microbiol. 38: 2494-503 (2000)). PCR products from selected animals in each group were sequenced to verify the origin of the virus infecting pigs.

EXAMPLE 20

Immunohistochemistry (IHC)

IHC detection of PCV2-specific antigen was performed on lymph node tissues collected from all pigs necropsied at 21 and 49 DPIs. A rabbit polyclonal antiserum against PCV2 was used for the IHC, according to the general procedures described previously (S. D. Sorden et al., "Development of a polyclonal-antibody-based immunohistochemical method for the detection of type 2 porcine circovirus in formalin-fixed, paraffin-embedded tissue," J. Vet. Diagn. Invest. 11:528-530 (1999)).

Based on the IHC staining of PCV2-specific antigen, lymphoid tissues from the uninoculated control, PCV1 and PCV2-1 inoculated pigs were negative for PCV2 antigen. PCV2 antigen was detected in lymphoid tissues of 7 out of 8 animals in the PCV2 inoculated group. PCV2 antigen was also detected in lymphoid tissue of 1 out of 7 pigs from the chimeric PCV1-2 inoculated group.

EXAMPLES 21-24

The following general materials and methods are employed in Examples 21-24:

(1) Virus and cell. The PCV1 virus used in this invention was originally isolated from a PK-15 cell line (ATCC CCL-33) (M. Fenaux et al., 2002, supra). The PCV2 virus used herein was originally isolated from a spleen tissue sample of a pig with naturally occurring PMWS (isolate 40895) (M. Fenaux et al., 2002, supra; M. Fenaux et al., 2000, supra,). The PK-15 cell line used herein was free of PCV1 contamination (M. Fenaux et al., 2002, supra).

(2) Serial passages of PCV2 in vitro. A homogenous PCV2 virus stock, designated passage 1 (VP1), was generated by transfection of PK-15 cells with the PCV2 infectious DNA clone as previously described (M. Fenaux et al., 2002, supra). The VP1 PCV2 virus stock was then serially passaged for 120 times in PK-15 cells. The infected cells, when reaching confluency, were subcultured at an approximate 1 to 3 ratio in minimum essential medium (MEM) with Earle's salts and L-glutamine supplemented with 2% fetal calf serum (FCS) and 1× antibiotic (Invitrogen, Inc., CA). For every 10 to 15 passages, the infected cells were harvested by frozen and thawed three times, and used to inoculate a new PK-15 culture. The newly infected culture was then passed 10 to 15 times by subculturing before repeating the freeze-thaw procedure. This procedure was repeated until it reached passage 120 (VP120). The virus harvested at each passage was stored at −80 for further analyses.

(3) Biological characterization of PCV1, PCV2 VP1, and PCV2 VP120 viruses in PK-15 cells. A one-step growth curve was performed to determine the comparative growth ability of PCV1, PCV2 VP1, and PCV2 VP120 in vitro. PK-15 cells were grown on six 12-well plates. The plates were infected, in duplicate, with PCV1, PCV2 VP1 or PCV2 VP120 at a multiplicity of infection (M.O.I.) of 0.1, respectively. After 1 hour absorption, the inoculum was removed and the cell monolayer was washed five times with phosphate buffered saline (PBS). Maintenance MEM media (2% bovine calf serum and 1× antibiotics) was subsequently added to each well, and the infected cell cultures were continuously incubated at 37° C. with 5% $CO_2$. Every 12 hours, the media and infected cells from duplicate wells of each inoculated group were harvested and stored at −80° C. until virus titration. The infectious titers of PCV1 and PCV2 viruses collected at different time points were determined by immunofluorescent assays (IFA) specific for PCV1 or PCV2 as previously described (M. Fenaux et al., 2002, supra; M. Fenaux et al., 2003, supra).

(4) Genetic characterization of PCV2 viruses at different passages. PCV2 viruses harvested from passages 1, 30, 60, 90, and 120 were genetically characterized by determining the complete genomic sequences of the viruses from each passage. Viral DNA was extracted from 100 µl of the cell culture materials collected at passages 1, 30, 60, 90, and 120 by using DNAzol reagent according to the manufacturer's protocol (Molecular Research Center, Cincinnati, Ohio). The extracted DNA was resuspended in DNase-, RNase- and proteinase-free water. To amplify the entire genome, three pairs of PCV2 specific primers were used to amplify three overlapping fragments: primer pair PCV2.2B (5'-TCCGAAGACGAGCGCA-3', set forth in SEQ ID NO:27) and PCV2.2A (5'-GAAGTAATCCTC-CGATAGAGAGC-3', set forth in SEQ ID NO:28), primer pair PCV2.3B (5'-GTTACAAAGTTATCATCTA-GAATAACAGC-3', set forth in SEQ ID NO:29) and PCV2.3A (5'-ATTAGCGAACCCCTGGAG-3', set forth in SEQ ID NO:30), and primer pair PCV2.4B (5'-AGAGACTAAAGGTGGAACTGTACC-3', set forth in SEQ ID NO:31) and PCV2.4A (5'-AGGGGGGACCAA-CAAAAT-3', set forth in SEQ ID NO:32). The PCR reaction consisted of 38 cycles of denaturation at 94° C. for 1 min, annealing at 46° C. for 30 sec, and extension at 72° C. for 2 min, followed by a final extension at 72° C. for 7 min. The PCR products of expected size were excised from 0.8% agarose gels followed by purification with a Geneclean Kit (Bio 101, Inc., La Jolla, Calif.). The PCR products were directly sequenced for both strands using the PCR primers. The nucleotide and amino acid sequences were compiled and analyzed with the publicly accessible MacVector program (Oxford Molecular Ltd., Beaverton, Oreg.) using Clustal alignment. The complete sequence of PCV2 VP120 was compared to PCV2 VP1 and 91 other PCV2 isolates as well as 4 PCV1 isolates available in the GenBank database.

(5) Experimental characterization of the serially-passaged PCV2 VP120, and VP1. To determine the pathogenic potential of the VP120 PCV2, thirty-one SPF pigs of 3 to 4 weeks of age were randomly assigned to 3 groups, and housed separately. Prior to the inoculation, serum samples from all piglets were tested by PCR for the presence of PCV1 or PCV2 DNA. To maximize the efficiency of inoculation, each pig was inoculated with 1 ml of the inoculum intramuscularly and 3 ml intranasally. The ten pigs in Group 1 were each inoculated with PBS buffer as negative controls. Eleven pigs in Group 2 each received $10^{4.9}$ TCID$_{50}$ of PCV2 VP120, and ten pigs in Group 3 each received $10^{4.9}$ TCID$_{50}$ of PCV2 VP1. All pigs were monitored for clinical signs of disease. Serum samples were collected from each pig at −1, 7, 14, 21, 28, 35 and 42 days post inoculation (DPI). At 21 DPI, 5 randomly selected pigs from each group were necropsied. The remaining pigs in each group were necropsied at 42 DPI.

(6) Clinical evaluation. Pigs were weighed at −1, 7, 14, 21, 28, 35 and 42 DPI. Rectal temperatures and clinical scores, ranging from 0 to 6 (0=normal; 6=severe) (M. Fenaux et al., 2002, supra), were recorded every other day from 0 to 42 DPI. Clinical observations, including evidence of central nervous system disease, liver disease (icterus), musculoskeletal disease, and changes in body condition, were recorded at two-day intervals. All clinical evaluations were performed by a team of two people to confirm observations.

(7) Gross pathology and histopathology. Complete necropsies were performed on all pigs. The necropsy team was blinded to the infection status of the pigs. The percentage of lung with grossly visible pneumonia was estimated for each pig based on a previously described scoring system (M. Fenaux et al., 2002, supra). Lesions such as the enlargement of the lymph nodes (ranging from 0 for normal to 3 for three times normal size) were scored separately. Sections for histopathologic examination were taken from the nasal turbinate, lungs (five sections, see M. Fenaux et al., 2002, supra), heart, brain, lymph nodes (tracheobronchial, iliac, mesenteric, subiliac, and superficial inguinal), tonsil, liver, thymus, spleen, pancreas, and kidney. The tissues were examined in a blinded fashion and given a subjective score for severity of lung, lymph node, and liver lesions (M. Fenaux et al., 2002, supra). Lung scores ranged from 0 (normal) to 3 (severe lymphohistiocytic interstitial pneumonia). Liver scores ranged from 0 (normal) to 3 (severe lymphohistiocytic interstitial hepatitis). Lymph node scores were an estimated amount of lymphoid depletion of follicles ranging from 0 (normal or no lymphoid depletion) to 3 (severe lymphoid depletion and histiocytic replacement of follicles) (M. Fenaux et al., 2002, supra).

(8) Serology. Blood samples were collected from all pigs at −1, 7, 14, 21, 28, 35, and 42 DPI. Serum antibodies to PCV2 were detected by a modified indirect ELISA based on the recombinant ORF2 capsid protein of PCV2 (P. Nawagitgul et al., 2002, supra). Serum samples with a sample/positive (S/P) ratio above 0.2 were considered seropositive for PCV2.

(9) Quantitative real-time PCR. Quantitative real-time PCR was performed to determine PCV2 virus loads in serum samples collected at −1, 7, 14, 21, 28, 35, and 42 DPI and in lymphoid tissue samples collected at 21 DPI and 42 DPI. Primer pair MCV1 (5'-GCTGAACTTTTGAAAGT-GAGCGGG-3', set forth in SEQ ID NO:17) and MCV2 (5'-TCACACAGTCTCAGTAGATCATCCCA-3', set forth in SEQ ID NO:18) (M. Fenaux et al., 2000, supra) was used for the quantitative real-time PCR. The PCR reaction was performed in the presence of intercalating SYBR green dye (Molecular Probes, Inc. Eugene, Oreg.) as described herein. A standard dilution series with a known amount of pBluescript plasmid containing a single copy of the PCV2 genome (M. Fenaux et al., 2002, supra) was run simultaneously in each real-time PCR reaction to quantify the virus genomic copy numbers.

(10) Immunohistochemistry (IHC). IHC detection of PCV2 specific antigen was performed on lymph node, spleen, tonsil and thymus tissues collected during necropsy at 21 and 42 DPI as described hereinabove (M. Fenaux et al., 2002, supra). The amount of PCV2 antigen distributed in the lymphoid tissues was scored in a blinded fashion by assigning a score of 0, if no signal, to 3 for a strong positive signal (S. D. Sorden et al., "Development of a polyclonal-antibody-based immunohistochemical method for the detection of type 2 porcine circovirus in formalin-fixed, paraffin-embedded tissue," J. Vet. Diagn. Invest. 11:528-530 (1999)).

(11) Statistical analysis. All statistical analyses were performed using the SAS®-system (Version 8.02, SAS institute Inc. Cary N.C. 27513). Growth characteristics of viruses were compared by regressive analyses using the GLM procedure. Serum samples S/P ratios were compared by analysis of variance, with the MIXED procedure. The model included effects of inoculum, DPI, and their interaction. S/P ratios were dichotomized to presence/absence of seroconversion at S/P=0.20 and analyzed by logistic regression using the method of generalized equations in the SENROD procedure. Mean viral genomic copy numbers in serum and lymph nodes of piglets in Groups 2 and 3 were compared by the Kruskal-Wallis test using the NPAR1WAY procedure and/or by analysis of variance of ranked data, followed by a Bonferroni test of multiple mean ranks, using the GLM procedure. Serology and viremia data were analyzed for all pigs up to 21 DPI, and separately for those pigs necropsied at 42 DPI. Clinical sign scores were dichotomized to presence/absence of clinical signs for each examination date, and per pig over the entire period of study and compared between groups by Fisher's Exact test using the FREQ procedure, and by logistic regression using LOGISTIC procedure. Gross pathologic and histopathologic scores were compared by the Kruskal-Wallis test using the NPAR1WAY procedure and/or by analysis of variance using the GLM procedure, followed by a Bonferroni test of multiple means. Proportion of pigs with gross and histopathologic lesions in various tissues were compared between groups by Fisher's Exact Test using the FREQ procedure.

EXAMPLE 21

Comparison of the Replication of PCV2 VP120 and PCV2 VP1 in PK-15 Cells

Figure 12:
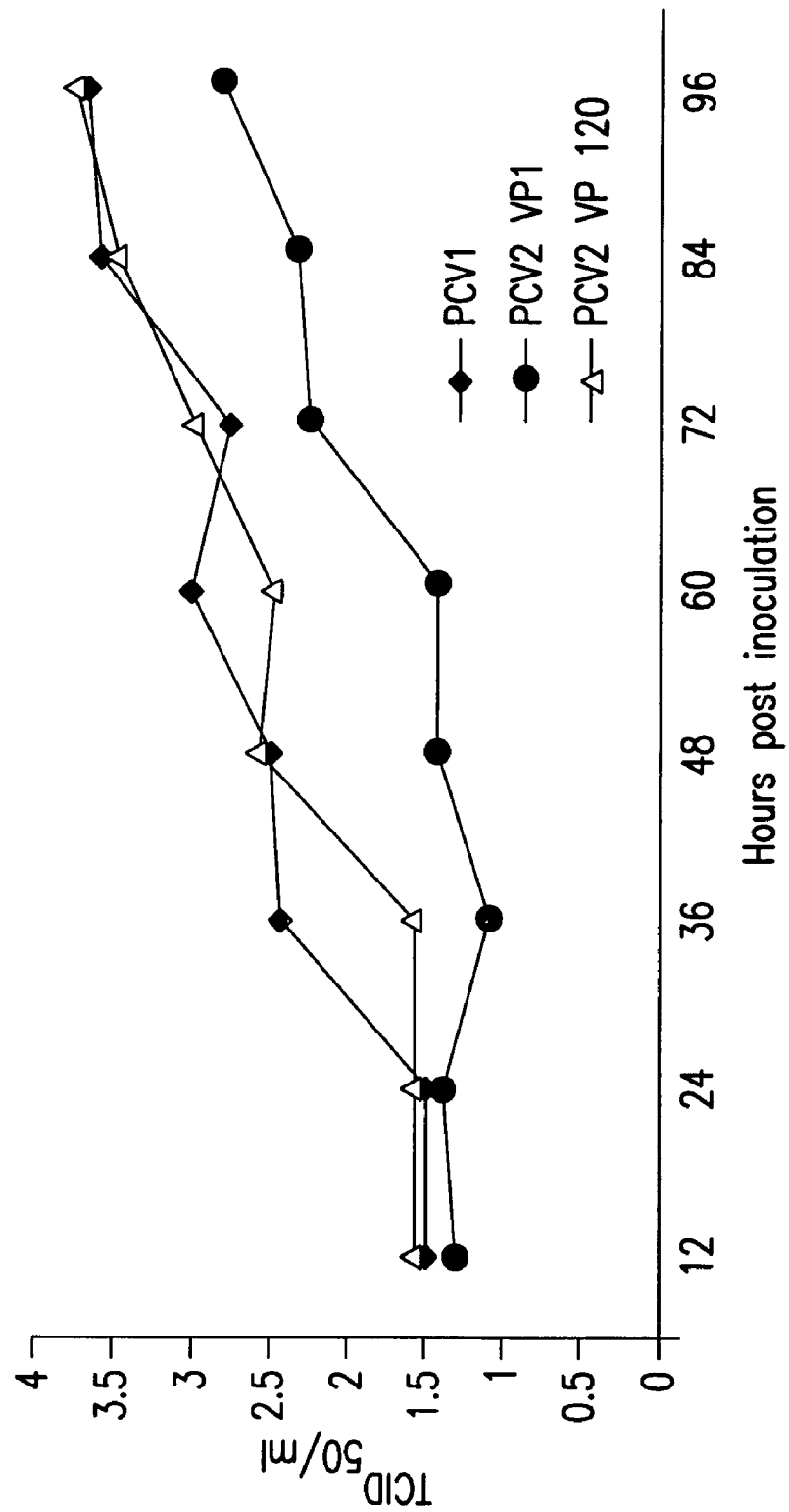
FIG. 12 shows one-step growth curves of PCV1, PCV2 VP1 and PCV2 VP120. Duplicate synchronized PK-15 cell cultures are each infected with PCV1, PCV2 VP1 or PCV2 VP120, all at an M.O.I. of 0.1. All three viruses have a titer of about $10^{1.5}$ TCID$_{50}$/ml at 12 hours postinoculation. PCV1 and PCV2 VP120 replicate more efficiently in vitro than PCV2 VP1 does (p=0.0053).
Figure 13:
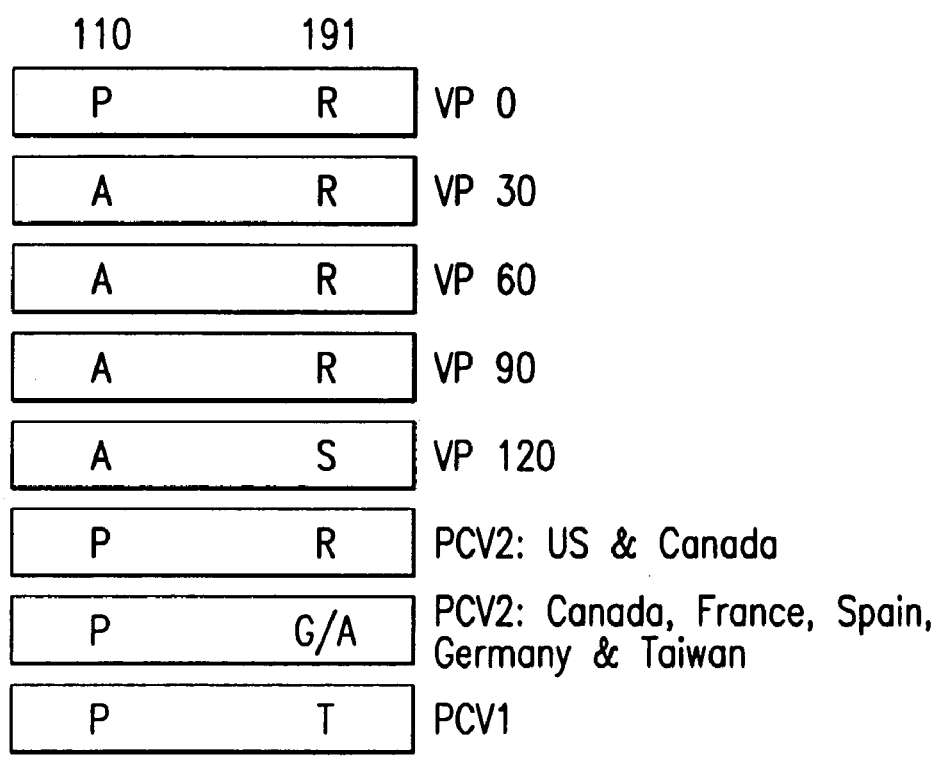
FIG. 13 is a schematic diagram of amino acid mutations in the capsid protein during serial passages of PCV2 in PK-15 cells. Serial passage numbers are indicated as VP1, VP30, VP60, VP90 and VP120. Known field isolates of PCV2 and PCV1 from different geographic origins are also compared for these two mutations.
Figure 14:
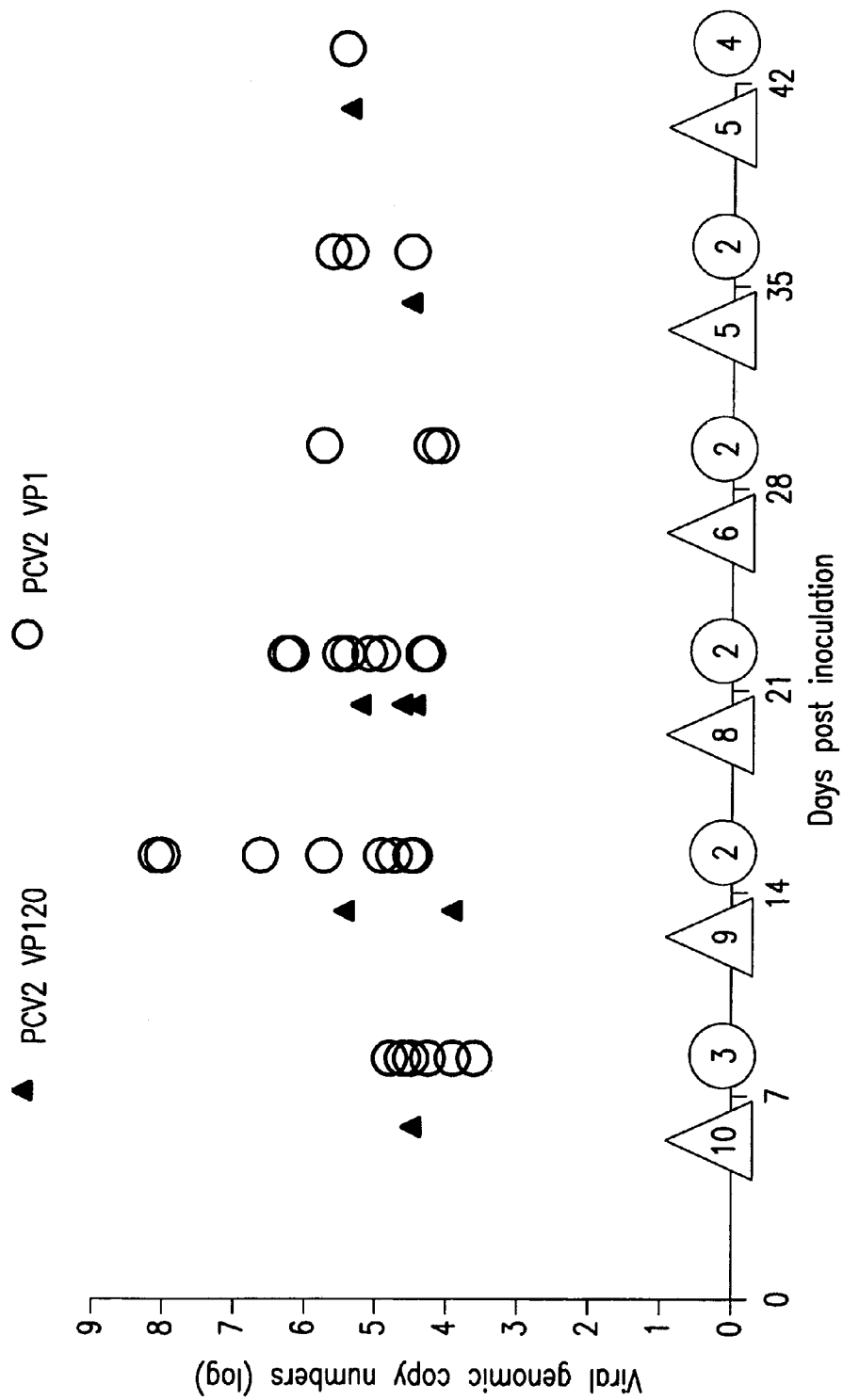
FIG. 14 shows the quantitative real-time PCR results of PCV2 VP1 and PCV2 VP120 viral genomic copy loads in 1 ml of serum sample collected at −1, 7, 14, 21, 28, 35 and 42 days post inoculation (DPI) from Groups 1, 2 and 3 pigs. Group 2 pigs inoculated with PCV2 VP120 that are positive for PCV2 DNA are indicated with a σ. The numbers (10, 9, 8, 6, 5, 5) inside the symbol Δ on the X-axis indicate the number of pigs in Group 2 that are negative for PCV2 viremia on the respective DPI. Group 3 pigs inoculated with PCV2 VP1 that are positive for PCV2 DNA are indicated with symbol O. The numbers (3, 2, 2, 2, 2, 4) inside the symbol O on the X-axis indicate the number of pigs in Group 3 that are negative for PCV2 viremia on the respective DPI. The PCV2 genomic copy loads are represented as a log of copy numbers per 1 ml of serum (Y-axis).

To determine the growth characteristics of PCV1, PCV2 VP1 and VP120, one-step growth curves were performed in duplicate simultaneously for PCV1, PCV2 VP1 and PCV2 VP120. The infectious titers of viruses collected at 12 hour intervals were determined by IFA (FIG. 12). The initial titers after infection at 12 h postinoculation were about $10^{1.5}$ $TCID_{50}$/ml for all three viruses. The infectious titers of PCV1 and PCV2 VP120 compared to PCV2 VP1 increased differently (p=0.0053) from 12 to 96 h. By 96 h postinfection, PCV1 and PCV2 VP120 had titers of $10^{3.66}$ and $10^{3.75}$ $TCID_{50}$/ml, whereas the PCV2 VP1 was $10^{2.83}$ $TCID_{50}$/ml (FIG. 12). It was demonstrated that PCV2 VP120 surprisingly replicated more efficiently in PK-15 cells than PCV2 VP1.

EXAMPLE 22

Identification of Two Amino Acid Mutations within the PCV2 Capsid Protein During Serial Passages The complete genomes of PCV2 passage numbers 1, 30, 60, 90, and 120 were amplified and sequenced. Sequence analyses revealed that there were a total of 2 nucleotide and 2 amino acid mutations in the entire genome after 120 passages. The first mutation appeared in passage 30 (VP30) in which a proline was substituted for an alanine at position 110 of the capsid (P110A) (FIG. 13). This mutation was also present during the remaining passages. A second mutation from arginine to serine at position 191 of the capsid (R191S) was identified at passage 120 but not in lower passages (FIG. 13). The amino acid mutations were the result of the corresponding mutations that occurred in the genome in nucleotide positions 328 (C to G) and 573 (A to C). In position 328 of the nucleotide sequence, cytosine changes to guanine (C to G) leading to the amino acid change of P110A. In position 573, adenine changes to cytosine (A to C) leading to the second amino acid change of R191S.

By comparing all known PCV1 and PCV2 sequences in the Genbank including 91 PCV2 and 4 PCV1 isolates, it was found that that the P110A mutation is unique (FIG. 13) as all known PCV1 and PCV2 isolates have a proline at residue 110 of the capsid protein. The serine in the R191S mutation is also unique. However, the amino acid in the 191 position is often variable: PCV2 isolates of North American origin have an arginine, PCV2 isolates of Canadian and French origins have glycine, and PCV2 isolates of Spanish, Taiwanese and German origins have an alanine. All nonpathogenic PCV1 isolates have a threonine residue (FIG. 13).

EXAMPLE 23

Comparison of the Viremia Length and Virus Loads of PCV2 VP120 Virus and PCV2 VP1 Virus in Sera of Infected Pigs Serum samples were collected from all control and inoculated pigs at −1, 7, 14, 21, 28, 35, and 42 DPI and assayed for PCV2 viremia by quantitative real-time PCR and for anti-PCV2 antibody by ELISA. Prior to inoculation at −1 DPI, serum samples from all pigs were tested negative for PCV2 DNA.

The Group 1 negative control pigs were negative for PCV2 viremia throughout the study (see Table 11, below). All pigs in Group 1 had detectable PCV2 maternal antibodies at −1 DPI, which all waned by 21 DPI. Seroconversion to PCV2 was not detected in any of the ten negative control pigs (see Table 12, below).

In the PCV2 VP120 inoculated Group 2 pigs, viremia was first detected in one of eleven pigs at 7 DPI (Table 11, FIG. 14). A total of 4 pigs in Group 2 were viremic during the study. The average length of continuous viremia was 1.6 weeks. By 35 DPI, all Group 2 pigs seroconverted to PCV2 (Table 12).

In the PCV2 VP1 inoculated Group 3 pigs, viremia was first detected in seven of ten pigs at 7 DPI (Table 11, FIG. 14). Nine out of the ten pigs in Group 3 became viremic for PCV2 during the study and the average length of continuous viremia was 3 weeks. All animals in Group 3 seroconverted to PCV2 by 35 DPI (Table 12).

The range of PCV2 genomic copy numbers per ml of serum in positive samples was 8,840 to 274,800 in PCV2 VP120 inoculated Group 2 pigs, and 26,520 to 120,000,000 in PCV2 VP1 inoculated Group 3 pigs (FIG. 14). PCV2 genomic copy loads per ml of serum were greater in Group 3 than that in Group 2 pigs up to 21 DPI (p=0.0003) and 42 DPI (p=0.039). However, PCV2 DNA was recovered from lymph nodes of only 3/11 Group 2 and 2/10 Group 3 pigs, and the median PCV2 genomic copy loads per mg of tracheobronchial lymph node (TBLN) did not differ between Groups 2 and 3 (p=0.72). The virus recovered from the sera and TBLN of 4 selected pigs in Groups 2 and 3 were sequenced, and sequence analyses revealed that the recovered viruses originated from the inocula.

The S/P ratios of PCV2 antibodies differed between Groups 1, 2 and 3 (p<0.0001) and over time (p<0.0001). It was shown that the PCV2 VP120 virus significantly reduced viremia length and virus loads in sera of infected pigs compared to the PCV2 VP1 virus.

TABLE 11

Detection of Viremia by Real-Time PCR in Sera of Inoculated and Control Pigs

| | | No. of pigs positive/no. tested[a] Days post inoculation | | | | | | |
|---|---|---|---|---|---|---|---|---|
| Grp. | Inocula | -1 | 7 | 14 | 21 | 28 | 35 | 42 | total |
| 1 | Control | 0/10 | 0/10 | 0/10 | 0/10 | 0/5 | 0/5 | 0/5 | 0/10 |
| 2 | PCV2 VP 120 | 0/11 | 1/11 | 2/11 | 3/11 | 0/6 | 1/6 | 1/6 | 4/11 |
| 3 | PCV2 VP 1 | 0/10 | 7/10 | 8/10 | 8/10 | 3/5 | 3/5 | 1/5 | 9/10 |

[a]Five pigs per group were necropsied at 21 day post inoculation (DPI) and the remaining pigs were necropsied at 42 DPI.

TABLE 12

Seroconversion to PCV2 Antibodies in Pigs Inoculated with PCV2 Passages 1 (VP1) and 120 (VP120)

| | | No. of pigs positive/no. tested[a] Days post inoculation | | | | | | |
|---|---|---|---|---|---|---|---|---|
| Grp. | Inoculum | -1 | 7 | 14 | 21 | 28 | 35 | 42 |
| 1 | Control | 10/10[b] | 1/10 | 1/10 | 0/10 | 0/5 | 0/5 | 0/5 |
| 2 | PCV2 VP 120 | 3/11[b] | 0/11 | 0/11 | 0/11 | 0/6 | 6/6 | 6/6 |
| 3 | PCV2 VP 1 | 1/10[b] | 0/10 | 1/10 | 2/10 | 4/5 | 5/5 | 5/5 |

[a]Five pigs per group were necropsied at 21 day post inoculation (DPI) and the remaining pigs were necropsied at 42 DPI.
[b]Maternal antibodies were detectable at -1 DPI but waned in all groups between 7 and 21 DPI.

EXAMPLE 24

Attenuation of PCV2 VP120 Virus in Pigs

Mild clinical signs (sneezing and rough coat) were noted in some animals from all three groups. Two of 10 non-inoculated, and all of 21 inoculated pigs developed clinical signs (p=0.051). Up to 21 DPI, Groups 2 and 3 pigs were 58 (95% C.I.: [13.1; 255.0]) and 41 [9.3;178.0] times more likely to show mild clinical signs at any examination date than negative control pigs, with no difference between pigs of Groups 2 and 3 ($OR_{3vs2}$: 1.4[0.8;2.6]). For the 16 pigs that were necropsied at 42 DPI, when evaluated over the entire study period, Groups 2 and 3 pigs again were more likely to show mild clinical signs than negative control pigs ($OR_{2vs1}$: 20.4[4.6;90.1]; $OR_{3vs1}$: 71.6 [16.0;320.8]) with Group 3 pigs being 3.5 [1.9;6.6] times more likely to show mild clinical signs than Group 2 pigs. There were no differences in weight gain (p=0.081) or mean rectal temperatures (p>0.05) among any of the groups.

At necropsies, lymph nodes of 2/5 pigs in Group 1 were mildly enlarged, however this was not associated with PCV2 infection as evidenced by the lack of PCV2 DNA or seroconversion. At 42 DPI necropsy, all Group 1 pigs had normal lymph nodes (see Table 13, below). Group 2 pigs inoculated with PCV2 VP120 had mild to moderately enlarged lymph nodes at both 21 and 42 DPI (Table 13). The lymph nodes in Group 3 pigs were moderately to severely enlarged at both 21 and 42 DPI (Table 13). Pigs inoculated with PCV2 VP1 had visible gross pneumonia at 21 DPI. Visible gross pneumonia was not found in Group 1 or 2 pigs at either 21 or 42 DPI.

Microscopic lung lesions characterized by mild peribronchiolar lymphoplasmacytic and histiocytic bronchointerstitial pneumonia and liver lesions characterized by mild lymphoplasmacytic hepatitis were detected in pigs of all groups (see Table 14, below). Mild lymphoid depletion (LD) of lymph node follicles was detected in 0/5 Group 1 pigs at 21 and 42 DPI, in 3/5 (21 DPI) and in 2/6 (42 DPI) Group 2 pigs, in 4/5 (21 DPI) and 5/5 (42 DPI) Group 3 pigs (Table 14). Mild histiocytic replacement (HR) of lymph node follicles was not observed in Group 1 pigs. In Group 2, mild HR was observed in the lymph nodes of 0/5 pigs at 21 DPI and 2/6 pigs at 42 DPI. In Group 3, mild to moderate HR of the lymph nodes was observed in 3/5 pigs at both 21 and 42 DPI. The tonsil and spleen tissue follicles of the Group 1 pigs were free of LD and HR at 21 or 42 DPI. Mild LD of the tonsil follicles was found in 2/5 pigs in Group 2 at 21 DPI. Mild to moderate LD of the tonsil follicles was found in 2/5 pigs in Group 3 at 21 DPI and mild HR of the tonsil tissue in 1/5 pigs in Group 3 at both 21 and 42 DPI. Mild LD of the spleen follicles was observed in 2/5 and 1/6 pigs in Group 2 at 21 and 42 DPI, respectively. Mild to moderate LD of the spleen follicles was noted in 4/5 in Group 3 pigs at both 21 and 42 DPI. In Group 2 pigs, mild HR of the spleen tissue follicles was found in 1/6 pigs at 42 DPI. In Group 3, 4/5 pigs at 21 DPI and 3/5 pigs at 42 DPI had mild to moderate HR of the spleen tissue follicles (Table 14). Presence of lesions in other tissues and organs are summarized in Table 14.

At necropsies (21 and 42 DPI), PCV2 antigen was not detected by IHC in the lymphoid tissues of the negative control Group 1 pigs. In the PCV2 VP120 inoculated Group 2, low amounts of PCV2 antigen was detected in spleen tissues of 1/5 pigs at 21 DPI, in lymph node tissues of 2/6 pigs at 42 DPI, and in tonsil tissues of 3/6 pigs at 42 DPI (see Table 15, below). In the PCV2 VP0 inoculated Group 3, low-to-high amounts of PCV2 antigen were detected in lymph node tissues of 5/5 pigs, in tonsil tissues of 4/5 pigs, and in spleen tissues of 4/5 pigs at 21 DPI. At 42 DPI, low-to-moderate amounts of PCV2 antigen were detected in PCV2 VP0 inoculated Group 3 (Table 15).

All gross pathologic and histopathologic scores at 21 DPI and 42 DPI were compared by analysis of variance using the GLM procedure followed by a Bonferroni test of multiple means. At 21 DPI, Groups 1 and 2 mean scores are similar (p=1.00) but differ from the mean scores of Group 3 (p=0.0032). By 42 DPI, the mean scores of Group 1 differ from Group 2 (p=0.0083) and Group 3 (p=0.0001), and the Group 2 mean scores are milder than those of Group 3 (p=0.0274) (Tables 13-15).

TABLE 13

Gross Lymph Node and Lung Lesions in Control and Inoculated Pigs

| Group | Inoculum | No. of pigs with enlarged lymph nodes[a] 21 DPI | 42 DPI | No. of pigs with gross pneumonia lesions 21 DPI | 42 DPI |
|---|---|---|---|---|---|
| 1 | Control | 2/5(04[b])[Ic] | 0/5(0.0)[I] | 0/5(0.0)[I] | 0/5(0.0) |
| 2 | PCV2 VP120 | 2/5(0.4)[I] | 4/6(1.3)[II] | 0/6(0.0)[I] | 0/5(0.0) |
| 3 | PCV2 VP1 | 5/5(2.2)[II] | 5/5(2.6)[II] | 2/5(2.6)[II] | 0/5(0.0) |

[a]Five pigs from each group was necropsied at 21 days post inoculation (DPI) and the remaining pigs were necropsied at 42 DPI.
[b]Values in parentheses are the mean scores of estimated lymph node enlargement (0 = normal to 3 severely enlarged and discolored) and mean percentage of lungs affected by gross visible pneumonia (0–100%)
[c]Different superscripts (I, II) indicate different mean value score between groups (p < 0.05).

TABLE 14

Distribution of Histopathological Lesions in Different Tissues and Organs from Control and Inoculated Pigs

| | | | | No. of pigs positive/no. of pigs tested | | | | | | | | |
|---|---|---|---|---|---|---|---|---|---|---|---|---|
| | | | | Lymph nodes | | Tonsil | | Spleen | | | | |
| Group | Inocula | DPI[a] | Lung | LD[¶c] | HR | LD[†] | HR | LD[¶] | HR[†] | Liver | Kidney | Heart |
| 1 | Control | 21 | 0/5(0.0)[b] | 0/5(0.0) | 0/5(0.0) | 0/5(0.0) | 0/5(0.0) | 0/5(0.0) | 0/5(0.0) | 0/5(0.0) | 1/5 | 1/5 |
|   |         | 42 | 3/5(0.6)    | 0/5(0.0) | 0/5(0.0) | 0/5(0.0) | 0/5(0.0) | 0/5(0.0) | 0/5(0.0) | 1/5(0.2) | 1/5 | 0/5 |
| 2 | PCV2    | 21 | 2/5(0.4)    | 3/5(0.6) | 0/5(0.0) | 2/5(0.4) | 0/5(0.0) | 2/5(0.4) | 0/5(0.0) | 3/5(0.6) | 2/5 | 0/5 |
|   | VP120   | 42 | 5/6(1.0)    | 2/6(0.3) | 2/6(0.3) | 0/6(0.0) | 0/6(0.0) | 1/6(0.2) | 1/6(0.2) | 0/6(0.0) | 2/6 | 0.5 |
| 3 | PCV2    | 21 | 2/5(0.4)    | 4/5(1.2) | 3/5(1.0) | 5/5(1.2) | 1/5(0.2) | 4/5(1.0) | 4/5(1.0) | 3/5(1.2) | 3/5 | 3/5 |
|   | VP0     | 42 | 5/5(1.4)    | 5/5(1.4) | 3/5(0.8) | 0/5(0.0) | 1/5(0.2) | 4/5(1.0) | 3/5(0.6) | 3/6(0.6) | 1/5 | 2/5 |

[a]DPI, Days postinoculation
[b]Values in parentheses are mean histological scores for interstitial pneumonia and for interstitial hepatitis and lymphoid depletion (LD) and histiocytic replacement (HR) for lymph nodes, tonsils and spleen.
[c]Indicates difference (p < 0.05) using Fisher's Exact test between Groups 1, 2, and 3 in severity of respective histopathological lesion with symbol † at 21 DPI and symbol ¶ at 42 DPI necropsies.

TABLE 15

Immunohistiochemical Detection of PCV2 Antigen in Lymph Nodes, Tonsils and Spleen of Inoculated and Control Pigs

| | | | No. of pigs positive/no. tested[b] | | |
|---|---|---|---|---|---|
| Group | Inocula | DPI[a] | Lymph node[†b] | Tonsil[†] | Spleen |
| 1 | Control | 21 | 0/5(0.0)[c] | 0/5(0.0) | 0/5(0.0) |
|   |         | 42 | 0/5(0.0)    | 0/5(0.0) | 0/5(0.0) |
| 2 | PCV2 VP120 | 21 | 0/5(0.0) | 0/5(0.0) | 1/5(0.2) |
|   |            | 42 | 2/6(0.3) | 3/6(0.5) | 0/6(0.0) |
| 3 | PCV2 VP1 | 21 | 5/5(1.6) | 4/5(1.0) | 4/5(1.2) |
|   |          | 42 | 3/5(0.8) | 2/5(0.4) | 2/5(0.4) |

[a]DPI, days postinoculation
[b]Indicates difference(p < 0.05) using Fisher's Exact test between Groups 1, 2, and 3 of PCV2 antigen presence in respective tissues with symbol † at 21 DPI.
[c]Value in parentheses are the mean scores of the amounts of PCV2 antigen in lymphoid tissues (ranging from 0, no antigen detected, to 3, high levels of antigen).

In the foregoing, there has been provided a detailed description of particular embodiments of the present invention for the purpose of illustration and not limitation. It is to be understood that all other modifications, ramifications and equivalents obvious to those having skill in the art based on this disclosure are intended to be included within the scope of the invention as claimed.

What is claimed is:

1. An infectious chimeric nucleic acid molecule of porcine circovirus (PCV1-2) comprising a nucleic acid molecule encoding an infectious, nonpathogenic PCV1 which contains an immunogenic open reading frame (ORF) gene of a pathogenic PCV2 in place of an ORF gene of the PCV1 nucleic acid molecule.

2. The chimeric nucleic acid molecule according to claim 1, wherein the immunogenic PCV2 ORF gene replaces the same ORF gene position in the PCV1 nucleic acid molecule.

3. The chimeric nucleic acid molecule according to claim 2, wherein the immunogenic ORF gene is the ORF2 capsid gene.

4. The chimeric nucleic acid molecule according to claim 3, wherein the chimeric nucleic acid molecule comprises the nucleotide sequence set forth in SEQ ID NO:2 or its complementary strand.

5. The chimeric nucleic acid molecule according to claim 4, wherein the chimeric nucleic acid molecule contains a mutation in the ORF2 gene comprising a guanine in nucleotide position 328 (C to G), a cytosine in nucleotide position 573 (A to C) or both C to G and A to C mutations in positions 328 and 573, respectively.

6. A biologically functional plasmid or viral vector containing the chimeric nucleic acid molecule according to claim 4.

7. The plasmid according to claim 6 having ATCC Patent Deposit Designation PTA-3912.

8. A suitable host cell transfected by a vector comprising the chimeric nucleic acid molecule according to claim 4.

9. An avirulent, infectious chimeric porcine circovirus produced by cells containing the chimeric nucleic acid molecule according to claim 4.

10. The infectious chimeric porcine circovirus according to claim 9, wherein the cells containing the chimeric nucleic acid molecule are contained in a plasmid having ATCC Patent Deposit Designation PTA-3912.

11. A viral vaccine comprising a nontoxic, physiologically acceptable carrier and an immunogenic amount of a member selected from the group consisting of:
  (a) a chimeric nucleic acid molecule having the nucleotide sequence set forth in SEQ ID NO:2 or its complementary strand;
  (b) a biologically functional plasmid or viral vector containing a chimeric nucleic acid molecule having the nucleotide sequence set forth in SEQ ID NO:2 or its complementary strand; and
  (c) an avirulent, infectious chimeric porcine circovirus made from a chimeric nucleic acid molecule of PCV1-2, wherein the ORF2 capsid gene of PCV1 is replaced with the ORF2 capsid gene of PCV2.

12. The viral vaccine according to claim 11, wherein the chimeric nucleic acid molecule contains a mutation in the ORF2 gene comprising C to G in nucleotide position 328, A to C in nucleotide position 573 or both C to G and A to C mutations in positions 328 and 573, respectively.

13. The viral vaccine according to claim 11, wherein the vaccine contains live chimeric porcine circovirus.

14. A method of immunizing a pig against viral infection or postweaning multisystemic wasting syndrome (PMWS) caused by PCV2 comprising administering to the pig an immunologically effective amount of the vaccine according to claim 11.

15. The method according to claim 14, which comprises administering the chimeric nucleic acid molecule or live chimeric porcine circovirus to the pig.

16. The method according to claim 15, which comprises administering the vaccine parenterally, intranasally, intradermally or transdermally to the pig.

17. The method according to claim 16, which comprises administering the vaccine intralymphoidly or intramuscularly to the pig.

18. A method of preparing the infectious chimeric nucleic acid molecule of PCV1-2 according to claim 1, which comprises removing an open reading frame (ORF) gene of a nucleic acid molecule encoding an infectious, nonpathogenic PCV1; replacing the ORF gene position of the PCV1 with an immunogenic ORF gene from a pathogenic PCV2; and recovering the chimeric nucleic acid molecule.

19. The method according to claim 18, wherein the immunogenic PCV2 ORF gene replaces the same ORF gene position of the PCV1 nucleic acid molecule.

20. The method according to claim 19, wherein the immunogenic ORF gene is ORF2.

21. The method according to claim 20, wherein the ORF2 gene of PCV2 is obtained from the molecular nucleic acid molecule of PCV2 contained in an expression vector having ATCC Patent Deposit Designation PTA-3913.

22. The method according to claim 20, wherein the ORF2 gene of PCV2 is excised from a PCV2 after at least 30 serial passages of the PCV2 in PK-15 cells.

23. The method according to claim 22, wherein the ORF2 gene of PCV2 is excised from the PCV2 after 120 serial passages of the PCV2 in PK-15 cells.

24. An infectious reciprocal chimeric nucleic acid molecule of PCV2-1 comprising a nucleic acid molecule encoding an infectious, pathogenic PCV2 which has an immunogenic ORF2 gene from a nonpathogenic PCV1 in place of an ORF2 gene of the PCV2 nucleic acid molecule.

25. A viral vaccine comprising a nontoxic, physiologically acceptable carrier and an immunogenic amount of the chimeric nucleic acid molecule of porcine circovirus (PCV1-2) according to claim 3.

26. A method of immunizing a pig against viral infection or postweaning multisystemic wasting syndrome (PMWS) caused by PCV2 comprising administering to the pig an immunologically effective amount of the vaccine according to claim 25.

* * * * *